(12) United States Patent
Takaki et al.

(10) Patent No.: US 6,569,894 B1
(45) Date of Patent: May 27, 2003

(54) ARYLALKYLBENZOFURAN DERIVATIVES AS MELATONERGIC AGENTS

(75) Inventors: Katherine S. Takaki, Middletown, CT (US); Li-Quang Sun, Glastonbury, CT (US); Graham Johnson, Madison, CT (US); James R. Epperson, Cromwell, CT (US); Stephen R. Bertenshaw, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/264,241

(22) Filed: Oct. 3, 2002

Related U.S. Application Data

(60) Provisional application No. 60/327,146, filed on Oct. 4, 2001.

(51) Int. Cl.[7] ............... A61K 31/343; C07D 307/79
(52) U.S. Cl. ............... 514/469; 549/467; 549/462
(58) Field of Search ............... 514/469; 549/467, 549/462

(56) References Cited

U.S. PATENT DOCUMENTS

| 5,276,051 A | 1/1994 | Lesieur et al. |
|---|---|---|
| 5,308,866 A | 5/1994 | Lesieur et al. |
| 5,380,750 A | 1/1995 | Lesieur et al. |
| 5,621,142 A | 4/1997 | Mochizuki et al. |
| 5,753,709 A | 5/1998 | Keavy et al. |
| 5,856,529 A | 1/1999 | Catt et al. |
| 6,211,225 B1 | 4/2001 | Takaki et al. |

FOREIGN PATENT DOCUMENTS

| EP | 0 527 687 | 2/1993 |
|---|---|---|
| WO | WO 94/07487 | 4/1994 |
| WO | WO 95/22521 | 8/1995 |

OTHER PUBLICATIONS

Arendt, J., et al., "Alleviation of Jet Lag by Melatonin: Preliminary Results of Controlled Double Blind Trial", *Br. Med. J.*, 292, pp. 1170–1172 (May 1986).

Cassone, V. M., et al., "Dose–Dependent Entrainment of Rat Circadian Rhythms by Daily Injection of Melatonin", *J. Biol. Rhythms*, 1(3), pp. 219–229 (1986).

*Primary Examiner*—Charanjit S. Aulakh
(74) *Attorney, Agent, or Firm*—Aldo A. Algieri

(57) ABSTRACT

Novel benzofuran and dihydrobenzofuran derivatives which have a binding affinity for the human melatonin receptor and, therefore, are useful as melatonergic agents.

11 Claims, No Drawings

ARYLALKYLBENZOFURAN DERIVATIVES AS MELATONERGIC AGENTS

CROSS-REFERENCE TO RELATED APPLICATIONS

This is a non-provisional application which claims the benefit of U.S. Provisional Application No. 60/327,146 filed Oct. 4, 2001.

BACKGROUND OF THE INVENTION

The invention pertains to novel arylalkylbenzofuran derivatives having drug and bio-affecting properties, to their preparation, to pharmaceutical formulations containing them and to methods of using them. These compounds possess melatonergic properties that should make them useful in treating certain medical disorders.

Melatonin (N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

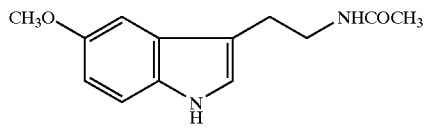

Recent evidence demonstrates that melatonin exerts its biological effects through specific receptors. Use of the biologically active, radiolabelled agonist $[^{125}I]$-2-iodomelatonin has led to the identification of high affinity melatonin receptors in the central nervous systems (CNS) of a variety of species. The sequence of one such high affinity melatonin receptor, cloned from frog melanocytes, has been reported. In the mammalian brain, autoradiographic studies have localized the distribution of melatonin receptors to a few specific structures.

Although there are significant differences in melatonin receptor distribution even between closely related species, in general the highest binding site density occurs in discrete nuclei of the hypothalamus. In humans, specific $[^{125}I]$-2-iodomelatonin binding within the hypothalamus is completely localized to the suprachiasmatic nucleus, strongly suggesting that melatonin receptors are located within the human biological clock.

Exogenous melatonin administration has been found to synchronize circadian rhythms in rats (Cassone, et al., *J. Biol. Rythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487 published on Apr. 14, 1994.

Melatonin binding sites have been found in diverse tissues of the body, i.e., in the retina, superchiasmatic nucleus, spleen, etc. This means that melatonin exerts multiple physiological effects and is not highly selective. The potential for side effects with melatonin use is large. Melatonin agonists should be more selective than melatonin and have fewer side effects. Suitable melatonin agonists could overcome melatonin's drawbacks, resulting in products having more predictable and, possibly, sustained activity.

Melatonin agonists should be particularly useful for the treatment of chronobiological disorders. They would also be useful for the further study of melatonin receptor interactions as well as in the treatment of conditions affected by melatonin activity, such as depression, work-shift syndrome, sleep disorders, glaucoma, reproduction, cancer, periondontitis, immune disorders, neuroendocrine disorders, and a variety of sleep disorders.

Aside from simple indole derivatives of melatonin itself, various amide structures have been prepared and their use as melatonin ligands disclosed. In general these amide structures can be represented as:

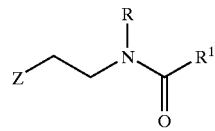

wherein Z is an aryl or heteroaryl system attached by a two carbon chain to the amide group. Some specific examples follow.

Yous, et al. in European Patent Application No. EP 527 687 A disclose, as melatonin ligands, ethylamines having cyclic substituents:

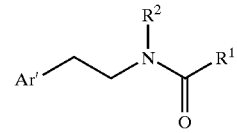

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Matsuda, et al. in International Patent Application No. WO 95/22521 disclose 1-phenyl-2-(1-aminoalkyl)-N,N-diethylcyclopropanecarboxamides as N-methyl-D-aspartate (NMDA) receptor antagonists, wherein $R_1$ represents, inter alia, a $C_1$–$C_5$ linear saturated aliphatic, a $C_1$–$C_5$ linear unsaturated aliphatic, a branched aliphatic, or a phenyl group which may be substituted with one to three substituents selected independently from the group consisting of halogen, $C_1$–$C_4$ alkyl, nitro, amino, hydroxy, and $C_1$–$C_4$ alkoxy as shown below:

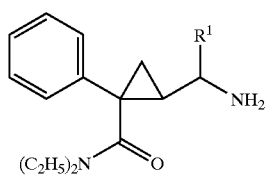

The 1,2-diarylcyclopropane derivatives disclosed in NE 6701256 have CNS stimulant properties:

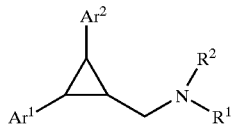

wherein $Ar_1$ and $Ar_2$ are independently and optionally substituted phenyl; $R_1$ is inter alia hydrogen, lower alkyl or acyl; $R_2$ is inter alia alkyl, cycloalkyl or aralkyl.

Keavy et al. in U.S. Pat. No. 5,753,709 issued on May 19, 1998, and assigned to the assignee of the present invention, discloses melatonergic agents of the following structure:

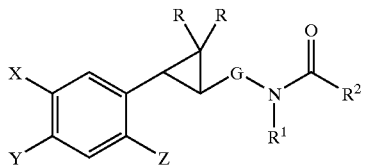

wherein X represents halogen, hydrogen, cyano, aryl, $C_{1-4}$ alkyl or $OR^5$ wherein, inter alia, $R^5$ is hydrogen, $C_{1-20}$ alkyl or $C_{4-20}$ alkylcycloalkyl; Y is hydrogen or halogen; R is hydrogen, halogen or $C_{1-4}$ alkyl; $R^1$ is hydrogen, $C_{1-4}$ alkyl or benzyl; and $R^2$ is $C_{1-6}$ alkyl, $C_{2-6}$ alkenyl, $C_{3-6}$ cycloalkyl, $C_{2-4}$ alkoxyalkyl, $C_{1-4}$ trifluoromethylalkyl or $C_{2-8}$ alkylthioalkyl.

Catt et al. in U.S. Pat. No. 5,856,529 issued on Jan. 5, 1999, and assigned to the assignee of the present invention, discloses melatonergic agents of the following structure:

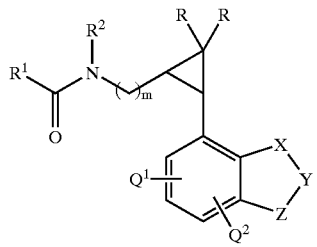

wherein $Q^1$ and $Q^2$ represent hydrogen or halogen; X is $CH_2$, CH or oxygen; Y is $CR^3$, $C^3R^4$ or $(CH_2)_n$ whereby n is 1 to 4; Z is $CH_2$, CH or oxygen,; R is hydrogen, halogen or $C_{1-4}$ alkyl; m is 1 or 2; $R^2$ is hydrogen or $C_{1-4}$ alkyl; and $R^1$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy$(C_{1-4})$alkyl, $C_{1-4}$ alkylthio$(C_{1-4})$alkyl or $C_{1-4}$ trifluoromethylalkyl.

Takaki et al. in U.S. Pat. No. 6,211,225 issued on Apr. 3, 2001, and assigned to the assignee of the present invention, discloses melatonergic agents of the following structure:

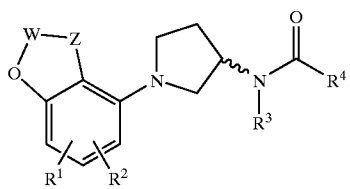

wherein the wavy bond ~~ represents the racemate, the (R)-enantiomer or the (S)-enantiomer; $R^1$ and $R^2$ each are independently hydrogen or halogen; W is $CR^5$, $CR^5R^6$ or $(CH_2)_n$ with n being 1 to 2; Z is $CH_2$, CH or oxygen; $R^3$ is hydrogen or $C_{1-4}$ alkyl; $R^4$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy$(C_{1-4})$alkyl, $C_{1-4}$ alkylthio$(C_{1-4})$alkyl or $C_{1-4}$ trifluoromethylalkyl; $R^5$ and $R^6$ are each independently hydrogen or $C_{1-4}$ alkyl.

The foregoing disclosures do not teach or suggest the novel melatonergic benzofuran and dihydrobenzofuran derivatives of the present invention. The novel compounds of the present invention display melatonergic agonist activity.

SUMMARY OF THE INVENTION

This invention provides a novel series of compounds of Formula I:

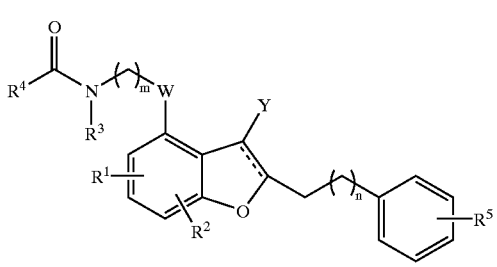

wherein $R^1$, $R^2$, $R^3$, $R^4$, $R^5$, Y, W, m, and n are as defined below, including hydrates and solvates thereof which bind to human melatonergic receptors and, as thus, are useful as melatonergic agents in the treatment of sleep disorders, seasonal depression, shifts in circadian cycles, melancholia, stress, appetite regulation, benign prostatic hyperplasia, periodontitis, and related conditions.

DETAILED DESCRIPTION OF THE INVENTION

The present invention provides a novel series of compounds of Formula I and hydrates and solvates thereof:

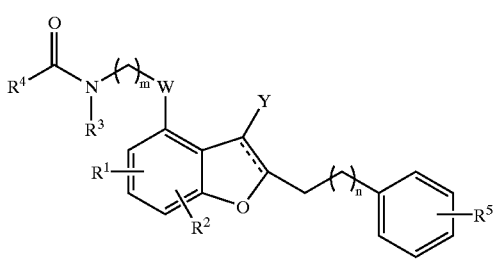

wherein
the dashed line represents a single or double bond;
$R^1$ and $R^2$ are each independently hydrogen or halogen;
$R^3$ is hydrogen or $C_{1-4}$ alkyl;
$R^4$ is $C_{1-4}$ alkyl, $C_{3-6}$ cycloalkyl, $C_{1-3}$ haloalkyl, $C_{2-6}$ alkenyl, $C_{1-4}$ alkoxy, $C_{1-2}$ trifluoromethylalkyl, or $C_{1-4}$ alkylamino;
$R^5$ is hydrogen, halogen, $C_{1-4}$ alkyl, or $C_{1-4}$ alkoxy;
Y is hydrogen or halogen;
W is ethylene or a 1,2 disubstituted cyclopropyl group;
m is 1 or 2; and
n is 1 to 9.

The present invention also provides a method of treating sleep disorders and related conditions by administering a therapeutically effective amount of a compound of Formula I or a solvate or hydrate thereof.

$R^1$ and $R^2$ are each independently hydrogen or halogen (i.e., bromine, chlorine, iodine or fluorine). It is most preferred that $R^1$ is hydrogen and $R^2$ is hydrogen.

$R^3$ is hydrogen or $C_{1-4}$ alkyl with hydrogen being most preferred.

$R^4$ may be $C_{1-4}$ alkyl, $C_{3-6}$ cycloalkyl, $C_{1-3}$ haloalkyl, $C_{2-6}$ alkenyl, $C_{1-4}$ alkoxy, $C_{1-2}$ trifluoromethylalkyl, or $C_{1-4}$ alkylamino. Preferably, $R^4$ is $C_{1-4}$ alkyl or $C_{3-6}$ cycloalkyl with $C_{1-4}$ alkyl being most preferred.

$R^5$ is hydrogen, halogen, $C_{1-4}$ alkyl, or $C_{1-4}$ alkoxy. Preferably, $R^5$ is hydrogen or halogen with hydrogen being most preferred.

X is ethylene or a divalent cyclopropyl group.

m is 1 or 2 with 1 being most preferred.

n is 1 to 9 with 1 to 4 being preferred, 2 to 4 being more preferred, and 3 to 4 being most preferred.

"Alkyl" means a monovalent straight or branched chain group of the formula $C_xH_{2x+1}$, with x being the number of carbon atoms.

"Alkenyl" means a straight or branched hydrocarbon radical containing a carbon-carbon double bond.

"Cycloalkyl" groups are monovalent cyclic moieties containing at least 3 carbon atoms and conforming to the formula $C_xH_{2x-1}$, with x being the number of carbon atoms present. The cyclopropyl group is a preferred cycloalkyl moiety.

"Haloalkyl" includes straight and branched chain hydrocarbon radicals bearing from 1 to 3 halogen moieties. "Halogen" means fluorine, chlorine, bromine, or iodine. Preferred halogens in haloalkyl moieties of $R^4$ are fluorine and chlorine.

The compounds of Formula I encompass all pharmaceutically acceptable solvates, particularly hydrates, thereof. The present invention also encompasses diastereomers as well as optical isomers, e.g., mixtures of enantiomers including racemic mixtures, as well as individual enantiomers and diastereomers, which arise as a consequence of structural asymmetry in certain compounds of Formula I. Separation of individual isomers or selective synthesis of the individual isomers is accomplished by application of various methods known to those of skill in the art.

When W is ethylene, the compounds of the present invention are represented by Formula II:

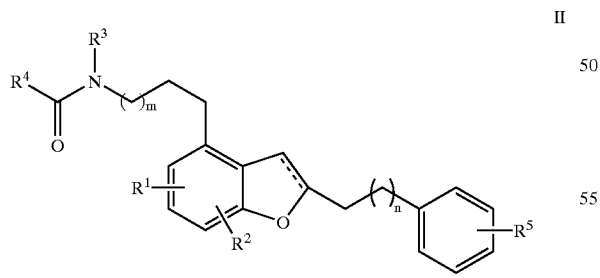

II wherein $R_1$, $R^2$, $R^3$, $R^4$, $R^5$, m, and n are as defined above. Preferably, $R^1$ is hydrogen, $R^2$ is hydrogen, $R^3$ is hydrogen, $R^4$ is $C_{1-3}$ alkyl, $R^5$ is hydrogen, m is 1, and n is 1 to 4.

The compounds of Formula II may be prepared using the processes depicted in the following Reaction Schemes 1 to 3. Reaction Scheme 1 illustrates a method of making the compounds of Formula II that contain chirality. Reaction Scheme 2 illustrates a method of making the compounds of Formula II that do not have chiral centers. Reaction Scheme 3 illustrates a method of making the compounds of Formula II that have substitution on the arylalkyl substituent of the benzofuran. Reaction Scheme 4 illustrates a method of making the compounds of Formula II having varying alkyl chain lengths of the arylalkyl substituent.

Reaction Scheme 1

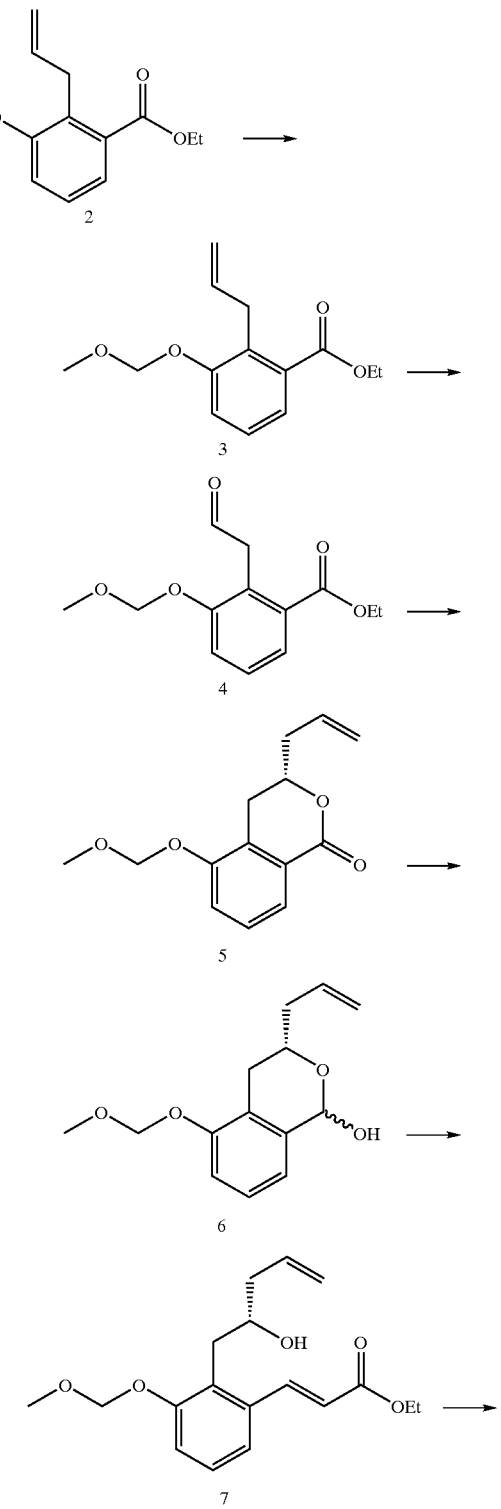

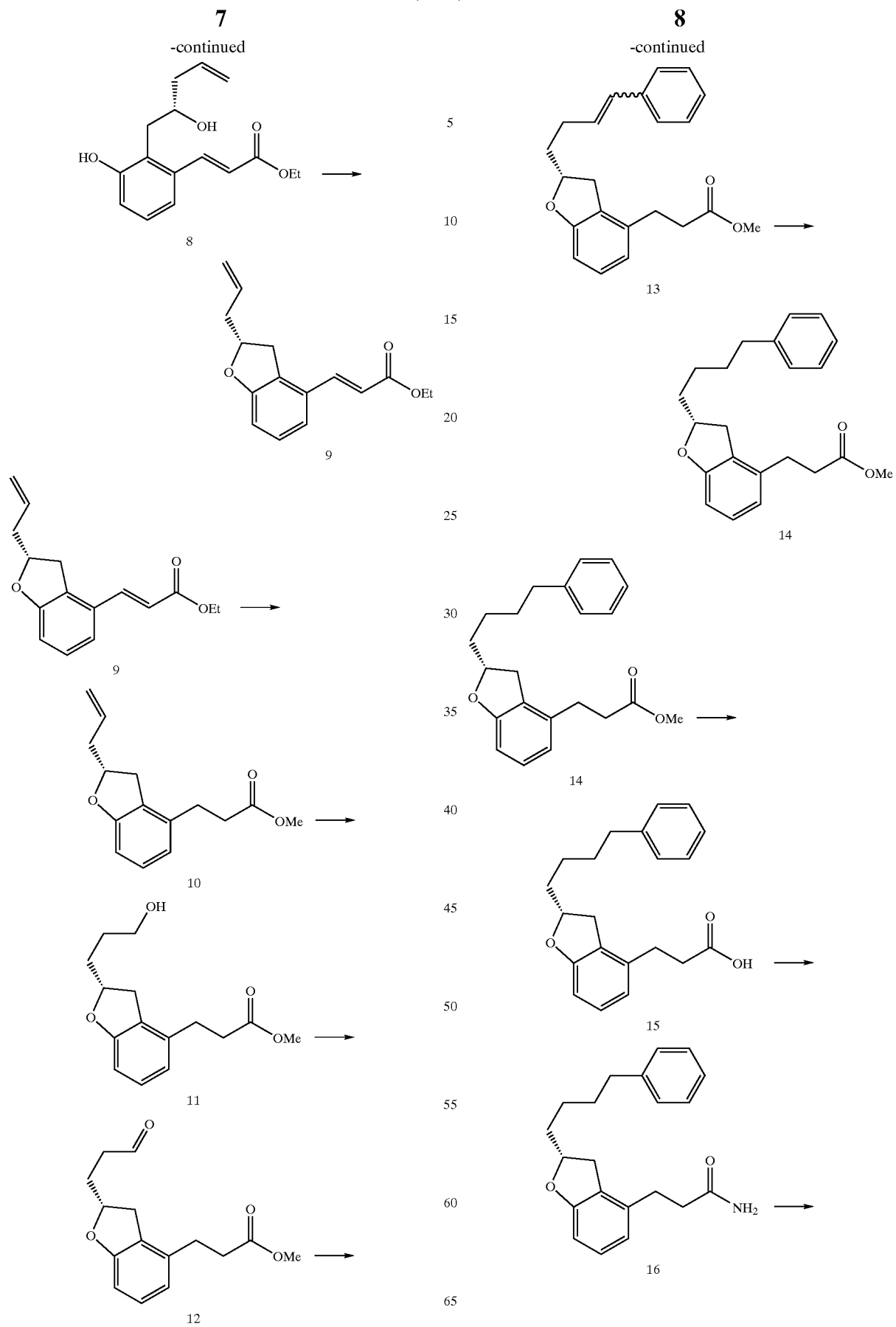

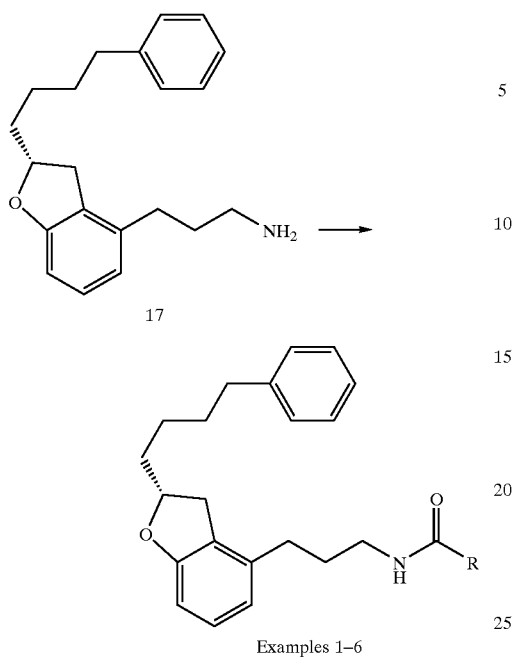
Examples 1–6
Reaction Scheme 2
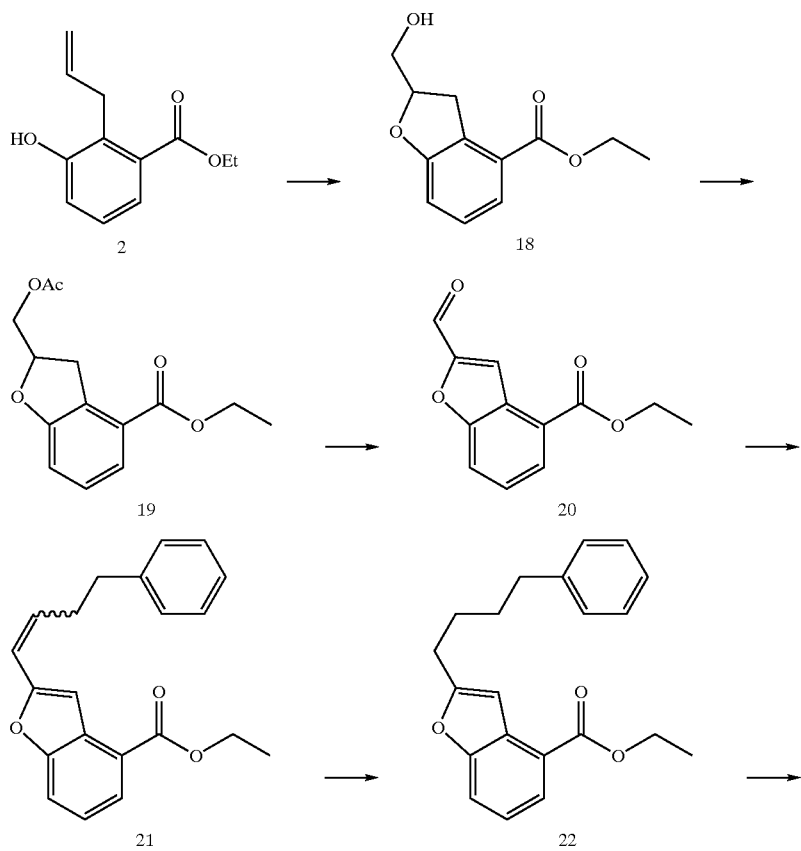

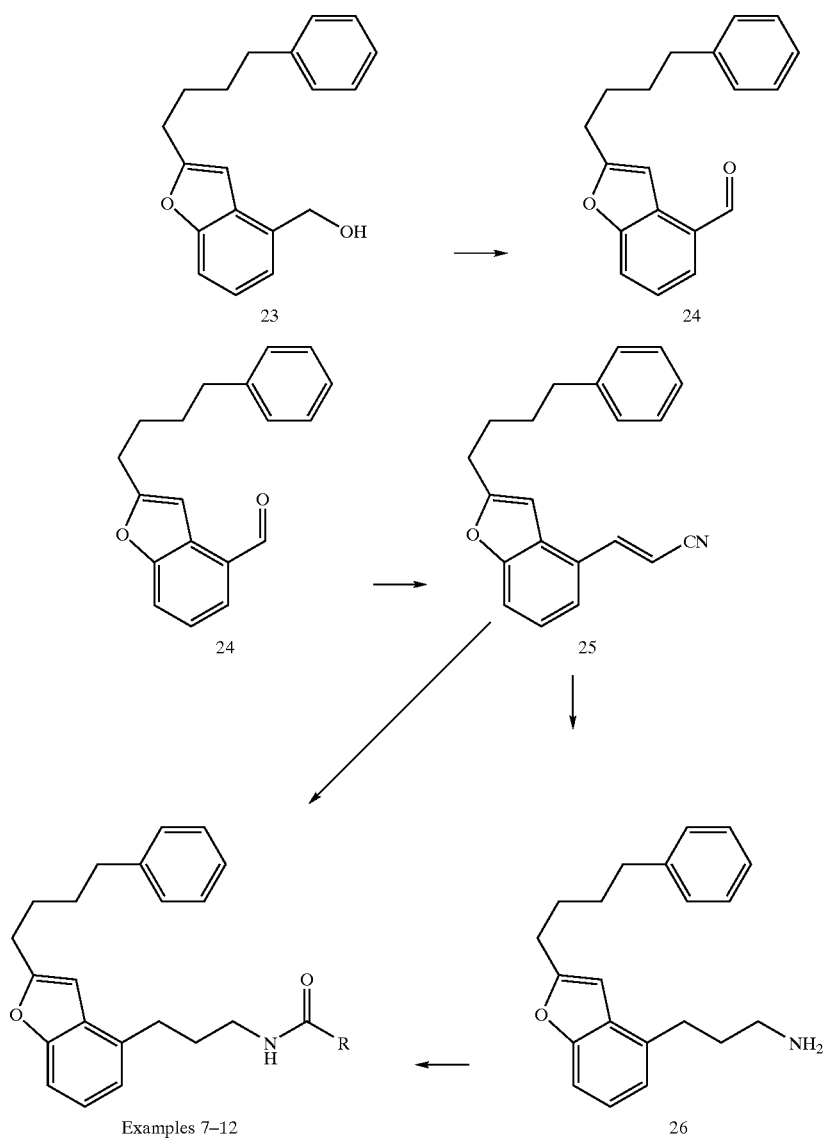
Reaction Scheme 3
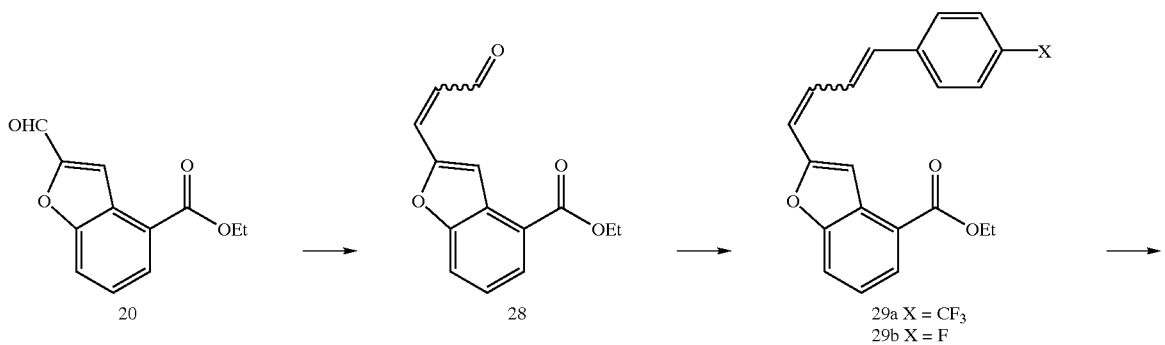

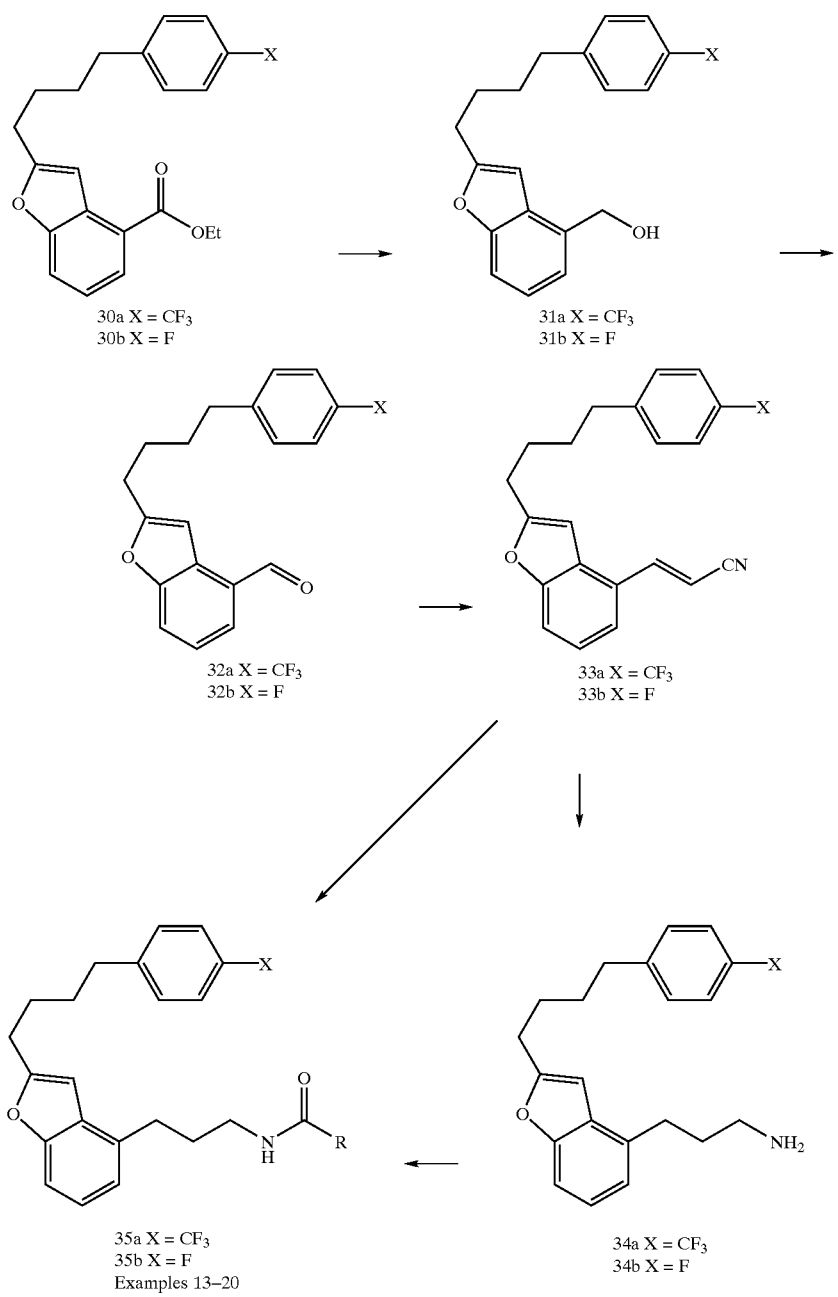
Reaction Scheme 4
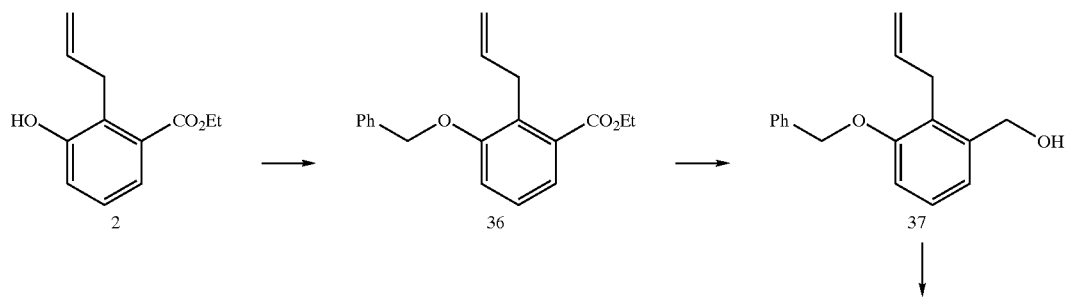

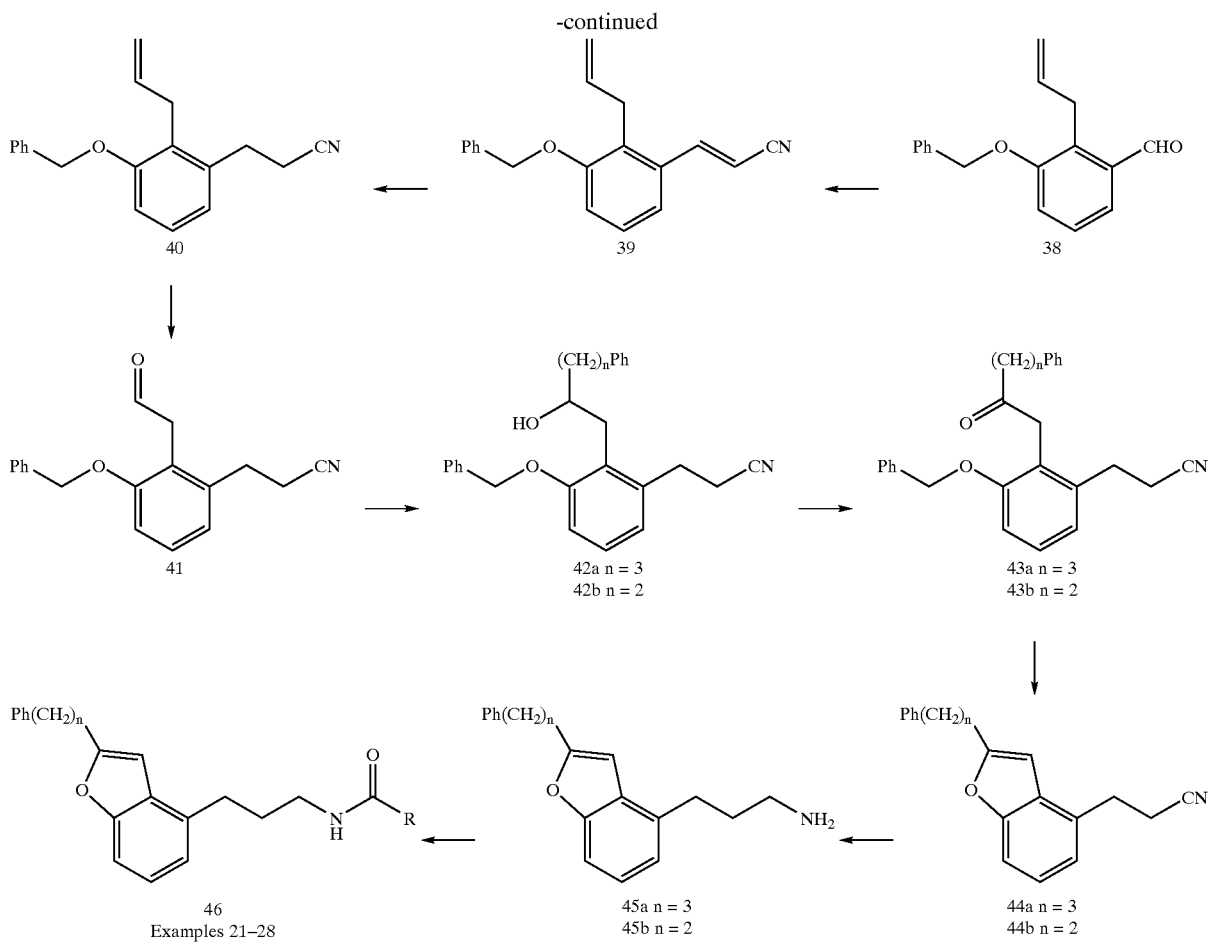

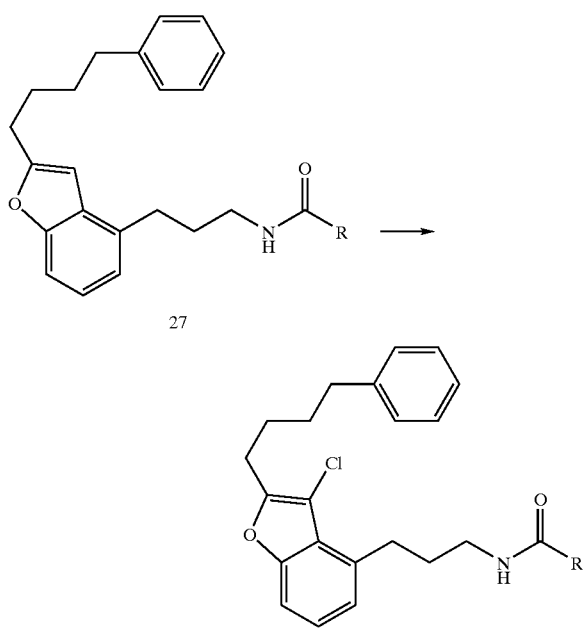

Reaction Scheme 5

Example 29

Some preferred compounds of Formula II include: N-[3-[2-(4-phenylbutyl)-2,3-dihydrobenzofuran-4-yl]-propyl]acetamide; N-[3-[2-(4-phenylbutyl)-2,3-dihydrobenzofuran-4-yl]-propyl]propionamide; N-[3-[2-(4-phenylbutyl)-2,3-dihydrobenzofuran-4-yl]-propyl]butyramide; N-[3-[2-(4-phenylbutyl)-2,3-dihydrobenzofuran-4-yl]propyl]-2-methylpropionamide; N-[3-[2-(4-phenylbutyl)-2,3-dihydrobenzofuran-4-yl]propyl]-cyclopropanecarboxamide; N-[3-[2-(4-phenylbutyl)benzofuran-4-yl]propyl]propionamide; and N-[3-[2-(4-phenylbutyl)benzofuran-4-yl]propyl]-2-methylpropionamide.

As shown in Reaction Scheme 1, the phenolic moiety of ethyl 3-hydroxy-2-allylbenzoate 2 was protected as the MOM ether by treatment with chloromethylmethyl ether. The terminal olefin was then converted to the aldehyde by the action of osmium tetroxide and sodium periodate. Addition of allyl Grignard and lactonization of the intermediate alcohol produced lactone 5. Reduction of the lactone with DIBAL followed by a Horner-Emmons addition produced the cinnamate 7. The MOM ether was cleaved with methanolic HCl and an intramolecular Mitsunoble reaction afforded the cyclic ether 9. The ester was transesterified with methanolic HCl, the terminal olefin was hydroborated, and the resulting alcohol was oxidized under Swern conditions generating aldehyde 12. Wittig condensation followed by reduction of the olefin produced intermediate 14. The ester was converted to the carboxamide followed by DIBAL mediated reduction to give amine 17. The amine was then acylated with a variety of acylating agents to give dihydrobenzofuran compounds of structure 1.

Likewise, analogous benzofuran compounds were also prepared from intermediate 2 as illustrated in Reaction Scheme 2. Oxidation of 2 with m-CPBA generated the cyclic intermediate 18 which was acylated with acetic anhydride and then oxidized with DDQ to produce aldehyde 20. Wittig olefination followed by hydrogenation afforded benzofuran 22. Reduction of the ester with LAH followed by Swern oxidation produced aldehyde 24 which was homolygated via another Wittig reaction to generate cinnamylnitrile 25. Reduction of this compound with cobalt chloride and sodium borohydride followed by acylation afforded compounds of structure 27.

In Reaction Scheme 3, intermediate 20 was converted to intermediates 29a and 29b by successive Wittig reactions. Intermediate 35 was then prepared via the same sequence as that of conversion of 21 to 27.

In Reaction Scheme 4, starting material 2 was protected as the benzyl ether. The ester was then homolygated to cinnamonitrile 39 as described above and the olefin reduced to generate intermediate 40. Elaboration of the allyl group began with conversion to the aldehyde followed by Grignard addition; the resulting alcohols were oxidized to ketones. Debenzylation and cyclization created intermediates 44a and 44b. Transformation of the nitrile to amide 46 was as described previously.

In Reaction Scheme 5, intermediate 27 is chlorinated with N-chlorosuccinimide to provide compound 47, also referred to as Example 29.

When W is cyclopropyl, the compounds of the present invention are represented by Formula III:

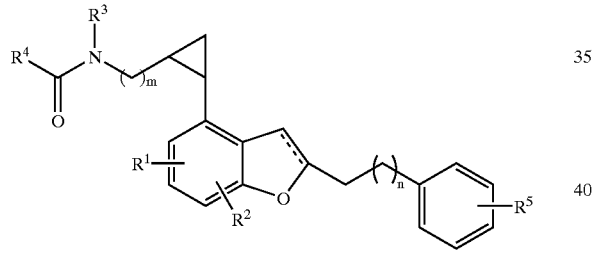

III wherein $R^1$, $R^2$, $R^3$, $R^4$, $R^5$, m, and n are as defined above. Preferably, $R^1$ is hydrogen, $R^2$ is hydrogen, $R^3$ is hydrogen, $R^4$ is $C_{1-3}$ alkyl, $R^5$ is hydrogen, m is 1, and n is 1 to 4.

The compounds of Formula III may be prepared as depicted in the following Reaction Schemes 1A and 2A. Reaction Scheme 1A illustrates a method of making the benzofuran compounds of Formula II. Reaction 2A illustrates a method of making the dihydrobenzofuran compounds of Formula III.

Reaction Scheme 1A

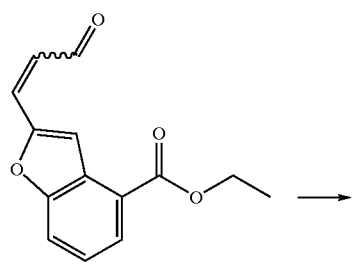

28

-continued

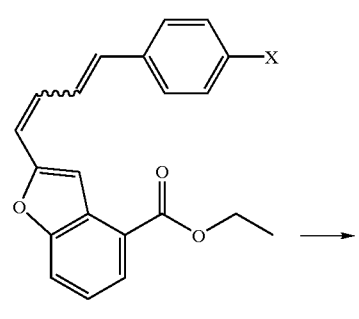

4A X = F
4B x = H

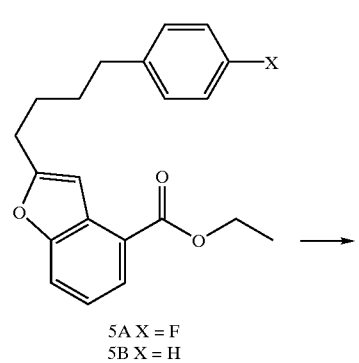

5A X = F
5B X = H

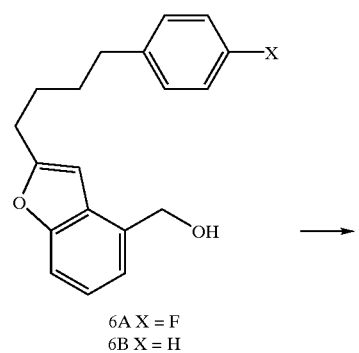

6A X = F
6B X = H

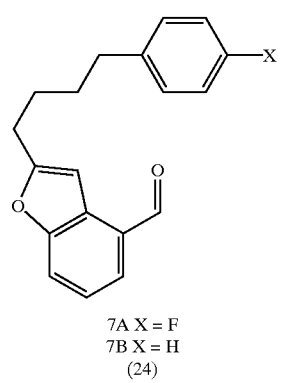

7A X = F
7B X = H
(24)

-continued
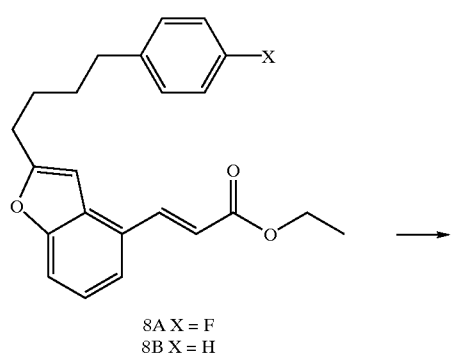
8A X = F
8B X = H
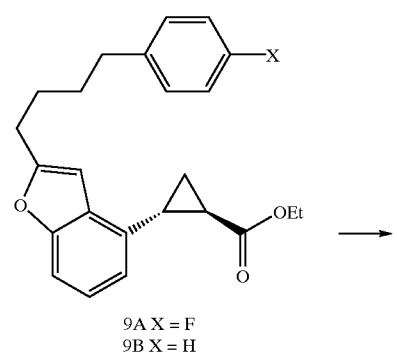
9A X = F
9B X = H
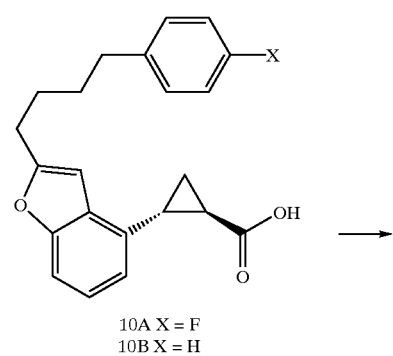
10A X = F
10B X = H
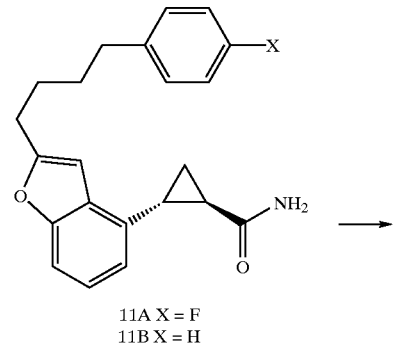
11A X = F
11B X = H
-continued
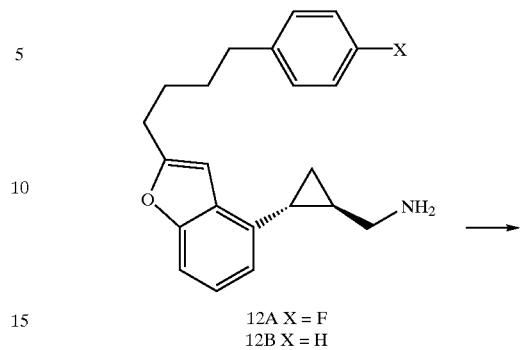
12A X = F
12B X = H
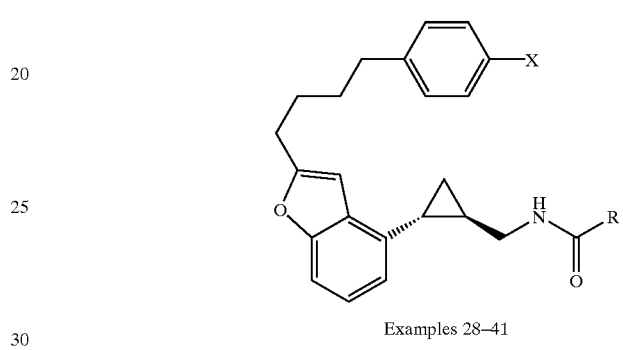
Examples 28–41
Reaction Scheme 2A
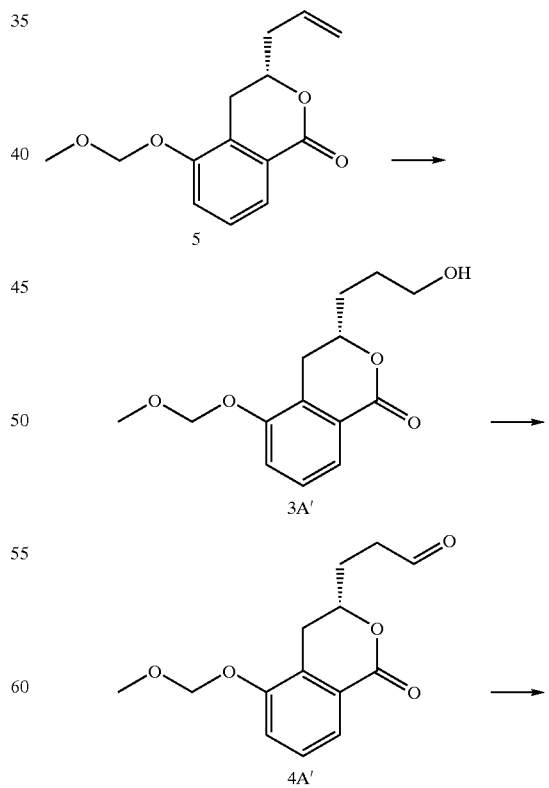

21
-continued
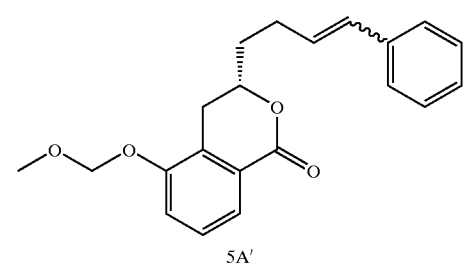
5A'
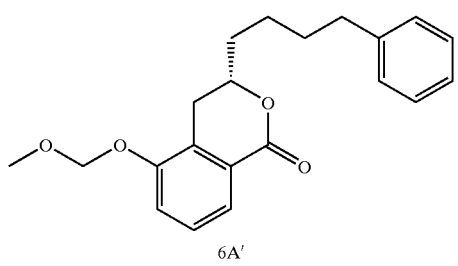
6A'
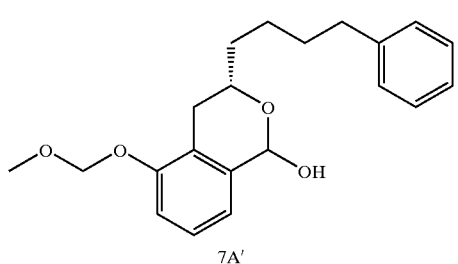
7A'
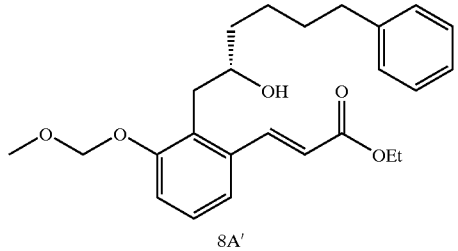
8A'
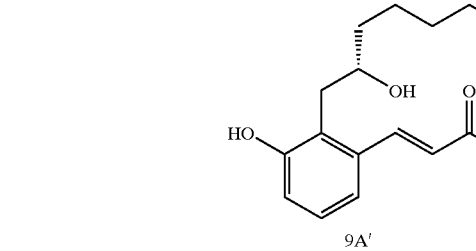
9A'
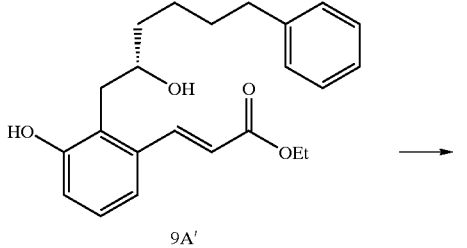
9A'
22
-continued
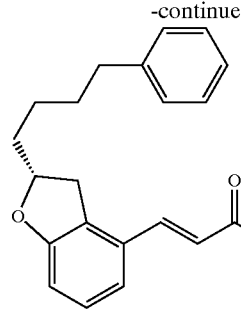
10A'
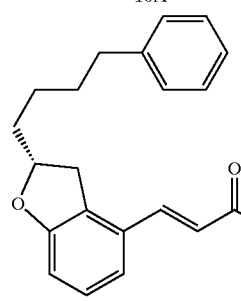
11A'
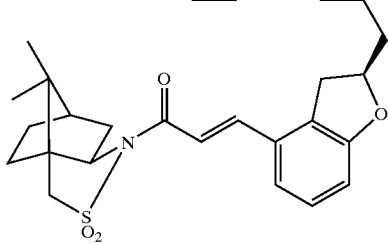
12A'
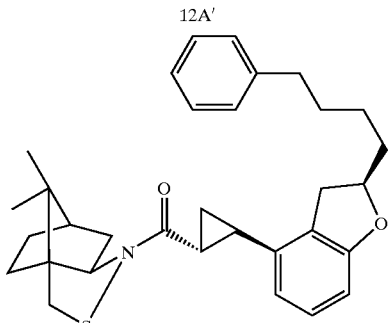
13A'
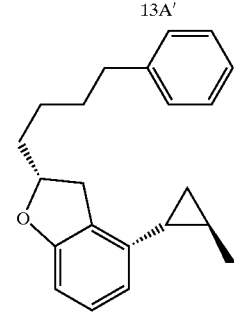
14A'

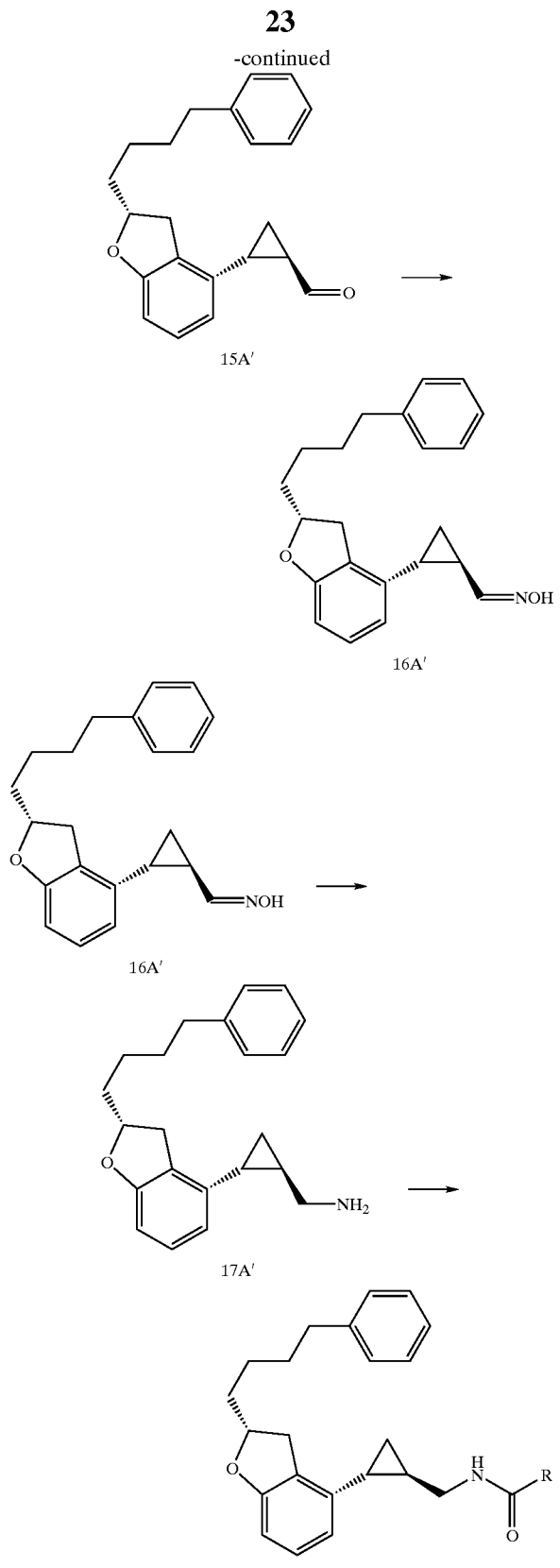

Examples 42–47

In Reaction Scheme 1A, intermediate 20 was converted to intermediate 4A by tandem Wittig reactions. Ester 4A was then converted to cinnamates 8 in a manner analogous to the conversion of intermediates 21 to 25. Cinnamates 8 were cyclopropanated by the action of palladium and diazomethane. The conversion of esters 9 to compounds 1A and 1B were analogous to the conversion of intermediate 14 to compound 1.

Scheme 2A, intermediate 5 was elaborated to intermediate 5A' by the sequence of hydroboration, Swern oxidation, and Wittig olefination. After hydrogenation of the olefin, intermediate 6A' was converted to intermediate 10A' by same sequence as that of intermediates 5 to 9. The ester was converted to the chiral sultam and the olefin cycloprapanated with palladium and diazomethane to afford intermediate 13A'. The sultam was reduced to the alcohol with LAH and the alcohol transformed to the amine by Swern oxidation, oxime formation, and reduction of the oxime. Amide 1A' was then prepared by acylation.

Some preferred compounds of Formula III include: N-({(1R,2R)-2-[2-(4-phenylbutyl)benzo[b]furan-4-yl]cyclopropyl}methyl)acetamide; (−)N-({(1R,2R)-2-[2-(4-phenylbutyl)benzo[b]furan-4-yl]cyclopropyl}methyl) acetamide; N-({(1R,2R)-2-[2-(4-phenylbutyl)benzo[b]furan-4-yl]-cyclopropyl}methyl)propanamide; N-({2-[(2R)-2-(4-phenylbutyl)(2,3-dihydrobenzo[b]furan-4-yl)](1R,2R)cyclopropyl}methyl)acetamide; N-({2-[(2R)-2-(4-phenylbutyl)(2,3-dihydrobenzo[b]furan-4-yl)]-(1R,2R)cyclopropyl}methyl)propanamide; N-({2-[(2R)-2-(4-phenylbutyl)(2,3-dihydrobenzo[b]furan-4-yl)]-(1R,2R)cyclopropyl}methyl)butanamide; and N-({2-[(2R)-2-(4-phenylbutyl)(2,3-dihydrobenzo[b]furan-4-yl)](1R,2R)cyclopropyl}methyl)cyclopropylcarboxamide.

Biological Data

The compounds of the present invention are melatonergic agents. They have been found to bind to human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the present invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, benign prostate hyperplasia, inflammatory articular disease, periodontitis, and related conditions.

Melatonergic Receptor Binding Activity

1. Reagents:
   (a) TME=50 mM Tris buffer containing 12.5 mM $MgCl_2$, and 2 mM EDTA, pH 7.4 at 37° C., with concentrated HCl.
   (b) Wash buffer: 20 mM Tris base containing 2 mM $MgCl_2$, pH 7.4 at room temperature.
   (c) $10^{-4}$ M melatonin ($10^{-5}$ M final concentration).
   (d) 2-[$^{125}$I]-iodomelatonin, 0.1 M final concentration.

2. Membrane Homogenates: The melatonin $ML_{1\alpha}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2-[$^{125}$I]-iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and re-suspended in TME buffer in the presence of 10 μg/ml aprotinin and leupeptin, and 100 μM phenylmethylsulfonylfluoride. The cells were then homogenized using a dounce homogenizer, and centrifuged. The resulting pellet was re-suspended with dounce homogenizer in TME (supplemented with the above protease inhibitors) and frozen. On the day of assay, a small aliquot was thawed on ice and re-suspended in the ice cold TME (1:50–1:100 v/v) and held on ice until assayed.

3. Incubation: 37° C. for 1 hour. Reaction is terminated by filtration. Filters were washed 3 times.

4. References: Reppert, et al., *Neuron*, 13, p. 1177–1185 (1994).

Based on biological tests, the following Formula I compounds are preferred. All have binding affinities for the human melatonin receptor with $IC_{50}$ values of 600 nM or less.

TABLE I

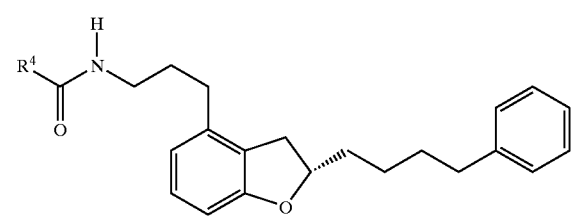

| EX | $R^4$ | $ML_{1a}$ ($IC_{50}$, nM) | $ML_{1b}$ ($IC_{50}$, nM) |
| --- | --- | --- | --- |
| 1 | Me | +++ | ++ |
| 2 | Et | +++ | ++ |
| 3 | nPr | +++ | ++ |
| 4 | iPr | +++ | ++ |
| 5 | cPr | +++ | ++ |
| 6 | NHEt | ++ | ++ |

+++ = <10 nM
++ = 10 to 250 nM
+ = >250 nM

TABLE II

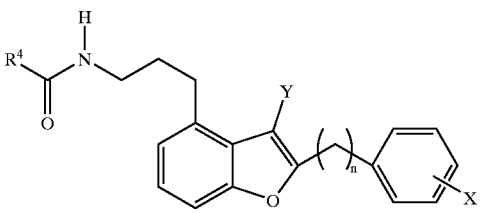

| EX | $R^4$ | $ML_{1a}$ ($IC_{50}$, nM) | $ML_{1b}$ ($IC_{50}$, nM) |
| --- | --- | --- | --- |
| 7 | cPr | ++ | ++ |
| 8 | NHEt | ++ | ++ |
| 9 | Me | ++ | ++ |
| 10 | Et | +++ | ++ |
| 11 | nPr | ++ | ++ |
| 12 | iPr | +++ | ++ |

+++ = <10 nM
++ = 10 to 250 nM
+ = >250 nM

TABLE III

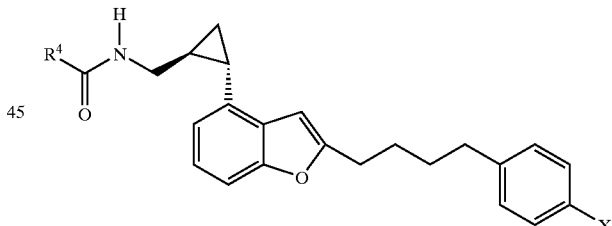

| EX | n | X | Y | R | $ML_{1a}$ ($IC_{50}$, nM) | $ML_{1b}$ ($IC_{50}$, nM) |
| --- | --- | --- | --- | --- | --- | --- |
| 13 | 4 | p-CF$_3$ | H | cPr | + | + |
| 14 | 4 | p-CF$_3$ | H | NHEt | ++ | + |
| 15 | 4 | p-CF$_3$ | H | Me | ++ | + |
| 16 | 4 | p-CF$_3$ | H | Et | ++ | ++ |
| 17 | 4 | p-CF$_3$ | H | nPr | ++ | ++ |
| 18 | 4 | p-CF$_3$ | H | iPr | ++ | + |
| 19 | 3 | H | H | Me | +++ | ++ |
| 20 | 3 | H | H | Et | ++ | + |
| 21 | 3 | H | H | nPr | ++ | + |
| 22 | 3 | H | H | cPr | ++ | + |
| 23 | 2 | H | H | Me | ++ | ++ |
| 24 | 2 | H | H | Et | ++ | ++ |
| 25 | 2 | H | H | nPr | ++ | ++ |
| 26 | 2 | H | H | cPr | ++ | ++ |
| 27 | 4 | H | Cl | Et | + | + |

+++ = <10 nM
++ = 10 to 250 nM
+ = >250 nM

TABLE IV

| EX | X | $R^4$ | $ML_{1a}$ ($IC_{50}$, nM) | $ML_{1b}$ ($IC_{50}$, nM) |
| --- | --- | --- | --- | --- |
| 28 | H | Me | +++ | ++ |
| 29 | H | Me | +++ | ++ |
| 30 | H | Me | ++ | + |
| 31 | H | Et | +++ | +++ |
| 32 | H | nPr | ++ | ++ |
| 33 | H | iPr | ++ | ++ |
| 34 | H | cPr | ++ | ++ |
| 35 | H | NHEt | ++ | ++ |
| 36 | F | Me | +++ | ++ |
| 37 | F | Et | +++ | ++ |
| 38 | F | nPr | ++ | ++ |
| 39 | F | iPr | ++ | ++ |
| 40 | F | cPr | ++ | ++ |
| 41 | F | NHEt | ++ | + |

+++ = <10 nM
++ = 10 to 250 nM
+ = >250 nM

TABLE V

[Structure: R⁴-C(=O)-NH-CH₂-cyclopropyl attached to dihydrobenzofuran with X and Y substituents, and a phenylpropyl chain on the furan]

| EX | X  | Y  | R    | ML$_{1a}$ (IC$_{50}$, nM) | ML$_{1b}$ (IC$_{50}$, nM) |
|----|----|----|------|---------------------------|---------------------------|
| 42 | H  | H  | Me   | +++                       | +++                       |
| 43 | H  | H  | Et   | +++                       | +++                       |
| 44 | H  | H  | nPr  | +++                       | +++                       |
| 45 | H  | H  | iPr  | ++                        | ++                        |
| 46 | H  | H  | cPr  | +++                       | ++                        |
| 47 | H  | H  | NHEt | ++                        | ++                        |
| 48 | Cl | H  | NHEt | ++                        | ++                        |
| 49 | Cl | Cl | nPr  | +                         | ++                        |
| 50 | H  | Cl | nPr  | ++                        | +++                       |

+++ = <10 nM
++ = 10 to 250 nM
+ = >250 nM

The compounds of the present invention have affinity for receptors of the endogenous pineal hormone, melatonin, as determined in a receptor binding assays described above in Tables I to V for the ML$_{1a}$ and ML$_{1b}$ (human) receptors. Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer benign prostatic hyperplasia, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally with pharmaceutically acceptable adjuvants and excipients employing standard conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See for example, *Remington's Pharmaceutical Sciences*, Mack Publishing Company, Easton, Pa., 17$^{th}$ edition, 1985.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or a liquid medium), ointments containing for example up to 1:0% by weight of the active compound, soft and hard gelatin capsules, suppositories, sterile injectable solutions, and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents emulsifying and suspending agents, preserving agents, sweetening agents or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient, and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used in treating sleep and related disorders in a manner similar to that used for melatonin.

However, it will be understood that the amount of the compound actually administered will be determined by a physician, in light of the relevant circumstances including the condition to be treated, the choice of compound to be administered, the chosen route of administration, the age, weight and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, all temperatures are expressed in degrees Celsius and melting points are uncorrected. Proton magnetic resonance ($^1$H NMR) and carbon magnetic resonance ($^{13}$C NMR) spectra were determined in the solvents indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet quartet. The infrared (IR) spectral descriptions include only absorption wave numbers (cm$^-$) having functional group identification value. The IR determinations were employed using the compound neat as a film or by employing potassium bromide (KBr) as diluent. Optical rotations $[\alpha]_D^{25}$ were determined in the solvents and concentration indicated. Low resolution mass spectra (MS) are reported as the apparent molecular weight (M+H)$^+$. The elemental analyses are reported as percent by weight. Conditions for analytical HPLC are: Column=YMC C18 S5 4.6 mm×50 mm; solvent A=10% MeOH, 90% H$_2$O, 0.2% H$_3$PO$_4$; solvent B=90% MeOH, 10% H$_2$O, 0.2% H$_3$PO$_4$; gradient from 0% to 100% B over 4 minutes with a 2 minute hold time at 100% B; flow=4 ml per minute; wavelength= 220 nM.

PREPARATION OF INTERMEDIATE 3

Ethyl 3-(Methoxymethoxy)-2-prop-2-enylbenzoate

A mixture of ethyl 3-hydroxy-2-prop-2-enylbenzoate, starting material 2, (10.3 g, 50 mmol), Adogen (61 g), and 10 M NaOH (10 mL, 100 mmol) in CH$_2$Cl$_2$ (100 mL) was stirred for 20 min. Chloromethylmethyl ether (159 g, 1980 mmol) was added and the reaction mixture was stirred for 1 h. The organic layer was separated. The inorganic layer was extracted with CH$_2$Cl$_2$ (50 mL×2). The combined organic layers were washed with brine (20 mL×2), dried over MgSO$_4$, and concentrated in vacuo. The crude material was purified by flash chromatography over silica gel (6% ethyl acetate/hexanes) to give 10.6 g (85%) of intermediate 3 as an oil.

$^1$H NMR (300 MHz, CDCl$_3$) δ 7.45 (dd, J=6.7, 2.3 Hz, 1H), 7.24–7.17 (m, 2H), 6.37 (d, J=7.8 Hz, 1H), 6.05–5.92 (m, 1H), 5.19 (s, 2H), 5.00–4.91 (m, 2H), 4.37–4.29 (q, J=7.1 Hz, 1H), 3.76–3.69 (m, 2H), 3.46 (s, 3H), 1.36 (t, J=6.1 Hz, 3H).

PREPARATION OF INTERMEDIATE 4

Ethyl 3-(Methoxymethoxy)-2-(2-oxoethyl)benzoate

To a solution of intermediate 3 (4.96, 20 mmol) in dioxane (75 mL) and water (75 mL) was added NaIO$_4$ (8.56 g, 40 mmol) and OsO$_4$ (250 mg, 1 mmol). The resulting mixture was stirred overnight. The insoluble material was removed by filtration and washed with EtOAc. The organic layer was separated, washed with brine, dried over MgSO$_4$, and concentrated in vacuo. The residue was purified by flash chromatography over silica gel (20% ethyl acetate/hexanes) to give 3 g (60%) of intermediate 4 as an oil.

$^1$H NMR (300 MHz, CDCl$_3$) δ 7.65–7.60 (m, 1H), 7.32–7.22 (m, 2H), 5.19 (s, 2H), 4.30 (q, J=7.1 Hz, 2H), 4.16 (d, J=1.1 Hz, 2H), 3.4 (s, 3H), 1.34 (t, J=7.1 Hz, 3H).

PREPARATION OF INTERMEDIATE 5

(3S)-5-(Methoxymethoxy)-3-prop-2-enylisochroman-1-one

To a solution of (−)Icp$_2$BOMe (83.4 g, 264 mmol) in ether (1200 mL) at 0° C. under N$_2$ was added allyl magnesium bromide (240 mL, 240 mmol). After warming to room temperature, the resulting mixture was stirred for 1 h. After cooling to −78° C., a solution of intermediate 4 (30 g, 120 mmol) in ether (50 mL) was added and the reaction mixture stirred for 1 h. The reaction was quenched with 4 N NaOH (132 mL) and allowed to warm to room temperature. After cooling to 0° C., 30% H$_2$O$_2$ (132 mL) was added and the mixture was warmed to room temperature and stirred for 16 h and then refluxed for 1 h. The organic layer was separated, washed with brine, and concentrated in vacuo. The residue was dissolved in methanol (MeOH) (240 mL) and H$_2$O (96 mL), and NaOH (19.2 g) was added. The resulting mixture was refluxed for 1 h. The MeOH was removed in vacuo and impurities in the residue were removed by extraction with ether (100 mL×5). The inorganic layer was acidified with 4 N HCl and extracted with ethyl acetate (EtOAc). The combined organic layers were dried over MgSO$_4$ and concentrated in vacuo. The crude product was purified by flash chromatography over silica gel (15% ethyl acetate/hexanes) to give 24 g (80%) of intermediate 5 as an oil.

$^1$H NMR (300 MHz, CDCl$_3$) δ 7.78–7.71 (m, 1H), 7.33–7.25 (m, 2H), 5.97–5.58 (m, 1H), 5.24–5.15 (m, 4H), 44.58–4.49 (m, 1H), 3.47 (s, 3H), 2.89–2.80 (m, 1H), 3.15 (dd, J=17.0, 3.2 Hz, 1H), 2.76–2.49 (m, 3H); $[\alpha]_D^{25}$ (+) 66 (MeOH).

PREPARATION OF INTERMEDIATE 6

(3S)-5-(Methoxymethoxy)-3-prop-2-enylisochroman-1-ol

To a solution of intermediate 5 (10 g, 40.32 mmol) in toluene (300 mL) at −78° C. was added DIBAL-H (44.35 mL, 44.35 mmol) under N$_2$. After stirring for 1 h, the reaction was quenched with 4 N NaOH (30 mL) and diluted with EtOAc (300 mL). The organic phase was washed with brine, dried over MgSO4 and concentrated in vacuo to give 9.88 g (98%) of the desired product, intermediate 6, as a solid which was used without purification in the next step.

$^1$H NMR (300 MHz, CDCl$_3$) δ 7.25–6.87 (m, 3H), 6.16–5.89 (m, 2H), 5.28–5.22 (m, 4H), 4.36–4.26 (m, 1H), 3.46–3.43 (m, 3H), 2.89–2.80 (m, 1H), 2.59–2.36 (m, 3H); m.p. 72–74° C.

PREPARATION OF INTERMEDIATE 7

Ethyl (2E)-3-[2-((2S)-2-Hydroxypent-4-enyl)-3-(methoxymethoxy)phenyl]prop-2-enoate A solution of intermediate 6 (9.8 g, 39.2 mmol) and $Ph_3PCHCO_2Et$ (27.3 g, 78.4 mmol) in THF (200 mL) was stirred for 2 days. The THF was removed in vacuo and the residue purified by flash chromatography over silica gel (30% ethyl acetate/hexanes) to give 12.04 g (96%) of the desired product, intermediate 7 as an oil.

$^1H$ NMR (300 MHz, $CDCl_3$) δ 8.03 (d, J=15.7 Hz, 1H), 7.26–7.11 (m, 3H), 6.33 (d, J=15.7 Hz, 1H), 5.94–5.80 (m, 1H), 5.23 (s, 2H), 5.20–5.12 (m, 2H), 4.25 (q, J=7.1 Hz, 2H), 3.88–3.84 (m, 1H), 3.47 (s, 3H), 3.005–2.95 (m, 2H), 2.36–2.25 (m, 2H), 1.97 (br s, 1H), 1.33 (t, J=7.1 Hz, 3H); $[\alpha]_D^{25}$ −26 (MeOH).

PREPARATION OF INTERMEDIATE 8

Ethyl (2E)-3-[2-((2S)-2-Hydroxypent-4-enyl)-3-hydroxyphenyl]prop-2-enoate

A solution of intermediate 7 (12 g, 37.5 mmol) in 2.5% concentrated HCl in MeOH (500 mL) was stirred for 16 h at room temperature. The reaction was quenched with saturated $NaHCO_3$ solution and the solvent was removed in vacuo. The residue was extracted with EtOAc and the combined organic extracts were washed with brine, dried over $MgSO_4$ and concentrated in vacuo. The crude material was purified by flash chromatography over silica gel (30% ethyl acetate/hexanes) to give 10.3 g (100%) of intermediate 8 as a solid.

$^1H$ NMR (300 MHz, $CDCl_3$) δ 8.81 (s, 1H), 8.10 (d, J=15.6 Hz, 1H), 7.18–7.10 (m, 2H), 6.98–6.93 (m, 1H), 6.31 (d, J=15.6 Hz, 1H), 5.87–5.75 (m, 1H), 5.23–5.13 (m, 2H), 4.25 (q, J=7.1 Hz, 2H), 4.09–3.96 (m, 1H), 3.02 (dd, J=15.0, 2.3 Hz, 1H), 2.90 (d, J=15.0, 8.0 Hz, 1H), 2.75 (s, 1H), 2.47–2.23 (m, 1H), 2.21–2.17 (m, 1H), 1.26 (t, J=7.1 Hz, 3H); $[\alpha]_D^{25}$ −18 (MeOH); m.p. 59–60° C.

PREPARATION OF INTERMEDIATE 9

Ethyl (2E)-3-((2R)-2-Prop-2-enyl(2,3-dihydrobenzo[b]furan-4-yl))-prop-2-enoate

To a solution of intermediate 8 (10 g, 36.23 mmol) and $Ph_3P$ (11.4 g, 43.48 mmol) in THF (200 mL) at room temperature was added dropwise a solution of DEAD (8.8 g, 43.48 mmol) in THF (10 mL) and the resulting mixture was stirred for 16 h. The THF was removed in vacuo and the residue was purified by flash chromatography over silica gel (30% ethyl acetate/hexanes) to give 8.4 g (90%) of intermediate 9 as an oil.

$^1H$ NMR (300 MHz, $CDCl_3$) δ 7.64 (d, J=16.0 Hz, 1H), 7.12 (t, J=7.8 Hz, 1H), 7.03 (d, J=7.6 Hz, 1H), 6.78 (d, J=7.7 Hz, 1H), 6.33 (d, J=7.6 Hz, 1H), 5.91–5.78 (m, 1H), 5.21–5.11 (m, 2H), 4.95–4.85 (m, 1H), 4.25 (q, J=7.1 Hz, 2H), 3.38 (dd, J=15.9, 9.1 Hz, 1H), 3.02 (dd, J=15.9, 7.3 Hz, 1H), 2.63–2.42 (m, 2H), 1.33 (t, J=7.1 Hz, 3H); $[\alpha]_D^{25}$ +101 (MeOH).

PREPARATION OF INTERMEDIATE 10

Methyl 3-((2R)-2-Prop-2-enyl-2,3-dihydrobenzo[b]furan-4-yl)propanoate

To a solution of intermediate 9 (2.58 g, 10 mmol) in MeOH (20 mL) at 0° C. under $N_2$ was added Mg (2.4 g, 100 mmol) which had been washed with 1 N HCl (5 mL), MeOH (10 mL), $Et_2O$ (20 mL), and dried. The resulting mixture was stirred for 5 h at 0° C. The MeOH was removed in vacuo and the residue extracted with EtOAc. The combined organic layers were washed with brine, dried over $MgSO_4$, and concentrated in vacuo. The crude material was purified by flash chromatography over silica gel (10% ethyl acetate/hexanes) to give 2.2 g (90%) of intermediate 10 as an oil.

$^1H$ NMR (300 MHz, $CDCl_3$) δ 7.05 (t, J=7.7 Hz, 1H), 6.64 (t, J=6.2 Hz, 2H), 5.92–5.78 (m, 1H), 5.21–5.11 (m, 2H), 4.90–4.80 (m, 1H), 3.68 (s, 3H), 3.22 (dd, J=15.3, 9.0 Hz, 1H), 2.90–2.87 (m, 3H), 2.63–2.41 (m, 4H).

PREPARATION OF INTERMEDIATE 11

Methyl 3-[(2R)-2-(3-Hydroxypropyl)-2,3-dihydrobenzo[b]furan-4-yl]propanoate

To a solution of intermediate 10 (4.92 g, 20 mmol) in THF (100 mL) at −20° C. was added borane.THF (20 mL, 20 mmol) and the resulting mixture was stirred for 2 h. The reaction was quenched with water (6 mL), then 20% NaOH (6 mL) and 30% $H_2O_2$ (6 mL) was added. After stirring: at room temperature for 2 h, the THF was removed in vacuo and the residue was extracted with diethyl ether ($Et_2O$). The combined organic layers were washed with brine, dried over $MgSO_4$, and concentrated in vacuo. The crude material was purified by flash chromatography over silica gel (50% ethyl acetate/hexanes) to give 3.17 g (60%) of the desired product of Formula 11 as an oil.

$^1H$ NMR (300 MHz, $CDCl_3$) δ 7.05 (t, J=7.8 Hz, 1H), 6.66 (d, J=7.5 Hz, 1H), 6.61 (d, J=7.9 Hz, 1H), 4.87–4.78 (m, 1H), 3.74 (t, J=5.9, 2H), 3.68 (s, 3H), 3.28 (dd, J=15.4, 9.0 Hz, 1H), 2.88–2.79 (m, 3H), 2.64–2.58 (m, 2H), 1.91–1.71 (m, 4H); $[\alpha]_{25}^D$ +50 (MeOH).

PREPARATION OF INTERMEDIATE 12

Methyl 3-[(2R)-2-(3-Oxopropyl)-2,3-dihydrobenzo[b]furan-4-yl]propanoate

To a solution of oxalyl chloride (8.5 mL, 17 mmol) in $CH_2Cl_2$ (10 mL) at −78° C. under $N_2$ was added DMSO (1.5 mL, 22.20 mmol) and the resulting mixture was stirred for 0.5 h. A solution of intermediate 11 (2.8 g, 10.6 mmol) in $CH_2Cl_2$ (5 mL) was added dropwise. After stirring for 1 h, the reaction was quenched with $Et_3N$ (5.89 mL, 42.4 mmol), allowed to warm to room temperature, and stirred for 0.5 h. The reaction was diluted with $CH_2Cl_2$, then washed with water and brine. The organic layer was dried over $MgSO_4$, concentrated in vacuo, and the residue purified by flash chromatography over silica gel (30% ethyl acetate/hexanes) to give 2.5 g (90%) of intermediate 12 as an oil.

$^1H$ NMR (300 MHz, $CDCl_3$) δ 9.83 (t, J=1.2 Hz, 1H), 7.06 (t, J=7.7 Hz, 1H), 6.67 (d, J=7.5 Hz, 1H), 6.61 (d, J=7.9 Hz, 1H), 4.87–4.77 (m, 1H), 3.68 (s, 3H), 3.30 (dd, J=15.0, 9.0 Hz, 1H), 2.88–2.79 (m, 3H), 2.72–2.58 (m, 4H), 2.10–2.02 (m, 2H); $[\alpha]_D^{25}$ +59 (MeOH).

PREPARATION OF INTERMEDIATE 13

Methyl 3-[2-((3E)-4-Phenylbut-3-enyl)(2R)-2,3-dihydrobenzo[b]furan-4-yl]propanoate To a suspension of benzyltriphenylphosphonium bromide (7.627 g, 17.6 mmol) in THF (72 mL) at 0° C. was added n-BuLi (10 mL, 16 mmol). The reaction was allowed to warm to room temperature and stirred for 1 h. A solution of intermediate 12 (2.096 g, 8 mmol) in THF was added at 0°

C. The reaction was allowed to warm to room temperature and stirred for 1 h. The reaction was quenched with water, concentrated in vacuo, and the residue extracted with EtOAc. The combined organic layers were washed with brine, dried over MgSO$_4$, and concentrated in vacuo. The crude material was purified by flash chromatography over silica gel (5% ethyl acetate/hexanes) to give 2.42 g (90%) of the desired product, intermediate 13, as a mixture of cis and trans isomers(3:1).

$^1$H NMR (300 MHz, CDCl$_3$) δ 7.37–7.18 (m, 5H), 7.09–7.03 (m, 1H), 6.68–6.62 (m, 2H), 6.49–6.43 (m, 1H), 6.31–6.21 (m, 0.75H), 5.75–5.66 (m, 0.25H), 4.90–4.78 (m, 1H), 3.69 (s, 3H), 3.33–3.18 (m, 1H), 2.90–2.75 (m, 3H), 2.62–2.41 (m, 4H), 2.08–1.79 (m, 2H).

PREPARATION OF INTERMEDIATE 14

Methyl 3-[(2R)-2-(4-Phenylbutyl)-2,3-dihydrobenzo[b]furan-4-yl]propanoate

A suspension of intermediate 13 (2.352 g, 7 mmol) and 10% Pd/C (235 mg) in EtOAc (50 mL) was hydrogenated at 60 psi overnight. After filtration through a Celite plug, the filtrate was concentrated in vacuo to give 2.35 g (99%) of intermediate 14 as an oil which was used without purification in the next step.

$^1$H NMR (300 MHz, CDCl$_3$) δ 7.32–7.26 (m, 2H), 7.21–7.16 (m, 3H), 7.06 (t, J=7.8 Hz, 1H), 6.65 (t, J=7.3 Hz, 2H), 4.82–4.72 (m, 1H), 3.69 (s, 3H), 3.21 (dd, J=15.3, 8.9 Hz, 2H), 2.89–2.76 (m, 3H), 2.68–2.58 (m, 4H), 1.94–1.44 (m, 6H); $[α]_D^{25}$ +49 (MeOH).

PREPARATION OF INTERMEDIATE 15

3-[(2R)-2-(4-Phenylbutyl)-2,3-dihydrobenzo[b]furan-4-yl]propanoic Acid

A mixture of intermediate 14 (2.2 g, 6.5 mmol) and NaOH (520 mg, 13 mmol) in MeOH (13 mL) and water (6.5 mL) was refluxed for 1 h. After cooling to room temperature, the MeOH was removed in vacuo and the aqueous residue was acidified with 4 N HCl and extracted with EtOAc. The combined organic layers were washed with brine, dried over MgSO$_4$, and concentrated in vacuo to give 2.1 g (99%) of the desired product as a solid which was used without purification in the next step.

$^1$H NMR (300 MHz, CDCl$_3$) δ 7.32–7.29 (m, 2H), 7.21–7.16 (m, 3H), 7.07 (t, J=7.7 Hz, 1H), 6.66 (t, J=7.4 Hz, 2H), 4.82–4.73 (m, 1H), 3.23 (dd, J=15.3, 8.9 Hz, 2H), 2.89–2.78 (m, 3H), 2.68–2.63 (m, 4H), 1.92–1.44 (m, 6H); $[α]_D^{25}$ +52 (MeOH); m.p. 110–111° C.

PREPARATION OF INTERMEDIATE 16

3-[(2R)-2-(4-Phenylbutyl)-2,3-dihydrobenzo[b]furan-4-yl]propanamide

A mixture of intermediate 15 (2.00 g, 6.17 mmol) and thionyl chloride (9 mL) in CH$_2$Cl$_2$ (12 mL) was refluxed for 3 h. After cooling, the solvents were removed in vacuo to give a residue. The residue was dissolved in THF (30 mL), cooled to −20° C., and liquid NH$_3$ (5 mL) was added. The resulting mixture was stirred at 0° C. for 3 h. The THF was removed and the residue was extracted with EtOAc. The combined organic layers were washed with brine, dried over MgSO$_4$, and concentrated in vacuo to give 1.8 g (90%) of the desired product as a solid which was used without purification in the next step.

$^1$H NMR (300 MHz, CDCl$_3$) δ 7.31–7.26 (m, 2H), 7.21–7.16 (m, 3H), 7.07 (t, J=7.8 Hz, 1H), 6.67 (d, J=7.5 Hz, 1H), 6.63 (d, J=7.9 Hz, 1H), 5.54 (br s, 1H), 5.35 (br s, 1H), 4.82–4.72 (m, 1H), 3.24 (dd, J=15.3, 8.9 Hz, 2H), 2.86 (t, J=8.1 Hz, 2H), 2.77 (dd, J=15.4, 7.5 Hz, 1H), 2.60 (t, J=6.3 Hz, 2H), 2.50 (t, J=6.3 Hz, 2H), 1.93–1.44 (m, 6H); $[α]_D^{25}$ +57 (MeOH); m.p. 92–93° C.

PREPARATION OF INTERMEDIATE 17

3-[(2R)-2-(4-Phenylbutyl)-2,3-dihydrobenzo[b]furan-4-yl]propylamine

To a suspension of intermediate 16 (1.615 g, 5 mmol) in toluene (20 mL) at 0° C. under N$_2$, was added 65% Red-Al (5 mL) and the resulting mixture was slowly allowed to warm to room temperature then stirred overnight. After cooling to 0° C., the reaction was quenched with MeOH (5 mL). After stirring for 0.5 h, 10 N NaOH (10 mL) was added. The reaction mixture was diluted with EtOAc and washed with brine. The organic phase was dried over MgSO$_4$ and concentrated in vacuo to give 1.46 g (94%) of intermediate 17 as an oil which was used without purification in the next step to synthesize compounds of Examples 1 to 6.

PREPARATION OF INTERMEDIATE 18

Ethyl 2-(Hydroxymethyl)-2,3-dihydrobenzo[b]furan-4-carboxylate

To a suspension of ethyl 3-hydroxy-2-prop-2-enylbenzoate 2 (412 mg, 2 mmol) and NaHCO$_3$ (336 mg, 4 mmol) in CH$_2$Cl$_2$ (10 mL) was added 3-chloroperoxybenzoic acid (1036 mg). After the resulting mixture was stirred for 2 days, the reaction was quenched with water (5 mL) and diluted with CH$_2$Cl$_2$ (20 mL). The organic layer was washed with brine, dried over MgSO$_4$, and concentrated in vacuo to give a residue. The residue was purified by flash chromatography over silica gel (elution with 33% ethyl acetate/hexanes) to give 339 mg (80%) of intermediate 18 as a solid.

$^1$H NMR (300 MHz, CDCl$_3$) δ 7.52 (dd, J=7.8, 0.9 Hz, 1H), 7.16 (t, J=7.9, 1H), 6.94 (dd, J=7.9, 0.7 Hz, 1H), 4.97–4.88 (m, 1H), 4.34 (q, J=7.1 Hz, 2H), 3.88–3.70 (m, 2H), 3.59 (dd, J=17.5, 9.5 Hz, 1H), 3.31 (dd, J=17.5, 7.3 Hz, 1H), 2.10 (s br, 1H), 1.37 (t, J=7.1 Hz, 3H); m.p. 63–64° C.

PREPARATION OF INTERMEDIATE 19

[4-(Ethoxycarbonyl)-2,3-dihydrobenzo[d]furan-2-yl] methyl Acetate

A solution of intermediate 18 (1.061 g, 5 mmol) and acetic anhydride in pyridine (3 mL) was stirred over night. The solvents were removed in vacuo and the residue was extracted with EtOAc. The organic layer was washed with water and brine, dried over MgSO$_4$, and concentrated in vacuo. The residue was purified by flash chromatography over silica gel (elution with 20% ethyl acetate/hexanes) to give 1.293 g (98%) of intermediate 19 as an oil.

$^1$H NMR (300 MHz, CDCl$_3$) δ 7.53 (dd, J=7.8, 0.9 Hz, 1H), 7.18 (t, J=7.9, 1H), 6.97 (dd, J=7.9, 0.8 Hz, 1H), 5.06–4.97 (m, 1H), 4.37–4.29 (m, 3H), 4.20 (dd, J=11.9, 6.9 Hz, 1H), 3.66 (dd, J=17.5, 9.6 Hz, 1H), 3.29 (dd, J=17.5, 7.3 Hz, 1H), 2.07 (s, 3H), 1.37 (t, J=7.1 Hz, 3H).

PREPARATION OF INTERMEDIATE 20

Ethyl 2-Formylbenzo[b]furan-4-carboxylate

A solution of intermediate 19 (19.8 g, 75 mmol) and 2.5-dichloro-3.6-dihydroxy-1,4-benzoquinone (68.1 g, 300 mmol) in dioxane (300 mL) was refluxed for 2 days. After cooling to room temperature, the solvent was removed in vacuo. The residue was dissolved in EtOAc. The organic layer was washed with brine, dried over $MgSO_4$, and concentrated in vacuo. The residue was purified by flash chromatography over silica gel (elution with 10% ethyl acetate/hexanes) to give 13.1 g (85%) of the desired product of Formula 20 as a solid.

$^1$H NMR (300 MHz, $CDCl_3$) δ 9.91 (s, 1H), 8.12 (s, 1H), 8.07 (dd, J=7.5, 0.9 Hz, 1H), 7.79 (dd, J=7.5, 0.8, 1H), 7.56 (dd, J=8.3, 7.5 Hz, 1H), 4.49 (q, J=7.1 Hz, 2H), 2.46 (s, 3H), 1.43 (t, J=7.1 Hz, 3H); m.p. 88–89° C.

PREPARATION OF INTERMEDIATE 21

Ethyl 2-((1Z)-4-Phenylbut-1-enyl)benzo[b]furan-4-carboxylate

To a suspension of $Ph_3P(CH_2)_3Br$ (20.31 g, 44 mmol) in THF (100 mL) at 0° C. under $N_2$, was added dropwise n-BuLi (16 mL, 40 mmol). After stirring for 2 h, a solution of intermediate 20 (4.36 g, 20 mmol) in THF (20 mL) was added. The resulting mixture was allowed to warm to room temperature and stirred for 1 h. The reaction was quenched with water, and THF was removed in vacuo. The residue was extracted with EtOAc. The organic layer was washed with brine, dried over $MgSO_4$, and concentrated in vacuo to give a residue. The residue was purified by flash chromatography over silica gel (elution with 10% ethyl acetate/hexanes) to give 5.474 g (85%) of intermediate 21 as a mixture of isomers.

$^1$H NMR (300 MHz, $CDCl_3$) δ 7.95–7.90 (m, 1H), 7.62–7.58 (m, 1H), 7.33–7.22 (m, 7H), 6.63–6.57 (m, 0.3H), 6.42–6.33 (m, 1H), 5.93–5.84 (m, 0.7H), 4.44 (q, J=7.1 Hz, 2H), 3.01–2.80 (m, 3.7H), 2.63–2.56 (m, 0.3H), 1.49–1.40 (m, 3H).

PREPARATION OF INTERMEDIATE 22

Ethyl 2-(4-Phenylbutyl)benzo[b]furan-4-carboxylate

A suspension of intermediate 21 (5 g, 15.6 mmol) and 10% Pd/C (500 mg) in EtOAc (100 mL) was hydrogenated at 50 psi for 16 h. After filtration and washing with EtOAc, the filtrate was concentrated in vacuo to give 5 g (99%) of intermediate 22 as an oil which was used without purification in the next step.

$^1$H NMR (300 MHz, $CDCl_3$) δ 7.93 (dd, J=7.7, 0.9 Hz, 1H), 7.55 (dt, J=8.1, 0.9 Hz, 1H), 7.30–7.14 (m, 6H), 6.98 (t, J=0.8 Hz, 1H), 4.43 (q, J=7.1 Hz, 2H), 2.83 (t, J=6.5 Hz, 2H), 2.66 (t, J=7.5 Hz, 2H), 1.87–1.65 (m, 4H), 1.40 (t, J=7.1 Hz, 3H).

PREPARATION OF INTERMEDIATE 23

Ethyl 2-(4-Phenylbutyl)benzo[b]furan-4-carboxylate

To a solution of intermediate 22 (4.83 g, 15 mmol) in THF (100 mL) was added $LiAlH_4$ (1.14 g, 30 mmol) and the resulting mixture was stirred for 1 h. After the reaction was quenched using the Fisher method, the insolubles were removed through a Celite plug and washed with THF. The filtrate was concentrated in vacuo and the residue was extracted with EtOAc. The organic layer was washed with brine, dried over $MgSO_4$, and concentrated in vacuo to give 4.15 g (99%) of the desired product of intermediate 23 as an oil which was used without purification in the next step.

$^1$H NMR (300 MHz, $CDCl_3$) δ 7.37–7.14 (m, 8H), 6.50 (dd, J=1.7, 0.8 Hz, 1H), 4.87 (s, 2H), 2.80 (t, J=6.5 Hz, 2H), 2.66 (t, J=7.4 Hz, 2H), 1.87–1.68 (m, 4H).

PREPARATION OF INTERMEDIATE 24

2-(4-Phenylbutyl)benzo[b]furan-4-carbaldehyde

To a solution of oxalyl chloride (11.6 mL, 23.2 mmol) in $CH_2Cl_2$ (28 mL) at –78° C. under $N_2$ was added DMSO (2.059 mL, 29 mmol) and stirred for 1 h. A solution of intermediate 23 (4.031 g, 14.5 mmol) in $CH_2Cl_2$ (5 mL) was added dropwise. After stirring for 1 h, the reaction was quenched with $Et_3N$ (8.06, 58 mmol) and allowed to warm to room temperature, and stirred for 1 h. The reaction was quenched with water. The organic layer was washed with brine, dried over $MgSO_4$, and concentrated in vacuo to give a residue. The residue was purified by flash chromatography over silica gel (elution with 10% ethyl acetate/hexanes) to give 3.42 g (85%) of the desired product as an oil.

$^1$H NMR (300 MHz, $CDCl_3$) δ 10.17 (s, 1H), 7.68–7.62 (m, 2H), 7.37–6.90 (m, 7H), 2.85 (t, J=6.5 Hz, 2H), 2.67 (t, J=7.5 Hz, 2H), 1.88–1.68 (m, 4H).

PREPARATION OF INTERMEDIATE 25

(2E)-3-[2-(4-Phenylbutyl)benzo[b]furan-4-yl]prop-2-enenitrile

A solution of intermediate 24 (3.33 g, 12 mmol) and $Ph_3PCHCN$ (5.44 g, 18 mmol) in THF (100 mL) was refluxed for 36 h. After THF was removed in vacuo, the residue was purified by flash chromatography over silica gel (elution with 10% $CH_2Cl_2$) to give 3.431 g (95%) of the desired product as an oil.

$^1$H NMR (300 MHz, $CDCl_3$) δ 7.62 (d, J=16.6, 1H), 7.45 (dd, J=7.1, 0.8 Hz, 1H), 7.32–7.16 (m, 7H), 6.50 (d, J=0.8 Hz, 1H), 5.92 (d, J=16.6 Hz, 1H), 2.82 (t, J=6.6 Hz, 2H), 2.67 (t, J=7.0 Hz, 2H), 1.88–1.68 (m, 4H).

PREPARATION OF INTERMEDIATE 26

3-[2-(4-Phenylbutyl)benzo[b]furan-4-yl]propylamine

To a solution of intermediate 25 (1.24 g, 4 mmol) and $CoCl_2.6H_2O$ (3.308 g, 16 mmol) in MeOH (40 mmol) at 0° C. was added $NaBH_4$ (3.04 g, 80 mmol) in portions. The resulting mixture was allowed to warm to room temperature and stirred overnight. The reaction was quenched with 6 N HCl and MeOH and the solvent was removed in vacuo. The residue was neutralized with ammonium hydroxide and extracted with EtOAc. The organic layer was washed with brine, dried, and concentrated to give 1.105 g (90%) of intermediate 26 as an oil which was used without purification in the next step to synthesize Examples 7 to 12 as discussed below.

PREPARATION OF INTERMEDIATE 28

Ethyl 2-((1Z)-3-Oxoprop-1-enyl)benzo[b]furan-4-carboxylate

Intermediate 20 (24 mmol) and triphenylphosphoranylidine acetaldehyde (48 mmol) in THF was stirred at reflux for 4 hours. The reaction was cooled and the solvent removed in vacuo. The crude product was purified by silica gel chromatography (10%–20% EtOAc/hex) to give intermediate 28 in 55% yield.

$^1$H NMR (300 MHz, $CDCl_3$) δ 9.77 (s, 1H), 9.74 (s, 1H), 8.02 (d, J=4.1 Hz, 1H), 8.01 (d, J=6.0 Hz, 1H), 7.772–7.65 (m, 4H), 7.49–7.38 (m, 2H), 6.88 (d, J=15.7 Hz, 1H), 6.86 (d, J=15.6 Hz, 1H), 4.46 (q, J=7.0 Hz, 2H), 1.47 (t, J=7.1 Hz, 3H).

PREPARATION OF INTERMEDIATES 29a & 29b

Intermediate 29a (X=CF$_3$)

Ethyl 2-{(1Z,3E)-4-[4-(Trifluoromethyl)phenyl]buta-1,3-dienyl}benzo[b]furan-4-carboxylate As illustrated in Reaction Scheme 3, intermediate 29a was prepared by adding n-BuLi (16 mL, 40 mmol) dropwise to a suspension of Ph$_3$PCH$_2$PhCF$_3$ (p) (20.04 g, 40 mmol) in THF (100 mL) at 0° C. under N$_2$. After stirring for 1 h, a solution of intermediate 28 (4.7 g, 19.7 mmol) in THF (20 mL) was added. The resulting mixture was allowed to warm to room temperature and stirred for 1 h. The reaction was quenched with water, and THF was removed in vacuo to give a residue. The residue was extracted with EtOAc. The organic layer was washed with brine, dried over MgSO$_4$, and concentrated in vacuo to give a residue. The residue was purified by flash chromatography over silica gel (elution with 10% ethyl acetate/hexanes) to give 7 g (94%) of the desired product as a mixture of isomers.

$^1$H NMR (300 MHz, CDCl$_3$) δ 7.97–7.93 (m, 1H), 7.70–6.40 (m, 11H), 4.49–4.41 (m, 2H), 1.49–1.44 (m, 3H).

Intermediate 29b (X=F)

Ethyl 2-[(1Z,3E)-4-(4-Fluorophenyl)buta-1,3-dienyl]benzo[b]furan-4-carboxylate

Intermediate 29b was prepared by the general procedure described in synthesizing intermediate 29a using 13 mmol of intermediate 28 and 26 mmol of Ph$_3$PCH$_2$PhF (p) which provided intermediate 29b in 67% isolated yield.

$^1$H NMR (300 MHz, CDCl$_3$) δ 9.95–9.92 (m, 1H), 7.60–6.36 (m, 12H), 4.49–4.41 (m, 2H), 1.49–1.43 (m, 3H).

PREPARATION OF INTERMEDIATES 30a & 30b

Intermediate 30a (X=CF$_3$)

Ethyl 2-{4-[4-(Trifluoromethyl)phenyl]butyl}benzo[b]furan-4-carboxylate

A suspension of intermediate 29a (6.9 g, 17.9 mmol) and 10% Pd/C (1.4 mg) in EtOAc (100 mL) was hydrogenated at 50 psi for 16 h. After filtration and washing with EtOAc, the filtrate was concentrated in vacuo to give 5 g (99%) of the desired product that was used without purification in the next step. No analysis was undertaken of the crude product.

Intermediate 30b (X=F)

Ethyl 2-[4-(4-Fluorophenyl)butyl]benzo[b]furan-4-carboxylate

The compound was prepared by subjecting intermediate 29b to the general procedure described above. The desired product was used in the next step without purification.

$^1$H NMR (300 MHz, CDCl$_3$) δ 7.93 (d, J=7.8 Hz, 1H), 7.57 (d, J=8.0 Hz, 1H), 7.23 (t, J=7.8 Hz, 1H), 7.13 (m, 2H), 4.44 (q, J=7.11 Hz, 2H), 2.86–2.31 (m, 2H), 2.67–2.61 (m, 2H), 1.84–1.70 (m, 4H), 1.45 (t, J=7.1 Hz, 3H).

PREPARATION OF INTERMEDIATES 31a & 31b

Intermediate 31a (X=CF$_3$)

(2-{4-[4-(Trifluoromethyl)phenyl}butyl]benzo[b]furan-4-yl)methan-1-ol

A solution of intermediate 30a (6 g, 15.4 mmol) in THF (75 mL) was added to a mixture of LiAlH$_4$ (1.17 g, 30.8 mmol) in THF (25 mL) and the resulting mixture was stirred for 1 h. After the reaction was quenched using the Fieser method, the insolubles were removed through a Celite plug and washed with THF. The filtrate was concentrated in vacuo to give a residue. The residue was extracted with EtOAc. The organic layer was washed with brine, dried over MgSO$_4$, and concentrated in vacuo to give 4.15 g (99%) of intermediate 31a that was used without purification in the next step.

$^1$H NMR (300 MHz, CDCl$_3$) δ 7.56–7.10 (m, 7H), 6.53 (d, J=0.5 Hz, 1H), 4.86 (s, 2H), 2.85 (t, J=6.6 Hz, 2H), 2.76 (t, J=7.4 Hz, 2H), 1.87–1.66 (m, 4H).

Intermediate 31b (X=F)

{2-[4-(4-Fluorophenyl)butyl]benzo[b]furan-4-yl}methan-1-ol

The compound was prepared in quantitative yield by subjecting intermediate 30b to the general procedure described above, and was used in the next step without further purification.

$^1$H NMR (300 MHz, CDCl$_3$) δ 7.38–6.93 (m, 7H), 6.52 (s, 1H), 4.89 (s, 2H), 2.83–2.78 (m, 2H), 2.66–2.59 (m, 2H), 1.85–1.24 (m, 4H).

PREPARATION OF INTERMEDIATES 32a & 32b

Intermediate 32a (X=CF$_3$)

2-{4-[4-(Trifluoromethyl)phenyl]butyl}benzo[b]furan-4-carbaldehyde

DMSO (1.9 mL, 27.2 mmol) was added to a solution of oxalyl chloride (10.9 mL, 21.76 mmol) in CH$_2$Cl$_2$ (26 mL) at −78° C. under N$_2$ with stirring for 1 h. A solution of intermediate 31a (4.7 g, 13.6 mmol) in CH$_2$Cl$_2$ (10 mL) was added dropwise. After stirring for 1 h, the reaction was quenched with Et$_3$N (7.5 mL, 54.4 mmol), allowed to warm to room temperature, and stirred for 1 h. The reaction was quenched with water. The organic layer was washed with brine, dried over MgSO$_4$, and concentrated in vacuo to give a residue. The residue was purified by flash chromatography over silica gel (elution with 10% ethyl acetate/hexanes) to give 2.8 g (60%) of the desired product as an oil.

$^1$H NMR (300 MHz, CDCl$_3$) δ 7.70–7.27 (m, 7H), 7.17 (d, J=0.7 Hz, 1H), 2.89 (t, J=6.6 Hz, 2H), 2.73 (t, J=7.4 Hz, 2H), 1.89–1.62 (m, 4H).

Intermediate 32b (X=F)

2-[4-(4-Fluorophenyl)butyl]benzo[b]furan-4-carbaldehyde

The compound was prepared in 64% crude yield by subjecting intermediate 31 b to the general procedure described above, and taken to the next step without purification.

$^1$H NMR (300 MHz, CDCl$_3$) δ 10.18 (s, 1H), 7.70–7.64 (m, 2H), 7.39–7.34 (m, 1H), 7.16–7.10 (m, 2H), 6.99–6.93 (m, 2H), 2.88–2.83 (m, 2H), 2.67–2.62 (m, 2H), 1.85–1.72 (m, 4H).

PREPARATION OF INTERMEDIATES 33a & 33b

Intermediate 33a (X=CF$_3$)

4-((1E)But-1-en-3-ynyl)-2-{4-[4(trifluoromethyl)phenyl]butyl}benzo[b]furan

60% NaH (800 mg, 20 mmol) was added to a solution of diethyl cyanomethyl phosphonate (3.54 g, 20 mmol). After stirring for 0.5 h, a solution of intermediate 32a (2.5 g, 7.27 mmol) in THF (5 mL) was added. The resulting mixture was stirred for 2 h. The reaction was quenched with water and THF was removed. The residue was extracted with EtOAc. The organic layer was washed with brine, dried over MgSO$_4$, and concentrated in vacuo to give a residue. The residue was purified by flash chromatography over silica gel (elution with 10% ethyl acetate in hexane) to give 2.67 g (96%) of the desired product as an oil.

$^1$H NMR (300 MHz, CDCl$_3$) δ 7.67 (d, J=16.7 Hz, 1H), 7.55–7.22 (m, 7H), 6.56 (d, J=0.7 Hz, 1H), 5.98 (d, J=16.7 Hz, 1H), 2.87 (t, J=6.6 Hz, 2H), 2.76 (t, J=7.4 Hz, 2H), 1.88–1.71 (m, 4H).

Intermediate 33b (X=F)

4-((1E)But-1-en-3-ynyl)-2-[4-(4-fluorophenyl)butyl]benzo[b]furan

The compound was prepared in 10% isolated yield by subjecting intermediate 32b to the general procedure described above.

$^1$H NMR (CDCl$_3$, 300 MHz): δ 7.64 (d, J=16.6 Hz, 1H), 7.45 (d, 8.0 Hz, 1H), 7.33 (d, J=7.2 Hz, 1H), 7.24 (t, J=7.8 Hz, 1H), 7.15–7.11 (m, 2H), 7.00–6.83 (m, 2H), 6.54 (s, 1H), 5.95 (d, J=16.6 Hz, 1H), 2.86–2.81 (m, 2H), 2.65–2.60 (m, 2H), 1.85–1.76 (m, 4H).

PREPARATION OF INTERMEDIATES 34a & 34b

Intermediate 34a (X=CF$_3$)

3-(2-{4-[4-(Trifluoromethyl)phenyl]butyl}benzo[b]furan-4-yl)propylamine

A suspension of intermediate 33a (734 mg, 2 mmol) and 10% Pd/C (367 mg) in acetic acid (20 mL) was hydrogenated at 60 psi for 20 h. After filtration, the filtrate was concentrated to give a residue. The residue was made basic with NaOH and extracted with EtOAc. The organic layer was washed with brine, dried, and concentrated to give 522 mg (90%) of the desired product, intermediate 34a, that was used without purification in the next step to synthesize Examples 13 to 27 described below.

Intermediate 34b (X=F)

3-{2-[4-(4-Fluorophenyl)butyl]benzo[b]furan-4-yl}propylamine

The title compound was prepared in accordance with the method of intermediate 34a and taken to the next step without purification or analysis.

PREPARATION OF INTERMEDIATE 36

Ethyl 3-(Phenylmethoxy)-2-prop-2-enylbenzoate

Intermediate 2 (20.00 g, 97.08 mmol), allylbromide (17.44 g, 101.99 mmol), and potassium carbonate (20.70 g, 150.00 mmol) were added to acetone (100 mL) and heated to reflux for 16 h when thin layer chromatography (TLC) analysis indicated the reaction was complete. After cooling, the acetone was removed by rotary evaporation. The residue was taken up in water and methylene chloride and partitioned. The organic layer was dried and the solvent removed by rotary evaporation to afford crude intermediate 36 as a yellow oil which was taken onto the next step without purification.

$^1$H NMR (CDCl$_3$) δ 7.45–7.05 (m, 3H), 6.01 (m 1H), 5.11 (s, 2H), 5.02 (d, J=7.3 Hz, 1H), 4.96 (s, 1H), 4.36 (q, J=7.6 Hz, 2H), 3.80 (bd, J=6.2 Hz, 2H), 1.39 (t, J=7.1 Hz, 3H).

PREPARATION OF INTERMEDIATE 37

3-Benzyloxy-2-allybenzyl Alcohol

A solution of crude intermediate 36 in THF (50 mL) was slowly added to a suspension of LAH (7.60 g, 200.00 mmol) in THF (50 mL). The reaction proceeded at room temperature for 4 h when TLC analysis indicated the reaction was complete. The reaction was diluted with ether and quenched slowly with 1N NaOH (40 mL). After stirring for 1 h, the granular suspension was filtered and the solvent removed by rotary evaporation to afford crude 3-benzyloxy-2-allylbenzyl alcohol as a colorless oil which was taken onto the next step without purification.

$^1$H NMR (CDCl$_3$) δ 7.46–6.91 (m, 3H), 6.04 (m 1H), 5.11 (s, 2H), 4.97 (m, 2H), 4.72 (s, 2H), 3.59 (bd, J=5.9 Hz, 2H), 1.39 (t, J=7.1 Hz, 3H).

PREPARATION OF INTERMEDIATE 38

3-Benzyloxy-2-allylbenzaldehyde

A solution of DMSO (23.40 g, 300.00 mmol) in methylene chloride (50 mL) was slowly added to a solution of oxalyl chloride (100 mL of a 2M solution, 200.00 mmol) in methylene chloride at −78° C. and allowed to react for 2 h. A solution of crude intermediate 37 in methylene chloride (50 mL) was added slowly and allowed to react for 2 h at −78° C. The reaction was quenched with triethylamine (80.80 g, 800.00 mmol) and allowed to warm to room temperature. The suspension was washed with 1 N HCl and the solvent removed by rotary evaporation to afford crude 3-benzyloxy-2-allylbenzaldehyde as a tan oil which was taken onto the next step without further purification.

$^1$H NMR (CDCl$_3$) δ 10.29 (s, 1H), 7.55–7.16 (m, 3H), 6.04 (m 1H), 5.14 (s, 2H), 4.95 (m, 2H), 3.92 (bd, J=6.2 Hz, 2H).

PREPARATION OF INTERMEDIATE 39

3-Benzyloxy-2-allylcinnamonitrile

A solution of diethyl cyanomethylphosphonate (19.47 g, 110.00 mmol) in THF (50 mL) was slowly added to a suspension of 60% sodium hydride (4.40 g, 110.00 mmol) in THF (50 mL) at 0° C. and allowed to react for 0.5 h. A solution of crude intermediate 38 in THF (100 mL) was added and allowed to warm to room temperature and react for 16 h when TLC analysis indicated the reaction was complete. The reaction was quenched with water and extracted with methylene chloride. The solvent was removed by rotary evaporation to afford a brown solid. The product was purified using flash chromatography (10% ethyl acetate/hexanes) to afford the title compound (19.10 g, 69.45 mmol, 71% yield) as a yellow solid. There was a 3:1 mixture of isomers which was taken onto the next step without analysis.

PREPARATION OF INTERMEDIATE 40

3-Benzyloxy-2-allyldihydrocinnamonitrile

A solution of intermediate 39 (19.10 g, 69.45 mmol) in methanol (250 mL) was added to a suspension of magnesium turnings (16.80 g, 700.00 mmol) in methanol. The reaction proceeded for 16 h. The milky suspension was filtered and the residue was washed with EtOAc. The solvent was removed by rotary evaporation to afford the title compound (17.18 g, 62.02 mmol, 89% yield) as a brown solid.

¹H NMR (CDCl₃) δ 7.45–7.34 (m, 5H), 7.19 (t, J=8.0, 1H), 6.87 (t, J=7.5, 2H), 5.96 (m, 1H), 5.09 (s, 2H), 4.96 (m, 2H), 3.52 (bd, J=6.0 Hz, 2H), 3.00 (t, J=7.6 Hz, 2H), 2.60 (t, J=7.6 Hz, 2H).

PREPARATION OF INTERMEDIATE 41

3-Benzyloxy-2-(2-ethanal)dihydrocinnamonitrile

Osmium tetroxide (1 g) was added to a solution of intermediate 40 (17.18 g, 62.02 mmol) in EtOAc (150 mL). Sodium periodate (26.54 g, 124.00 mmol), dissolved in hot water (150 mL), was added to the solution and the reaction proceeded at room temperature with vigorous stirring for 16 h when TLC analysis indicated the reaction was complete. The organic layer was collected and the aqueous layer washed with EtOAc. The solvent was removed from the combined organic layers to afford the crude product. The product was purified by flash chromatography (25% ethyl acetate/hexanes) to afford the title compound (10.84 g, 38.85 mmol, 63% yield) as an off-white solid.

¹H NMR (CDCl₃) δ 9.74 (s, 1H), 7.44–7.24 (m, 6H), 6.94–6.90 (m, 2H), 5.09 (s, 2H), 3.83 (s, 2H), 2.96 (t, J=7.6 Hz, 2H), 2.58 (t, J=7.6 Hz, 2H).

PREPARATION OF INTERMEDIATES 42a & 42b

Intermediate 42a (n=3)

Intermediate 42b (n=2)

3-Benzyloxy-2-(2-hydroxyalkyl) dihydrocinnamonitrile Compounds

A solution of Grignard reagent (1.3 eq) was added to a solution of intermediate 41 (1 eq) in THF at −78° C. The reaction was allowed to proceed for 2 h and then warmed to room temperature and quenched with saturated ammonium chloride. 1N HCl was added and the reaction mixture was extracted with EtOAc. The organic solution was dried and the solvent removed by rotary evaporation to afford the crude addition product which was taken to the next step without further purification or analysis.

PREPARATION OF INTERMEDIATES 43a & 43b

Intermediate 43a (n=3)

Intermediate 43b (n=2)

3-Benzyloxy-2-(2-ketoalkyl)dihydrocinnamonitrile Compounds

DMSO (3.0 eq) was slowly added to a solution of oxalyl chloride (1.5 eq) in methylene chloride at −78° C. and allowed to react for 2 h. A solution of the Grignard addition product of intermediate 42a or 42b (1.0 eq) in methylene chloride was slowly added and allowed to react for 2 h at −78° C. The reaction was quenched with triethylamine (4.0 eq) and allowed to warm to room temperature. The suspension was washed with 1N HCl and the solvent removed by rotary evaporation to afford the crude keto compound Intermediate 43a: ¹H NMR (CDCl₃) δ 7.37–7.05 (m, 6H), 7.09 (d, J=6.7, 1H), 6.86 (d, J=7.5, 1H), 5.00 (s, 2H), 3.71 (s, 2H), 2.84 (t, J=7.6 Hz, 2H), 2.79 (m, 6H), 2.48 (t, J=7.6 Hz, 2H).

Intermediate 43b: ¹H NMR (CDCl₃) δ 7.39–7.16 (m, 6H), 7.07 (d, J=6.7, 1H), 6.87 (d, J=7.5, 1H), 5.02 (s, 2H), 3.75 (s, 2H), 2.87 (t, J=7.6 Hz, 2H), 2.79 (m, 4H), 2.51 (t, J=7.6 Hz, 2H).

PREPARATION OF INTERMEDIATES 44a & 44b

Intermediate 44a (n=3)

Intermediate 44b (n=2)

3-(2-Alkylbenzofuran-4-yl)propionitrile Compounds

The respective crude keto compound of intermediates 43a and 43b were dissolved in EtOAc and hydrogenated in a Parr shaker at 50 psi with 10% Pd on carbon (10% weight percent) until TLC analysis indicated the reaction was complete. The suspension was filtered and the solvent removed by rotary evaporation to afford crude intermediates 44a and 44b, respectively. The crude intermediates 44a and 44b were not isolated for analysis and taken onto the next step without further purification.

PREPARATION OF INTERMEDIATES 45a & 45b

Intermediate 45a (n=3)

Intermediate 45b (n=2)

3-(2-Alkylbenzofuran-4-yl)prop-1-ylamine Compounds

A solution of the respective crude 3-(2-alkylbenzofuran-4-yl)propionitrile compounds (1.0 eq) in THF was slowly added to a suspension of LAH (2.0 eq) in THF. The reaction proceeded at room temperature for 4 h when TLC analysis indicated the reaction was complete. The reaction was diluted with ether and quenched slowly with 1N NaOH (5 mL/g LAH). After stirring for 1 h, the suspension was filtered and the solvent removed by rotary evaporation to afford the respective crude intermediates 45a and 45b which were taken onto the next step without further purification or analysis to synthesize Examples 21 to 28 below.

PREPARATION OF INTERMEDIATES 4A & 4B

Intermediate 4A (X=F)

Ethyl 2-[(1Z,3E)-4-(4-Fluorophenyl)buta-1,3-dienyl]-2,3-dihydrobenzo[b]furan-4-carboxylate n-BuLi (26 mmol) was added to a suspension of (4-fluorobenzyl)triphenylphosphonium bromide (26 mmol) in THF(100 mL) at 0° C. The mixture was warmed to room temperature and stirred for 1 hour. The mixture was then cooled to 0° C. and intermediate 28 (13 mmol) in THF (50 mL) was added. The solution was warmed to room temperature and stirred for 2 hours. The reaction was quenched with H₂O and the solvent removed in vacuo. The reaction was partioned between H₂O and EtOAc and extracted (3×150 mL). The combined organic layers were washed with brine (150 mL), dried over MgSO₄ and concentrated. The crude compound was purified by silica gel chromatography (10% ethyl acetate/hexanes) to give intermediate 4A in 67% yield.

¹H NMR (300 MHz, CDCl₃) δ 9.95–9.92 (m, 1H), 7.60–6.36 (m, 12H), 4.49–4.41 (m, 2H), 1.49–1.43 (m, 3H).

PREPARATION OF INTERMEDIATES 5A & 5B

Intermediate 5A (X=F)

Ethyl 2-[4-(4-Fluorophenyl)butyl]-2,3-dihydrobenzo [b]furan-4-carboxylate

Pd/C (500 mg) was added to a solution of intermediate 4A (8.6 mmol) in EtOAc (200 ml) and hydrogenated for 16 hours. The solution was filtered through Celite and concentrated under reduced pressure to give intermediate 5A in 83% yield.

¹H NMR (300 MHz, CDCl₃) δ 7.93 (d, J=7.8 Hz, 1H), 7.57 (d, J=8.0 Hz, 1H), 7.23 (t, J=7.8 Hz, 1H) 7.13 (m, 2H), 4.44 (q, J=7.11 Hz, 2H), 2.86–2.31 (m, 2H), 2.67–2.61 (m, 2H), 1.84–1.70 (m, 4H), 1.45 (t, J=7.1 Hz, 3H).

Intermediate 5B (X=H)

Intermediate 5B is also intermediate 22 above.

PREPARATION OF INTERMEDIATES 6A & 6B

Intermediate 6A (X=F)

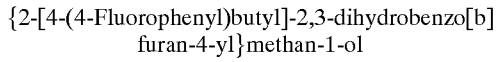
{2-[4-(4-Fluorophenyl)butyl]-2,3-dihydrobenzo[b]furan-4-yl}methan-1-ol Intermediate 5A (7 mmol) in THF (25 ml) was added to a suspension of LAH (14 mmol) in THF (75 ml). The suspension was stirred at room temperature for 16 h. The reaction was then quenched using the Fieser method, filtered through Celite, and the solvent removed in vacuo. The reaction was partitioned between EtOAc and $H_2O$ and extracted with EtOAc (3×100 ml). The combined organic layers were dried over $MgSO_4$, filtered and concentrated under reduced pressure to give intermediate 6A in quatitative yield.

$^1$H NMR (300 MHz, $CDCl_3$) δ 7.38–6.93 (m, 7H), 6.52 (s, 1H), 4.89 (s, 2H), 2.83–2.78 (m, 2H), 2.66–2.59 (m, 2H), 1.85–1.24 (m, 4H).

Intermediate 6B (X=H)

Intermediate 6B is also intermediate 23 above.

PREPARATION OF INTERMEDIATES 7A & 7B

Intermediate 7A (X=F)

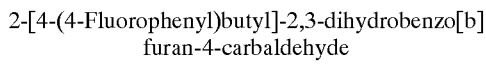
2-[4-(4-Fluorophenyl)butyl]-2,3-dihydrobenzo[b]furan-4-carbaldehyde

DMSO (3 mmol) was added to a solution of oxalyl chloride (15 mmol) in $CH_2Cl_2$ (80 ml) at −78° C. The solution was stirred at −78° C. for 30 minutes. Intermediate 6A (9.7 mmol) in $CH_2Cl_2$ (20 ml) was added dropwise via addition funnel and the resulting mixture allowed to stir at −78° C. for 1 hour. The reaction was quenched with $Et_3N$ (38.8 mmol) and allowed to warm to RT. The solution was then washed with brine (3×150 ml), the organic phase dried over $MgSO_4$, filtered, and concentrated under reduced pressure to give intermediate 7A in 64% yield.

$^1$H NMR (300 MHz, $CDCl_3$) δ 10.18 (s, 1H), 7.70–7.64 (m, 2H), 7.39–7.34 (m, 1H), 7.16–7.10 (m, 2H), 6.99–6.93 (m, 2H), 2.88–2.83 (m, 2H), 2.67–2.62 (m, 2H), 1.85–1.72 (m, 4H).

Intermediate 7B (X=H)

Intermediate 7B is also intermediate 24 above.

PREPARATION OF INTERMEDIATES 8A & 8B

Intermediate 8A (X=F)

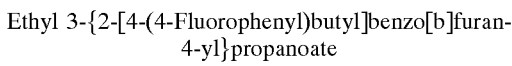
Ethyl 3-{2-[4-(4-Fluorophenyl)butyl]benzo[b]furan-4-yl}propanoate

A solution of intermediate 7A (1.5 g, 5 mmol) and $Ph_3PCHCO_2Et$ (3.48 g, 10 mmol) in THF (200 mL) was refluxed for 24. After THF was removed in vacuo, the crude product was purified by flash chromatography over silica gel (elution with 5% ethyl acetate in hexanes) to give 1.13 g (59%) of the desired product 8A as an oil. No analysis was obtained.

Intermediate 8B (X=H)

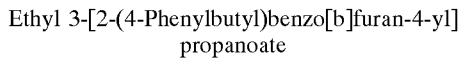
Ethyl 3-[2-(4-Phenylbutyl)benzo[b]furan-4-yl]propanoate

A solution of intermediate 7B (6.5 g, 23.4 mmol) and $Ph_3PCHCO_2Et$ (16.28 g, 46.8 mmol) in THF (200 mL) was refluxed for 24. After THF was removed in vacuo, the crude product was purified by flash chromatography over silica gel (elution with 5% ethyl acetate/hexanes) to give 8.1 g (99%) of the desired product as an oil.

$^1$H NMR (300 MHz, $CDCl_3$) δ 7.97 (d, J=16 Hz, 1H), 7.44–7.20 (m, 8H), 6.66 (d, J=0.8 Hz, 1H), 6.56 (d, J=16 Hz, 1H), 4.32 (q, J=7.1 Hz, 2H), 2.8 (t, J=6.7 Hz, 2H), 2.68 (t, J=7.4 Hz, 2H), 1.87–1.76 (m, 4H), 1.33 (t, J=6.7 Hz, 3H).

PREPARATION OF INTERMEDIATES 9A & 9B

Intermediate 9A (X=F)

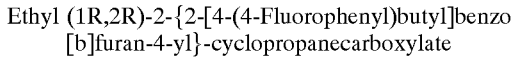
Ethyl (1R,2R)-2-{2-[4-(4-Fluorophenyl)butyl]benzo[b]furan-4-yl}-cyclopropanecarboxylate A solution of $CH_2N_2$ in ether, generated from 1-methyl-3-nitro-1-nitrosoguanidine (4.776 g), and 10 N NaOH (12 mL) in ether, was added to a solution of intermediate 8A (1.098 g, 3 mmol), and $Pd(OAc)_2$ (104 mg) in THF at 0° C. The resulting mixture was stirred for 2 h. After filtration, the filtrate was concentrated in vacuo to give a residue. The residue was purified by flash chromatography over silica gel (elution with 5% ethyl acetate/hexanes) gave 684 mg (60%) of the desired product as an oil.

$^1$H NMR (300 MHz, $CDCl_3$) δ 7.29 (d, J=6.9 Hz, 1H), 7.26–7.10 (m, 3H), 6.99–6.96 (m, 2H), 6.82 (d, J=7.5 Hz, 1H), 6.48 (d, J=0.6 Hz, 1H), 4.24 (q, J=7.1 Hz, 2H), 2.82–2.62 (m, 5H), 2.03–2.00 (m, 1H), 1.79–1.65 (m, 5H), 1.44–1.37 (m, 1H), 1.30 (t, J=7.1 Hz, 3H).

Intermediate 9B (X=H)

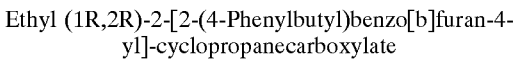
Ethyl (1R,2R)-2-[2-(4-Phenylbutyl)benzo[b]furan-4-yl]-cyclopropanecarboxylate A solution of $CH_2N_2$ in ether, generated from 1-methyl-3-nitro-1nitrosoguanidine (28.6 g) and 10 N NaOH (72 mL) in ether (200 mL) was added to a solution of intermediate 8B (6.264 g, 18 mmol) and $Pd(OAc)_2$ (626 mg) in THF (200 mL) at 0° C. The resulting mixture was stirred for 2 h. After filtration, the filtrate was concentrated in vacuo to give a residue. The residue was purified by flash chromatography over silica gel (elution with 5% ethyl acetate/hexanes) to give 5.21 g (80%) of intermediate 9B as an oil.

$^1$H NMR (300 MHz, $CDCl_3$) δ 7.31–7.08 (m, 7H), 6.79 (d, J=6.8 Hz, 1H), 6.47 (d, J=0.9 Hz, 1H), 4.24 (q, J=7.1 Hz, 2H), 2.82–2.65 (m, 5H), 2.04–1.98 (m, 1H), 1.82–1.59 (m, 5H), 1.44–1.37 (m, 1H), 1.30 (t, J=7.1 Hz, 3H).

PREPARATION OF INTERMEDIATES 10A & 10B

Intermediate 10A (X=F)

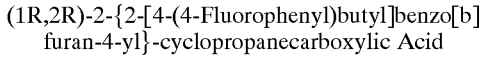
(1R,2R)-2-{2-[4-(4-Fluorophenyl)butyl]benzo[b]furan-4-yl}-cyclopropanecarboxylic Acid A mixture of intermediate 9A (670 mg, 1.76 mmol) and NaOH (141 mg, 3.52 mmol) in MeOH (40 mL) and water (20 mL) was refluxed for 1 h. After cooling to room temperature, concentration in vacuo gave 600 mg (97%) of the desired acid as an oil that was used without purification in the next step.

$^1$H NMR (300 MHz, $CDCl_3$) δ 7.31 (d, J=8.1 Hz, 1H), 7.16–7.12 (m, 3H), 6.99–6.93 (m, 2H), 6.85 (d, J=7.5 Hz, 1H), 6.48 (s, 1H), 2.83–2.62 (m, 5H), 2.03–2.00 (m, 1H), 1.79–1.65 (m, 5H), 1.53–1.47 (m, 1H).

Intermediate 10B (X=H)

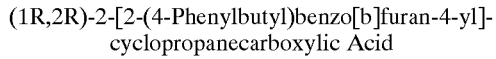
(1R,2R)-2-[2-(4-Phenylbutyl)benzo[b]furan-4-yl]-cyclopropanecarboxylic Acid A mixture of intermediate 9B (3.62 g, 10 mmol) and NaOH (800 mg, 20 mmol) in MeOH (40 mL) and water (20 mL) was refluxed for 1 h. After cooling to room temperature and concentrating in vacuo, the residue was acidified and extracted with EtOAc. The organic layer was washed with brine, dried over MgSO$_4$, filtered, and concentrated in vacuo to give 3.3 g (99%) of the desired acid as an oil that was used without purification in the next step.

$^1$H NMR (300 MHz, CDCl$_3$) δ 7.44–7.07 (m, 7H), 6.84 (d, J=7.5 Hz, 1H), 6.49 (d, J=0.8 Hz, 1H), 2.82–2.65 (m, 5H), 2.05–1.99 (m, 1H), 1.87–1.68 (m, 5H), 1.55–1.49 (m, 1H).

PREPARATION OF INTERMEDIATES 11A & 11B

Intermediate 11A (X=F)

(1R,2R)-2-{2-[4-(4-Fluorophenyl)butyl]benzo[b]furan-4yl}-cyclopropanecarboxamide A mixture of intermediate 10A (580 mg, 1.65 mmol) and thionyl chloride (20 mL) in CH$_2$Cl$_2$ was refluxed for 3 h. After cooling, the solvents were removed in vacuo to give the crude acid chloride. The acid chloride was dissolved in THF (50 mL) and cooled to −78° C. 5 mL of liquid NH$_3$ was introduced into the mixture. The resulting mixture was warmed to 0° C. and stirred for 16 h. The reaction was quenched with water and THF was removed in vacuo to give a residue. The residue was extracted with EtOAc. The organic layer was washed with brine, dried over MgSO$_4$, filtered, and concentrated in vacuo to give 570 mg (98%) of the desired amide as an oil that was used without purification in the next step.

$^1$H NMR (300 MHz, CDCl$_3$) δ 7.32–7.26 (m, 1H), 7.16–7.12 (m, 3H), 6.99–6.93 (m, 2H), 6.79 (d, J=7.5 Hz, 1H), 6.50 (s, 1H), 5.68 (s, 1H), 5.66 (s, 1H), 2.84–2.66 (m, 5H), 1.81–1.63 (m, 6H), 1.45–1.42 (m, 1H).

Intermediate 11 B (X=H)

(1R,2R)-2-[2-(4-Phenylbutyl)benzo[b]furan-4-yl]-cyclopropanecarboxamide

A mixture of intermediate 10B (3.206 g, 9.6 mmol) and thionyl chloride (15 mL) in CH$_2$Cl$_2$ (20 mL) was refluxed for 3 h. After cooling, the solvents were removed in vacuo to give the crude acid chloride. The acid chloride was dissolved in THF (50 mL) and cooled to −78° C. 5 mL of liquid NH$_3$ was introduced into the mixture. The resulting mixture was warmed to 0° C. and stirred for 16 h. The reaction was quenched with water and THF was removed in vacuo to give a residue. The residue was extracted with EtOAc. The organic layer was washed with brine, dried over MgSO$_4$, filtered, and concentrated in vacuo to give 2.84 g (89%) of the desired amide as an oil that was used without purification in the next step.

$^1$H NMR (300 MHz, CDCl$_3$) δ 7.31–7.08 (m, 7H), 6.78 (d, J=7.5 Hz, 1H), 6.48 (d, J=0.8 Hz, 1H), 5.82 (s, 1H), 5.73 (s, 1H), 2.85–2.64 (m, 5H), 1.84–1.62 (m, 6H), 1.43–1.26 (m, 1H).

PREPARATION OF INTERMEDIATES 12A & 12B

Intermediate 12A (X=F)

((1R,2R)-2-{2-[4-(4-Fluorophenyl)butyl]benzo[b]furan-4-yl}-cyclopropyl)methylamine Red-Al (1.6 mL, 8.18 mmol) was added to a suspension of intermediate 11A (580 mg, 1.65 mmol) in toluene (34 mL) at 0° C. The resulting mixture was warmed to room temperature and stirred for 16 h. After cooling to 0° C., the reaction was quenched with 10 N NaOH (17 mL) and diluted with EtOAc. The organic layer was washed with brine, dried over MgSO$_4$, filtered, and concentrated in vacuo to give 450 mg (83%) of the desired product as an oil that was used without purification in the next step. No analysis was undertaken.

Intermediate 12B (X=H)

{(1R,2R)-2-[2-(4-Phenylbutyl)benzo[b]furan-4-yl]cyclopropyl}methylamine

Red-Al (8.5 mL, 43.6 mmol) was added to a suspension of intermediate 11B (2.83 g, 8.5 mmol) in toluene (34 mL) at 0° C. The resulting mixture was warmed to room temperature and stirred for 16 h. After cooling to 0° C., the reaction was quenched with 10 N NaOH (17 mL) and diluted with EtOAc. The organic layer was washed with brine, dried over MgSO$_4$, filtered, and concentrated in vacuo to give 2.4 g (88%) of the desired product as an oil that was used without purification in the next step. No analysis was undertaken.

PREPARATION OF INTERMEDIATE 3A'

(3S)-5-(Methoxymethoxy)-3-prop-2-enylisochroman-1-one

BH$_3$.THF (60 mL, 60 mmol) was added to a solution of 2,3-dimethyl-2-butene (60 mL, 60 mmol) in THF (300 mL) at 0° C. The resulting solution was warmed to room temperature and stirred for 0.5 h. After cooling to −15° C., a solution of intermediate 5 (14.88 g, 60 mmol) in THF (20 mL) was added and the mixture was stirred for 1 h. The reaction was sequentially quenched with water (18 mL), 20% NaOH (18 mL), and 30% H$_2$O$_2$ (18 mL) and then stirred for 1 h at 0° C. After THF was removed, the residue was extracted with EtOAc. The organic layer was washed with brine, dried over MgSO$_4$, and concentrated in vacuo to give a residue. The residue was purified by flash chromatography over silica gel (elution with 50% ethyl acetate/hexanes) to give 12 g (75%) of the desired product as a solid.

$^1$H NMR (300 MHz, CDCl$_3$) δ 7.77–7.72 (m, 1H), 7.34–7.26 (m, 2H), 5.22 (s, 2H), 4.58–4.49 (m, 1H), 3.75–3.72 (m, 2H), 3.48 (s, 3H), 3.18 (dd, J=16.9, 3.2 Hz, 1H), 2.72 (dd, J=16.9, 11.7 Hz, 1H), 2.01–1.75 (m, 4H); $[α]^{25}_D$+75° (MeOH); m.p. 74–75° C.

PREPARATION OF INTERMEDIATE 4A'

3-[(3S)-5-(Methoxymethoxy)-1-oxoisochroman-3-yl]propanal

DMSO (6 mL, 84 mmol) was added to a solution of oxalyl chloride (33.6 mL, 67.2 mmol) in CH$_2$Cl$_2$ (42 mL) at −78° C. under N$_2$ and the resulting mixture was stirred for 1 h. A solution of intermediate 3A' (11.172 g, 42 mmol) in CH$_2$Cl$_2$ (20 mL) was added dropwise. After stirring for 1 h, the reaction was quenched with Et$_3$N (23.35 mL, 168 mmol), allowed to warm to room temperature and stirred for 1 h. The reaction was quenched with water. The organic layer was washed with brine, dried over MgSO$_4$, and concentrated in vacuo to give a residue. The residue was purified by flash chromatography over silica gel (elution with 50% ethyl acetate/hexanes) to give 9.98 g (90%) of the desired product as an oil.

$^1$H NMR (300 MHz, CDCl$_3$) δ 9.86 (s, 1H), 7.77–7.72 (m, 1H), 7.35–7.26 (m, 2H), 5.22 (s, 2H), 4.58–4.49 (m, 1H), 3.75–3.72 (m, 2H), 3.50 (s, 3H), 3.20 (dd, J=16.9, 3.4 Hz, 1H), 2.83 (t, J=6.9 Hz, 2H), 2.72 (dd, J=16.9, 11.7 Hz, 1H), 2.21–2.03 (m, 4H); $[\alpha]^{25}_D$+71° (MeOH).

PREPARATION OF INTERMEDIATE 5A'

3-((3E)-4-Phenylbut-3-enyl)(3S)-5-(methoxymethoxy)isochroman-1-one n-BuLi (52.5 mL, 36.8 mmol) was added dropwise to a suspension of Ph$_3$PCH$_2$Br (40 g, 92.4 mmol) in THF (368 mL) at 0° C. under N$_2$. After stirring for 1 h, a solution of intermediate 4A' (9.90 g, 37.8 mmol) in THF (20 mL) was added. The resulting mixture was allowed to warm to room temperature and stirred for 1 h. The reaction was quenched with water, and THF was removed in vacuo to give a residue. The residue was extracted with EtOAc. The organic layer was washed with brine, dried over MgSO$_4$, and concentrated in vacuo to give a residue. The residue was purified by flash chromatography over silica gel (elution with 25% ethyl acetate/hexanes) to give 11 g (86%) of the desired product as a mixture of isomers.

$^1$H NMR (300 MHz, CDCl$_3$) δ 7.80–7.76 (m, 1H), 7.38–7.17 (m, 7H), 6.50–6.45 (m, 1H), 6.27–6.18 (m, 0.6H), 5.71–5.63 (m, 0.4H), 5.22 (s, 1.2H), 5.21 (s, 0.8H), 4.59–4.48 (m, 1H), 3.50 (s, 1.8H), 1.2 (s, 1.2H), 3.23–3.10 (m, 1H), 2.79–2.46 (m, 3H), 2.14–1.85 (m, 2H).

PREPARATION OF INTERMEDIATE 6A'

(3S)-5-(Methoxymethoxy)-3-(4-phenylbutyl)isochroman-1-one

A suspension of intermediate 5A' (11 g, 32.54 mmol) and 10% Pd/C (1100 mg) in EtOAc (100 mL) was hydrogenated at 60 psi overnight. After filtration to remove the catalyst and washing with EtOAc, the filtrate was concentrated in vacuo to give 11 g (99%) of the desired product as an oil which was used without purification in the next step.

$^1$H NMR (300 MHz, CDCl$_3$) δ 7.78–7.72 (m, 1H), 7.32–7.14 (m, 7H), 5.21 (s, 2H), 4.50–4.41 (m, 1H), 3.46 (s, 3H), 3.10 (dd, J=16.9, 3.2 Hz, 1H), 2.72–2.6 (m, 3H), 1.94–1.51 (m, 6H); $[\alpha]^{25}_D$+51° (MeOH).

PREPARATION OF INTERMEDIATE 7A'

(3S)-5-(Methoxymethoxy)-3-(4-phenylbutyl)isochroman-1-ol

DIBAL-H (35.59 mL, 35.59 mmol) was added to a solution of intermediate 6A' (11 g, 32.45 mmol) in toluene (224 mL) at −78° C. After stirring for 1 h, the reaction was quenched with 4 N NaOH (20 mL). After warming to room temperature, the reaction mixture was diluted with EtOAc. The organic layer was dried over MgSO$_4$ and concentrated in vacuo to give 11 g (99%) of the desired product as an oil which was used without purification in the next step.

$^1$H NMR (300 MHz, CDCl$_3$) δ 7.30–6.82 (m, 8H), 6.15 (s, 1H), 5.20–5.15 (m, 1H), 4.28–4.22 (m, 1H), 3.45 (m, 3H), 2.87–2.63 (m, 3H), 2.45–2.37 (m, 1H), 1.88–1.42 (m, 7H).

PREPARATION OF INTERMEDIATE 8A'

Ethyl (2E)-3-[2-((2S)-2-hydroxy-6-Phenylhexyl)-3-(methoxymethoxy)phephenyl]prop-2-enoate A solution of intermediate 7A' (11 g, 32.3 mmol) and Ph$_3$PCHCO$_2$Et (22.5 g, 64.6 mmol) in THF (200 mL) was stirred until the reaction was complete. After THF was removed in vacuo, the crude product was purified by flash chromatography over silica gel (elution with 25% ethyl acetate/hexanes) to give 13 g (98%) of intermediate 8A' as an oil that was taken onto the next step without analysis.

PREPARATION OF INTERMEDIATE 9A'

Ethyl (2E)-3-[2-((2S)-2-Hydroxy-6-Phenylhexyl)-3-hydroxyphenyl]-prop-2-enoate

A solution of intermediate 8A' (12.8 g, 31.07 mmol) in 2.5% concentrated HCl in EtOH (200 mL) was stirred until the reaction was complete. The reaction was quenched with NaHCO$_3$ solution and EtOH was removed in vacuo. The residue was extracted with EtOAc. The organic layer was washed with brine, dried over MgSO$_4$, and concentrated in vacuo to give a residue. The residue was purified by flash chromatography over silica gel (elution with 25% ethyl acetate/hexanes) to give 11.4 g (100%) of intermediate 9A' as an oil that was taken onto the next step without analysis.

PREPARATION OF INTERMEDIATE 10A'

Ethyl (2E)-3-[(2R)-2-(4-Phenylbutyl)(2,3-dihydrobenzo[b]furan-4-yl]-prop-2-enoate A solution of DEAD (7.28 g, 36 mmol) in THF (10 mL) was added dropwise to a solution of intermediate 9A' (11 g, 29.89 mmol) and Ph$_3$P (9.44 g, 36 mmol) in THF (200 mL) at 0° C. The resulting mixture was warmed to room temperature and stirred for 16 h. The THF was removed in vacuo to give a residue which was purified by flash chromatography over silica gel (elution with 10% ethyl acetate/hexanes) to give 10 g (95%) of intermediate 10A' as an oil.

$^1$H NMR (300 MHz, CDCl$_3$) δ 7.76 (d, J=16 Hz, 1H), 7.30–7.01 (m, 7H), 6.76 (d, J=7.7 Hz, 1H), 6.36 (d, J=16 Hz, 1H), 4.85–4.75 (m, 1H), 4.24 (q, J=7.0 Hz, 2H), 3.39 (dd, J=15.9, 9.0 Hz, 1H), 2.95 (dd, J=15.9, 7.6 Hz, 1H), 2.64 (t, J=7.3 Hz, 2H), 1.89–1.47 (m, 6H), 1.33 (t, J=7.0 Hz, 3H); $[\alpha]^{25}_D$+88° (MeOH).

PREPARATION OF INTERMEDIATE 11A'

(2E)-3-[(2R)-2-(4-Phenylbutyl)(2,3-dihydrobenzo[b]furan-4-yl)]-prop-2-enoic Acid A mixture of intermediate 10A' (9.88 g, 38 mmol) and NaOH (3040 mg, 76 mmol) in MeOH (76 mL) and water (638 mL) was refluxed for 1 h. After cooling to room temperature, the MeOH was removed in vacuo. The remaining mixture was acidified with 4 N HCl and extracted with EtOAc. The combined organic phases were washed with brine, dried over MgSO$_4$, and concentrated in vacuo to give 8.8 g (96%) of the desired product as a solid which was used without purification in the next step. No analysis was undertaken.

PREPARATION OF INTERMEDIATE 12A'

4-{(2E)-3-[(2R)-2-(4-Phenylbutyl)(2,3-dihydrobenzo[b]furan-4-yl)]prop-2-enoyl}-4-aza-10,10-dimethyl-3-thiatricyclo[5.2.1.0<1,5>]-decane-3,3-dione A mixture of intermediate 11A' (8.8 g, 38 mmol) and thionyl chloride (57 mL) in CH$_2$Cl$_2$ (76 mL) was refluxed for 3 h. After cooling, the solvents were removed in vacuo to give the crude acid chloride. NaH (1.824 g, 45.6 mmol) was added to a solution of (S)-camphorsultam (9.0 g, 41.8 mmol) in toluene (100 mL) at 0° C. After warming to room temperature, the mixture was stirred for 1 h. After recooling to 0° C., a solution of the acid chloride in toluene (10 mL) was added to the mixture. The resulting mixture was allowed to warm to room temperature and stirred over night. The reaction was quenched with water and diluted with EtOAc. The organic layer was separated, washed with brine, dried over $MgSO_4$, and concentrated in vacuo to give a residue. The residue was purified by flash chromatography over silica gel (elution with 20% ethyl acetate/hexanes) to give 13 g (92%) of the title compound as an oil.

$^1$H NMR (300 MHz, $CDCl_3$) δ 7.76 (d, J=15.5 Hz, 1H), 7.30–7.05 (m, 8H), 6.48 (dd, J=7.4, 1.0 Hz, 1H), 4.85–4.75 (m, 1H), 3.97 (dd, J=7.4, 5.1 Hz, 1H), 3.69 (q, J=7.0 Hz, 1H), 3.55–3.38 (m, 3H), 2.96 (dd, J=16, 7.5 Hz, 1H), 2.60 (t, J=7.3 Hz, 2H), 2.22–1.20 (m, 10H), 1.19 (s, 3H), 0.98 (s, 3H); $[\alpha]^{25}_D$–13° (MeOH).

PREPARATION OF INTERMEDIATE 13A'

4-({2-[(2R)-2-(4-Phenylbutyl)(2,3-dihydrobenzo[b] furan-4-yl)]-(1S,2R)cyclopropyl}carbonyl)-4-aza-10,10-dimethyl-3-thiatricyclo[5.2.1.0<1.5>]decane-3,3-dione To a mixture of 10 N NaOH (96 mL) and ether (320 mL) at 0° C. was added 1-methyl-3-nitro-1-nitrosoguanidine (38.21 g, 260 mmol) in portions over 0.5 h. The mixture was shaken for 15 min and the ether layer carefully decanted into a solution of intermediate 12A' (13 g, 25 mmol) and $Pd(OAc)_2$ (500 mg) in $CH_2Cl_2$ (320 mL) at 0° C. The resulting mixture was stirred for 2 h. After filtration, the filtrate was concentrated in vacuo to give a residue. The residue was purified by flash chromatography over silica gel (elution with 20% ethyl acetate/hexanes) to give 10 g (76%) of the desired product as an oil.

$^1$H NMR (300 MHz, $CDCl_3$) δ 7.29–7.14 (m, 3H), 7.01 (d, J=7.8 Hz, 1H), 6.62 (d, J=7.8 Hz, 1H), 6.51 (d, J=7.8 Hz, 1H), 4.81–4.71 (m, 1H), 3.91 (dd, J=7.5, 5.0 Hz, 1H), 3.48 (q, J=13.7 Hz, 2H), 3.34 (dd, J=15.5, 6.5 Hz, 1H), 2.78 (dd, J=15.5, 7.8 Hz; 1H), 2.65–2.45 (m, 4H), 2.16–1.30 (m, 13H), 1.19 (s, 3H), 0.98 (s, 3H); $[\alpha]^{25}_d$–37° (MeOH).

PREPARATION OF INTERMEDIATE 14A'

{2-[(2R)-2-(4-Phenylbutyl)(2,3-dihydrobenzo[b] furan-4-yl)]-(2S,1R)cyclopropyl}methan-1-ol A solution of intermediate 13A' (4 g, 7.65 mmol) in THF (20 mL) was added to a suspension of $LiAlH_4$ (1.162 g, 30.6 mmol) in THF (100 mL) at –45° C. The resulting mixture was allowed to warm to room temperature and stirred for 0.5 h. After cooling to –45° C., the reaction was quenched with saturated $KHSO_4$ solution. After warming to room temperature, the insolubles were removed by filtration and washed with THF. The filtrate was concentrated in vacuo to give a residue. The residue was purified by flash chromatography over silica gel (elution with 10% ethyl acetate/hexanes) to give 2.3 g (93%) of the desired product as an oil.

$^1$H NMR (300 MHz, $CDCl_3$) δ 7.29–7.14 (m, 3H), 7.01 (d, J=7.8 Hz, 1H), 6.57 (d, J=7.8 Hz, 1H), 6.35 (d, J=7.8 Hz, 1H), 4.82–4.72 (m, 1H), 3.30 (dd, J=6.6, 1.8, Hz, 2H), 3.11 (dd, J=15.4, 6.4 Hz, 1H), 2.83 (dd, J=15.5, 7.8 Hz, 1H), 2.63 (t, J=7.4 Hz, 2H), 1.94–1.44 (m, 8H), 0.98–0.87 (m, 2H); $[\alpha]^{25}_D$=19° (MeOH).

PREPARATION OF INTERMEDIATE 15A'

2-[(2R)-2-(4-Phenylbutyl)(2,3-dihydrobenzo[b] furan-4-yl)]-2S,1R)cyclopropanecarbaldehyde DMSO (0.99 mL, 14 mmol) was added to a solution of oxalyl chloride (5.6 mL, 11.2 mmol) in $CH_2Cl_2$ (14 mL) at –78° C. under $N_2$ and the resulting mixture was stirred for 1 h. A solution of intermediate 14A' (2.268 g, 7 mmol) in $CH_2Cl_2$ (12 mL) was added dropwise. After stirring for 1 h, the reaction was quenched with $Et_3N$ (3.9 mL, 28 mmol), allowed to warm to room temperature, and stirred for 1 h. The reaction was quenched with water. The organic layer was washed with brine, dried over $MgSO_4$, and concentrated in vacuo to give a residue. The residue was purified by flash chromatography over silica gel (elution with 20% ethyl acetate/hexanes) to give 2.24 g (98%) of the desired product as an oil.

$^1$H NMR (300 MHz, $CDCl_3$) δ 9.35 (d, J=4.5 Hz, 1H), 7.48–7.09 (m, 3H), 7.01 (d, J=8 Hz, 1H), 6.62 (d, J=8 Hz, 1H), 6.42 (d, J=8 Hz, 1H), 4.83–4.73 (m, 1H), 3.24 (dd, J=15.5, 8.9, Hz, 1H), 2.83 (dd, J=15.5, 7.8 Hz, 1H), 2.63 (t, J=7.3 Hz, 2H), 2.50–2.46 (m, 1H), 2.15–2.12 (m, 1H), 1.87–1.23 (m, 8H); $[\alpha]^{25}_D$+21° (MeOH).

PREPARATION OF INTERMEDIATE 16A'

{2-[(2R)-2-(4-Phenylbutyl)(2,3-dihydrobenzo[b] furan-4-yl)]-2S,1R)cyclopropyl}(hydroxyimino) methane An aqueous NaOH solution (20.49 mL, 20.49 mmol) was added to a mixture of intermediate 15A' (2.28 g, 6.83 mmol) and $NH_2OH·HCl$ (1.424 g, 20.49 mmol) in THF (41 mL). The resulting mixture was refluxed for 1 h. After THF was removed, the residue was extracted with EtOAc, washed with brine, dried over $MgSO_4$, and concentrated in vacuo to give 2.23 g (98%) of the desired product which was used without purification in the next step.

$^1$H NMR (300 MHz, $CDCl_3$) δ 7.31–7.00 (m, 3H), 7.01 (d, J=8 Hz, 1H), 6.63–6.60 (m, 1H), 6.47–6.24 (m, 1H), 4.83–4.73 (m, 1H), 3.36–3.30 (m, 1H), 2.88–2.67 (m, 1H), 2.65 (t, J=7.3 Hz, 2H), 2.08–2.14 (m, 10H).

PREPARATION OF INTERMEDIATE 17A'

{2-[(2R)-2-(4-Phenylbutyl)(2,3-dihydrobenzo[b] furan-4-yl)]-2S,1R)cyclopropyl}methylamine A solution of intermediate 16A' (2.2 g, 6.52 mmol) in THF (20 mL) was added to a suspension of $LiAlH_4$ (368 mg, 9.75 mmol) in THF (240 mL) at 0° C. The resulting mixture was refluxed for 3 h. After cooling to room temperature, the reaction was quenched using the Fieser method. The insolubles were removed by filtration and washed with THF. The filtrate was concentrated in vacuo to give a residue which was extracted with EtOAc. The organic layer was dried over $MgSO_4$ and concentrated to give, 1.8 g (84%) of the desired product which was used without purification in the next step. No analysis was undertaken. Intermediate 17A' was used to prepare Examples 42 to 47.

EXAMPLE 1

N-[3-[2-(4-Phenylbutyl)-2,3-dihydrobenzofuran-4-yl]propyl]acetamide

To a solution of intermediate 17 (155 mg, 0.5 mmol) and $Et_3N$ (202 mg, 2 mmol) in $CH_2Cl_2$ (10 mL) was added a solution of acetyl chloride (78 mg, 1 mmol) in $CH_2Cl_2$ (2 mL). After stirring for 16 h, the reaction was quenched with water (5 mL) and diluted with $CH_2Cl_2$ (30 mL). The organic phase was separated, washed with brine, dried over $MgSO_4$, and concentrated in vacuo. The residue was purified by flash chromatography over silica gel (75% ethyl acetate/hexanes) to give 121 mg (69%) of the title compound as a solid.

¹H NMR (300 MHz, CDCl₃) δ 7.32–7.26 (m, 2H), 7.21–7.16 (m, 3H), 7.05 (t, J=7.8 Hz, 1H), 6.63 (t, J=7.3 Hz, 2H), 5.45 (br s, 1H), 4.81–4.71 (m, 1H), 3.30 (q, J=7.0 Hz, 2H), 3.20 (dd, J=15.3, 8.9 Hz, 1H), 2.75 (dd, J=15.3, 7.8 Hz, 1H), 2.65 (t, J=7.4 Hz, 2H), 2.55 (t, J=7.4 Hz, 2H), 2.10 (s, 3H), 2.00–1.47 (m, 8H); ¹³C NMR (75 MHz, CDCl₃) δ 170.2, 159.7, 142.6, 138.3, 128.6, 128.5, 128.3, 125.9, 125.6, 120.1, 107.2, 83.3, 39.7, 36.3, 36.0, 34.4, 31.6, 31.0, 29.9, 25.3, 23.5; IR (film, cm⁻¹) 3313, 1630, 1541; MS(SEI) 352 (M+H)⁺; $[\alpha]_D^{25}$+49 (MeOH); Anal. Calc'd. for $C_{23}H_{29}NO_2$: C, 78.60; H, 8.32; N, 3.98; Found: C, 78.24; H, 8.11; N, 3.83; m.p. 40–41° C.

EXAMPLE 2

N-[3-[2-(4-Phenylbutyl)-2,3-dihydrobenzofuran-4-yl]propyl]propionamide

The title compound was prepared by the general procedure described in Example 1 using intermediate 17 (155 mg, 0.5 mmol), Et₃N (202 mg, 2 mmol) and propionyl chloride (78 mg, 1 mmol). Purification by flash chromatography over silica gel (50% ethyl acetate/hexanes) gave 91 mg (50%) of the title compound as an oil.

¹H NMR (300 MHz, CDCl₃) δ 7.37–7.32 (m, 2H), 7.26–7.21 (m, 3H), 7.10 (t, J=7.8 Hz, 1H), 6.68 (t, J=8.1 Hz, 2H), 5.45 (br s, 1H), 4.86–4.76 (m, 1H), 3.39 (q, J=7.0 Hz, 2H), 3.29 (dd, J=15.3, 8.9 Hz, 1H), 2.80 (dd, J=15.4, 7.9 Hz, 1H), 2.70 (t, J=7.4 Hz, 2H), 2.61 (t, J=7.4 Hz, 2H), 2.21 (q, J=7.6 Hz, 2H), 2.19–1.52 (m, 8H), 1.18 (t, J=7.6 Hz, 3H); ¹³C NMR (75 MHz, CDCl₃) δ 173.6, 159.5, 142.4, 138.1, 128.3, 128.2, 128.1, 125.6, 125.4, 119.9, 107.0, 83.0, 39.3, 36.0, 35.8, 34.2, 31.3, 30.8, 29.7, 25.1, 9.8; IR (film, cm⁻¹) 3209, 1651, 1455; MS(SEI) 365 M⁺; $[\alpha]_D^{25}$+46 (MeOH); Anal. Calc'd. for $C_{24}H_{31}NO_2 \cdot 0.3H_2O$: C, 77.72; H, 8.59; N, 3.78; Found: C, 77.74; H, 8.50; N, 3.70.

EXAMPLE 3

N-[3-[2-(4-Phenylbutyl)-2,3-dihydrobenzofuran-4-yl]propyl]butyramide

The title compound was prepared by the general procedure described in Example 1 using intermediate 17 (155 mg, 0.5 mmol), Et₃N (202 mg, 2 mmol) and n-butyryl chloride (106 mg, 1 mmol). Purification by flash chromatography over silica gel (50% ethyl acetate/hexanes) gave 205 mg (60%) of the desired product as an oil.

¹H NMR (300 MHz, CDCl₃) δ 7.31–7.29 (m, 2H), 7.20–7.18 (m, 3H), 7.05 (t, J=7.8 Hz, 1H), 6.63 (t, J=7.7 Hz, 2H), 5.39 (br s, 1H), 4.80–4.71 (m, 1H), 3.31 (q, J=7.0 Hz, 2H), 3.20 (dd, J=15.3, 8.9 Hz, 1H), 2.75 (dd, J=15.3, 7.9 Hz, 1H), 2.66 (t, J=7.4 Hz, 2H), 2.56 (t, J=7.4 Hz, 2H), 2.11 (q, J=7.2 Hz, 2H), 2.19–1.52 (m, 10H), 1.18 (t, J=7.2 Hz, 3H); ¹³C NMR (75 MHz, CDCl₃) δ 173.1, 159.7, 142.6, 138.4, 128.6, 128.5, 128.3, 125.9, 125.6, 120.1, 107.2, 83.3, 39.5, 38.9, 36.3, 36.0, 34.4, 31.6, 31.1, 30.6, 25.4, 19.3, 13.9; IR (film, cm⁻¹) 3289, 1644, 1456; MS(SEI) 378 (M-H)⁺; $[\alpha]_D^{25}$+44 (c 0.35, MeOH); Anal. Calc'd. for $C_{25}H_{33}NO_2 \cdot 0.1H_2O$: C, 78.74; H, 8.78; N, 3.67; Found: C, 78.37; H, 8.60; N, 3.60.

EXAMPLE 4

N-[3-[2-(4-Phenylbutyl)-2,3-dihydrobenzofuran-4-yl]propyl]-2-methylpropionamide

The title compound was prepared by the general procedure described in Example 1 using intermediate 17 (155 mg, 0.5 mmol), Et₃N (202 mg, 2 mmol) and i-butyryl chloride (106 mg, 1 mmol). Purification by flash chromatography over silica gel (33% ethyl acetate/hexanes) gave 110 mg (61%) of the desired product as an oil.

¹H NMR (300 MHz, CDCl₃) δ 7.31–7.29 (m, 2H), 7.21–7.16 (m, 3H), 7.05 (t, J=7.8 Hz, 1H), 6.63 (t, J=8.9 Hz, 2H), 5.40 (br s, 1H), 4.80–4.70 (m, 1H), 3.31 (q, J=6.9 Hz, 2H), 3.20 (dd, J=15.3, 8.9 Hz, 1H), 2.75 (dd, J=15.3, 7.9 Hz, 1H), 2.66 (t, J=7.4 Hz, 2H), 2.56 (t, J=7.8 Hz, 2H), 2.27 (m, 1H), 2.24–1.52 (m, 8H), 1.08 (d, J=6.8 Hz, 6H); ¹³C NMR (75 MHz, CDCl₃) δ 173.1, 159.7, 142.6, 138.4, 128.6, 128.5, 128.3, 125.9, 125.6, 120.1, 107.2, 83.3, 39.5, 38.9, 36.3, 36.0, 34.4, 31.6, 31.1, 30.6, 25.4, 19.3, 13.9; IR (film, cm⁻¹) 3299, 1645, 1456; MS(SEI) 380 (M+H)⁺; $[\alpha]_D^{25}$+44 (c 0.57, MeOH); Anal. Calc'd. for $C_{25}H_{33}NO_2 \cdot 0.3H_2O$: C, 78.00; H, 8.80; N, 3.64; Found: C, 77.83; H, 8.74; N, 3.34.

EXAMPLE 5

N-[3-[2-(4-Phenylbutyl)-2,3-dihydrobenzofuran-4-yl]propyl]cyclopropanecarboxamide The title compound was prepared by the general procedure described in Example 1 using intermediate 17 (155 mg, 0.5 mmol), Et₃N (202 mg, 2 mmol) and cyclopropane carbonyl chloride (105 mg, 1 mmol). Purification by flash chromatography over silica gel (30% ethyl acetate/hexanes) gave 114 mg (60%) of the desired product as a solid.

¹H NMR (300 MHz, CDCl₃) δ 7.31–7.29 (m, 2H), 7.20–7.16 (m, 3H), 7.05 (t, J=7.8 Hz, 1H), 6.65 (d, J=7.5 Hz, H), 6.61 (d, J=7.9 Hz, 1H), 5.88 (br s, 1H), 4.81–4.71 (m, 1H), 3.31 (q, J=6.0 Hz, 2H), 3.20 (dd, J=15.3, 8.9 Hz, 1H), 2.75 (dd, J=15.4, 7.9 Hz, 1H), 2.66 (t, J=7.4 Hz, 2H), 2.56 (t, J=7.3 Hz, 2H), 1.89–1.49 (m, 8H), 1.28–1.22 (m, 1H), 0.98–0.93 (m, 1H), 0.75–0.65 (m, 2H); 13C NMR (75 MHz, CDCl₃) δ 173.6, 159.7, 142.6, 138.4, 128.6, 128.5, 128.3, 125.9, 125.6, 120.2, 107.2, 83.3, 39.8, 36.3, 36.0, 34.4, 31.6, 31.0, 25.4, 14.9, 7.2; IR (film, cm⁻¹) 3307 1631; MS(SEI) 378 (M+H)⁺; $[\alpha]_D^{25}$+46 (c 0.7, MeOH); Anal. Calc'd. for $C_{25}H_3NO_2$: C, 79.54; H, 8.28; N, 3.71; Found: C, 79.31; H, 8.22; N, 3.43; m.p. 63–64° C.

EXAMPLE 6

N-[3-[2-(4-Phenylbutyl)-2,3-dihydrobenzofuran-4-yl]propyl]-N-ethyl Urea

A solution of intermediate 17 (155 mg, 0.5 mmol) and ethyl isocyanate (71 mg, 1 mmol) in benzene (10 mL) was stirred for 16 h. The benzene was removed in vacuo and the residue purified by flash chromatography over silica gel (75% ethyl acetate/hexanes) to give 95 mg (50%) of the desired product.

¹H NMR (300 MHz, CDCl₃) δ 7.31–7.26 (m, 2H), 7.21–7.16 (m, 3H), 7.05 (t, J=7.7 Hz, 1H), 6.63 (t, J=7.6 Hz, 1H), 4.80–4.70 (m, 1H), 4.29 (brs, 2H), 3.34–3.12 (m, 5H), 2.75 (dd, J=15.3, 7.8 Hz, 1H), 2.65 (t, J=7.4 Hz, 2H), 2.57 (t, J=7.3 Hz, 2H), 1.95–1.51 (m, 8H), 1.46 (d, =7.9 Hz, 3H); ¹³C NMR (75 MHz, CDCl₃) δ 159.7, 158.2, 142.6, 138.5, 128.6, 128.5, 128.3, 125.9, 125.7, 120.2, 107.2, 83.3, 40.5, 36.3, 36.0, 35.6, 34.4, 31.6, 30.9, 30.5, 25.4, 15.6; IR (film, cm⁻¹) 3327, 1628, 1574; MS(SEI) 380 M+; $[\alpha]_D^{25}$+45 (c 0.9, MeOH); Anal. Calc'd. for $C_{24}H_{32}N_2O_2$: C, 75.75; H, 8.48; N, 7.36; Found: C, 75.68; H, 8.54; N, 7.05.

EXAMPLE 7

N-[3-[2-(4-Phenylbutyl)benzofuran-4-yl]propyl]cyclopropanecarboxamide

To a solution of intermediate 26 (614 mg, 2 mmol) and Et₃N (1.112 g, 8 mmol) in CH₂Cl₂ (20 mL) was added a solution of cyclopropanecarbonyl chloride (416 mg, 4 mmol) in $CH_2Cl_2$. After stirring for 4 h, the reaction was quenched with water and diluted with $CH_2Cl_2$. The organic layer was washed with brine, dried over $MgSO_4$, and concentrated in vacuo to give a crude product which was purified by flash chromatography over silica gel (elution with 30% ethyl acetate/hexanes) to give 522 mg (70%) of the desired title compound as a solid.

$^1$H NMR (300 MHz, $CDCl_3$) δ 7.30–7.09 (m, 7H), 6.96 (d, J=6.7 Hz, 1H), 6.36 (d, J=0.8 Hz, 1H), 5.63 (br s, 1H), 3.30 (q, J=6.0 Hz, 2H), 2.85–2.76 (m, 4H), 2.66 (t, J=7.4 Hz, 2H), 1.98 1.69 (m, 6H), 1.25–0.65 (m, 5H); $^{13}$C NMR (75 MHz, $CDCl_3$) δ 173.5, 159.0, 154.5, 142.2, 133.6, 128.4, 128.3, 128.0, 125.7, 123.1, 121.8, 108.6, 100.2, 39.5, 35.6, 31.0, 30.9, 30.7, 30.3, 28.3, 27.3, 14.7, 7.01; IR (film, $cm^{-1}$) 3237 (br), 1634; MS(SEI) 376 $(M+H)^+$; Anal. Calc'd. for $C_{25}H_{29}NO_2 \cdot 0.1H_2O$: C, 79.58; H, 7.80; N, 3.71; Found: C, 79.29; H, 8.05; N, 3.59; m.p. 70–71° C.

EXAMPLE 8

N-[3-[2-(4-Phenylbutyl)benzofuran-4-yl]propyl]-N-ethyl Urea

A solution of intermediate 26 (307 mg, 1 mmol) and ethyl isocyanate (142 mg, 2 mmol) in benzene (10 mL) was stirred for 16 h. The benzene was removed in vacuo, and the residue was purified by flash chromatography over silica gel (elution with 50% ethyl acetate/hexanes) to give 283 mg (75%) of the title compound.

$^1$H NMR (300 MHz, $CDCl_3$) δ 7.31–7.07 (m, 7H), 6.96 (d, J=7.3, Hz, 1H), 6.35 (d, J=0.8 Hz, 1H), 4.47 (br s, 1H), 3.19 (t, J=6.9 Hz, 2H), 3.10 (q, J=7.2 Hz, 2H), 2.83–2.74 (m, 4H), 2.64 (t, J=7.4 Hz, 2H), 1.96–1.66 (m, 6H), 1.04 (t, J=7.2 Hz, 3H); $^{13}$C NMR (75 MHz, $CDCl_3$) δ 159.1, 158.4, 154.6, 142.3, 133.8, 128.5, 128.4, 128.2, 125.8, 123.2, 121.9, 108.7, 100.4, 40.9, 35.7, 35.3, 30.9, 30.7, 28.4, 27.4, 15.5; IR (film, $cm^{-1}$) 3294 (br), 1642; MS(SEI) 379 $(M+H)^+$; Anal. Calc'd. for $C_{24}H_{30}N_2O_2 \cdot 0.1H_2O$: C, 75.80; H, 8.00; N, 7.37; Found: C, 75.31; H, 8.07; N, 7.00.

EXAMPLE 9

N-[3-[2-(4-Phenylbutyl)benzofuran-4-yl]propyl] acetamide

A suspension of intermediate 25 (662 mg, 2 mmol) and acetic anhydride (1 mL), and Raney Nickel (1 mL) in THF (20 mL) was hydrogenated at 50 psi for 16 h. After filtration and washing with THF, the filtrate was concentrated in vacuo to give a residue. The residue was purified by flash chromatography over silica gel (elution with 75% ethyl acetate/hexanes) to give 555 mg (80%) of the title compound as an oil.

$^1$H NMR (300 MHz, $CDCl_3$) δ 7.30–7.09 (m, 7H), 6.96 (dd, J=7.3, 0.6 Hz, 1H), 6.35 (d, J=0.9 Hz, 1H), 5.47 (br s, 1H), 3.29 (q, J=6.9 Hz, 2H), 2.84–2.176 (m, 4H), 2.64 (t, J=7.4 Hz, 2H), 1.94–1.67 (m, 9H); $^{13}$C NMR (75 MHz, $CDCl_3$) δ 170.1, 159.2, 154.7, 142.3, 133.6, 128.5, 128.4, 128.1, 125.8, 123.2, 121.9, 108.8, 100.3, 39.6, 31.0, 30.8, 30.3, 28.4, 27.4, 23.3; IR (film, $cm^{-1}$) 3288 (br), 1650; MS(SEI) 350 $(M+H)^+$; Anal. Calc'd. for $C_{23}H_{27}NO_2 \cdot 0.3H_2O$: C, 77.84; H, 7.84; N, 3.95; Found: C, 77.94; H, 7.82; N, 3.82.

EXAMPLE 10

N-[3-[2-(4-Phenylbutyl)benzofuran-4-yl]propyl] propionamide

The title compound was prepared by the general procedure described in Example 9 using intermediate 25 (602 mg, 2 mmol), propionyl anhydride (1 mL) and Raney Nickel (1 mL). Purification by flash chromatography over silica gel (elution with 50% ethyl acetate/hexanes) gave 606 mg (84%) of the desired product as an oil.

$^1$H NMR (300 MHz, $CDCl_3$) δ 7.31–7.09 (m, 7H), 6.96 (dd, J=7.3, 0.6 Hz, 1H), 6.36 (d, J=0.9 Hz, 1H), 5.47 (br s, 1H), 3.29 (q, J=6.9 Hz, 2H), 2.85–2.76 (m, 4H), 2.64 (t, J=7.4 Hz, 2H), 2.11 (q, J=7.6 Hz, 2H), 1.95–1.67 (m, 6H), 1.09 (t, J=7.6 Hz, 3H); $^{13}$C NMR (75 MHz, $CDCl_3$) δ 173.7, 159.1, 154.6, 142.3, 133.7, 128.4, 128.3, 128.1, 125.7, 123.2, 121.8, 108.7, 100.2, 39.3, 35.6, 31.0, 30.8, 30.3, 29.7, 28.4, 27.3, 9.9; IR (film, $cm^{-1}$) 3294 (br), 1642; MS(SEI) 364 $(M+H)^+$; Anal. Calc'd. for $C_{24}H_{29}NO_2 \cdot 0.1H_2O$: C, 78.91; H, 8.06; N, 3.83; Found: C, 78.70; H, 8.10; N, 3.79.

EXAMPLE 11

N-[3-[2-(4-Phenylbutyl)benzofuran-4-yl]propyl] butyramide

The title compound was prepared by the general procedure described in Example 9 using intermediate 25 (602 mg, 2 mmol), n-butyl anhydride (1 mL) and Raney Nickel (1 mL). Purification by flash chromatography over silica gel (elution with 50% ethyl acetate/hexanes) gave 603 mg (80%) of the desired product as an oil.

$^1$H NMR (300 MHz, $CDCl_3$) δ 7.31–7.10 (m, 7H), 6.96 (dd, J=7.3, 0.6 Hz, 1H), 6.36 (d, J=0.9 Hz, 1H), 5.52 (br s, 1H), 3.29 (q, J=6.9 Hz, 2H), 2.85–2.76 (m, 4H), 2.64 (t, J=7.4 Hz, 2H), 2.08 (q, J=7.2 Hz, 2H), 1.94–1.54 (m, 8H), 0.91 (t, J=7.2 Hz, 3H); $^{13}$C NMR (75 MHz, $CDCl_3$) δ 173.0, 159.2, 154.7, 142.3, 133.7, 128.5, 128.4, 128.2, 125.8, 123.2, 121.9, 108.8, 100.3, 39.4, 38.8, 35.7, 31.0, 30.9, 30.4, 28.4, 27.4, 19.2, 13.8; IR (film, $cm^{-1}$) 3293 (br), 1641; MS(SEI) 378 $(M+H)^+$; Anal. Calc'd. for $C_{25}H_{31}NO_2$: C, 79.54; H, 8.28; N, 3.71; Found: C, 79.08; H, 8.39; N, 3.58.

EXAMPLE 12

N-[3-[2-(4-Phenylbutyl)benzofuran-4-yl]propyl]-2-methyl Propionamide

The title compound was prepared by the general procedure described in Example 9 using intermediate 25 (602 mg, 2 mmol), i-butyryl anhydride (1 mL) and Raney Nickel (1 mL). Purification by flash chromatography over silica gel (elution with 30% ethyl acetate/hexanes) gave 5.88 mg (78%) of the desired product as an oil.

$^1$H NMR (300 MHz, $CDCl_3$) δ 7.30–7.09 (m, 7H), 6.96 (d, J=7.2 Hz, 1H), 6.36 (d, J=0.8 Hz, 1H), 5.36 (br s, 1H), 3.29 (q, J=6.9 Hz, 2H), 2.85–2.76 (m, 4H), 2.66 (t, J=7.4 Hz, 2H), 2.28 –2.16 (m, 1H), 1.94–1.67 (m, 6H), 1.06 (t, J=6.9 Hz, 3H); $^{13}$C NMR (75 MHz, $CDCl_3$) δ 173.0, 159.2, 154.7, 142.3, 133.7, 128.5, 128.4, 128.2, 125.8, 123.2, 121.9, 108.8, 100.3, 39.4, 38.8, 35.7, 31.0, 30.9, 3.0.4, 28.4, 27.4, 19.2, 13.8; IR (film, $cm^{-1}$) 3298 (br), 1645; MS(SEI) 378 $(M+H)^+$; Anal. Calc'd. for $C_{25}H_{31}NO_2 \cdot 0.2H_2O$: C, 78.79; H, 8.30; N, 3.68; Found: C, 78.61; H, 8.49; N, 3.50.

EXAMPLE 13

N-[3-[2-[4-(4-Trifluoromethylphenyl)butyl] benzofuran-4-yl]propyl]-cyclopropane Carboxamide A solution of cyclopropanecarbonyl chloride (104 mg, 1 mmol) in $CH_2Cl_2$ (1 mL) to a solution of intermediate 34a (187 mg, 0.5 mmol) and $Et_3N$ (202 mg, 2 mmol) in $CH_2Cl_2$ (20 mL). After stirring for 2 h, the reaction was quenched with water and diluted with $CH_2Cl_2$. The organic layer was washed with brine, dried over MgSO$_4$, concentrated in vacuo to give a crude product which was purified by flash chromatography over silica gel (elution with 30% ethyl acetate/hexanes) to give 177 mg (80%) of the desired product as a solid $^1$H NMR (300 MHz, CDCl$_3$) δ 7.55 (d, J=8.0 Hz, 2H), 7.30–7.25 (m, 3H), 7.11 (t, J=7.4 Hz, 1H), 7.01 (d, J=7.4 Hz, 1H), 6.39 (s, 1H), 5.58 (s, 1H), 3.36 (t, J=6.8 Hz, 2H), 2.87–2.60 (m, 6H), 2.05–1.69 (m, 6H), 1.28–1.19 (m, 1H), 1.01–0.96 (m, 2H), 0.78–0.67 (m, 2H); IR (film:, cm$^{-1}$) 3242 (br), 1635; MS(SEI) 444 (M+H)$^+$; Anal. Calc'd. for C$_{26}$H$_{28}$F$_3$NO$_2$: C, 70.41; H, 6.36. Found: C, 70.61; H, 6.62.

EXAMPLE 14

N-[3-[2-[4-(4-Trifluoromethylphenyl)butyl] benzofuran-4-yl]propyl]-N'-ethyl Urea A solution of intermediate 34a (187 mg, 0.5 mmol) and ethyl isocyanate (71 mg, 1 mmol) in benzene (10 mL) was stirred for 16 h. The benzene was removed in vacuo, and the residue was purified by flash chromatography over silica gel (elution with 80% ethyl acetate/hexanes) to give 150 mg (84%) of the desired product.

$^1$H NMR (300 MHz, CDCl$_3$) δ 7.55 (d, J=8.0 Hz, 2H), 7.30–7.25 (m, 3H), 7.16 (t, J=7.4 Hz, 1H), 6.98 (d, J=7.4 Hz, 1H), 6.38 (d, J=0.8 Hz, 1H), 3.24–3.10 (m, 4H), 2.85–2.60 (m, 6H), 1.94–1.69 (m, 6H), 1.07 (t, J=7.2 Hz, 3H); IR (film, cm$^{-1}$) 3320 (br), 1620; MS(SEI) 447 (M+H)$^+$; Anal. Calc'd. for C$_{25}$H$_{29}$F$_3$N$_2$O$_2$: C, 67.25; H, 6.55; Found: C, 67.35; H, 6.70.

EXAMPLE 15

N-[3-[2-[4-(4-Trifluoromethylphenyl)butyl] benzofuran-4-yl]propyl]-acetamide

A suspension of intermediate 33a (367 mg, 1 mmol) and acetic anhydride (1 mL), and Raney Nickel (1 mL) in THF (40 mL) was hydrogenated at 50 psi for 16 h. After filtration and washing with THF, the filtrate was concentrated in vacuo to give a residue. The residue was purified by flash chromatography over silica gel (elution with 80% ethyl acetate/hexanes) to give 373 mg (90%) of the desired product as an oil.

$^1$H NMR (300 MHz, CDCl$_3$) δ 7.55 (d, J=8.0 Hz, 2H), 7.30–7.25 (m, 3H), 7.16 (t, J=7.4 Hz, 1H), 6.98 (d, J=7.4 Hz, 1H), 6.38 (s, 1H), 5.49 (s, 1H), 3.33 (t, J=6.8 Hz, 2H), 2.86–2.70 (m, 6H), 1.96–1.69 (m, 9H); IR (film, cm$^{-1}$) 3322 (br), 1644; MS(SEI) 418 (M+H)$^+$; Anal. Calc'd. for C$_{24}$H$_{26}$F$_3$NO$_2$: C, 69.05; H, 6.28; Found: C, 68.98; H, 6.25.

EXAMPLE 16

N-[3-[2-[4-(4-Trifluoromethylphenyl)butyl] benzofuran-4-yl]propyl]-propionamide

The title compound was prepared by the general procedure described in Example 15 using intermediate 33a (37 mg, 2 mmol), propionyl anhydride (1 mL) and Raney Nickel (1 mL). Purification by flash chromatography over silica gel (elution with 66% ethyl acetate/hexanes) gave 399 mg (93%) of the desired product as an oil.

$^1$H NMR (300 MHz, CDCl$_3$) δ 7.55 (d, J=8.0 Hz, 2H), 7.30–7.25 (m, 3H), 7.16 (t, J=7.4 Hz, 1H), 6.98 (d, J=7.4 Hz, 1H), 6.38 (s, 1H), 3.35 (t, J=6.8 Hz, 2H), 2.86–2.70 (m, 6H), 2.17 (q, J=7.5 Hz, 2H), 1.96–1.69 (m, 6H), 1.07 (t, J=7.5 Hz, 3H); IR (film, cm$^{-1}$) 3322 (br), 1644; MS(SEI) 432 (M+H)$^+$; Anal. Calc'd. for C$_{25}$H$_{28}$F$_3$NO$_2$: C, 69.59; H, 6.54. Found: C, 69.18; H, 6.73.

EXAMPLE 17

N-[3-[2-[4-(4-Trifluoromethylphenyl)butyl] benzofuran-4-yl]propyl]-butyramide

The title compound was prepared by the general procedure described in Example 15 using intermediate 33a (367 mg, 1 mmol), n-butyryl anhydride (1) and Raney Nickel (1 mL). Purification by flash chromatography over silica gel (elution with 50% ethyl acetate/hexanes) gave 385 mg (87%) of the desired product as an oil.

$^1$H NMR (300 MHz, CDCl$_3$) δ 7.55 (d, J=8.0 Hz, 2H), 7.30–7.26 (m, 3H), 7.16 (t, J=7.4 Hz, 1H), 6.96 (d, J=7.4 Hz, 1H), 6.38 (d, J=0.7 Hz, 1H), 5.39 (s, 1H), 3.35 (t, J=6.8 Hz, 2H), 2.86–2.70 (m, 6H), 2.10 (t, J=7.2 Hz, 2H), 1.96–1.54 (m, 8H), 0.94 (t, J=7.2 Hz, 3H); IR (film, cm$^{-1}$) 3320 (br), 1646; MS(SEI) 446 (M+H)$^+$; Anal. Calc'd. for C$_{26}$H$_{30}$F$_3$NO$_2$: C, 70.09; H, 6.79. Found: C, 70.05; H, 6.92.

EXAMPLE 18

N-[3-[2-[4-(4-Trifluoromethylphenyl)butyl] benzofuran-4-yl]propyl]-isobutyramide The title compound was prepared by the general procedure described in Example 15 using intermediate 33a (367 mg, 12 mmol), i-butyryl anhydride (1 mL) and Raney Nickel (1 mL). Purification by flash chromatography over silical gel (elution with 30% ethyl acetate/hexanes) gave 420 mg (95%) of the desired product as an oil.

$^1$H NMR (300 MHz, CDCl$_3$) δ 7.55 (d, J=8.0 Hz, 2H), 7.30–7.26 (m, 3H), 7.16 (t, J=7.4 Hz, 1H), 6.96 (d, J=7.4 Hz, 1H), 6.38 (d, J=0.7 Hz, 1H), 5.40 (s, 1H), 3.34 (t, J=6.8 Hz, 2H), 2.86–2.70 (m, 6H), 2.29–2.20 (m, 1H), 1.96–1.70 (m, 6H), 1.1 (d, J=6.8 Hz, 6H); IR (film, cm$^{-1}$) 3321 (br), 1642; MS(SEI) 446 (M+H)$^+$; Anal. Calc'd. for C$_{26}$H$_{30}$F$_3$NO$_2$: C, 70.09; H, 6.79. Found: C, 70.05; H, 6.92.

EXAMPLE 19

N-3-(2-(3-Phenylprop-1-yl)benzofuran-3-yl)prop-1-yl Acetamide

The crude amine of intermediate 45a (1.0 eq), triethylamine (2.0 eq), and DMAP (0.10 eq) were dissolved in methylene chloride. A solution of acid chloride (1.2 eq) in methylene chloride was slowly added at 0° C. and the reaction allowed to warm to room temperature for 2 h. The reaction was quenched with 1N HCl and partitioned. The organic layer was washed with saturated sodium bicarbonate. The solution was dried and the solvent removed by rotary evaporation to afford the crude N-3-(2-alkylbenzofuran-4-yl)prop-1-yl alkaneamide. The amide was purified by flash chromatography (ethyl acetate/ hexanes).

$^1$H NMR (CDCl$_3$) δ 7.33–7.21 (m, 6H), 7.14 (t, J=8.0 Hz, 1H), 6.99 (d, J=7.3 Hz, 1H), 6.41 (s, 1H), 5.42 (bs, 1H), 3.31 (q, J=6.4 Hz, 2H), 2.87–2.71 (m, 6H), 2.10 (quint, J=7.50, 2H), 1.97–1.35 (m, 5H); MS(SEI) 336.16 (M+H)$^+$.

EXAMPLE 20

N-3-(2-(3-Phenylprop-1-yl)benzofuran-3-yl)prop-1-yl Propanamide

The title compound was prepared using the general procedure described in Example 19 utilizing intermediate 45a.

¹H NMR (CDCl₃) δ 7.34–7.19 (m, 6H), 7.14 (t, J=8.1 Hz, 1H), 7.00 (d, J=7.2 Hz: 1H), 6.41 (s, 1H), 5.40 (bs, 1H), 3.32 (q, J=6.3 Hz, 2H), 2.88–2.71 (m, 6H), 2.17–2.08 (m, 4H), 1.90 (quint, J=7.3, 2H), 1.11 (t, J=7.6 Hz, 3H); MS(SEI) 350.17 (M+H)⁺.

EXAMPLE 21

N-3-(2-(3-Phenylprop-1-yl)benzofuran-3-yl)prop-1-yl Butyramide

The title compound was prepared using the general procedure described in Example 19 utilizing intermediate 45a.

¹H NMR (CDCl₃) δ 7.33–7.21 (m, 6H), 7.14 (t, J=8.0 Hz, 1H), 6.98 (d, J=7.2 Hz; 1H), 6.41 (s, 1H), 5.39 (bs, 1H), 3.32 (q, J=6.3 Hz, 2H), 2.88–2.71 (m, 6H), 2.12–2.06 (m, 4H), 1.91 (quint, J=7.4, 2H), 1.61 (sex, J=7.5 Hz, 2H), 0.93 (t, J=7.6 Hz, 3H); MS(SEI) 364.23 (M+H)⁺.

EXAMPLE 22

N-3-(2-(3-Phenylprop-1-yl)benzofuran-3-yl)prop-1-yl Cyclopropanecarboxamide

The title compound was prepared using the general procedure described in Example 19 utilizing intermediate 45a.

¹H NMR (CDCl₃) δ 7.34–7.21 (m, 6H), 7.17 (t, J=8.0 Hz, 1H), 6.99 (d, J=7.2 Hz, 1H), 6.42 (s, 1H), 5.56 (bs, 1H), 3.33 (q, J=6.3 Hz, 2H), 2.88–2.71 (m, 6H), 2.10 (q, J=7.4 Hz, 2H), 1.95–1.82 (m, 2H), 1.26–1.20 (m, 1H), 0.97–0.92 (m, 2H), 0.73–0.67 (m, 2H); MS(SEI) 362.25 (M+H)⁺.

EXAMPLE 23

N-3-(2-(2-Phenyleth-1-yl)benzofuran-3-yl)prop-1-yl Acetamide

The title compound was prepared using the general procedure described in Example 19 utilizing intermediate 45a.

¹H NMR (CDCl₃) δ 7.33–7.27 (m, 6H), 7.16 (t, J=8.0 Hz, 1H), 6.99 (d, J=7.2 Hz, 1H), 6.39 (s, 1H), 5.41 (bs, 1H), 3.29 (q, J=6.5 Hz, 2H), 3.09 (s, 4H), 2.84 (t, J=7.6 Hz, 2H), 1.92 (m, 5H); MS(SEI) 322.18 (M+H)⁺.

EXAMPLE 24

N-3-(2-(2-Phenyleth-1-yl)benzofuran-3-yl)prop-1-yl Propanamide

The title compound was prepared using the general procedure described in Example 19 utilizing intermediate 45a.

¹H NMR (CDCl₃) δ 7.33–7.24 (m, 6H), 7.16 (t, J=8.1 Hz, 1H), 6.99 (d, J=7.3 Hz, 1H), 6.39 (s, 1H), 5.49 (bs, 1H), 3.30 (q, J=6.4 Hz, 2H), 3.08 (s, 4H), 2.84 (t, J=7.5 Hz, 2H), 2.13 (q, J=7.6, 2H), 1.91 (quint, J=7.3, 2H), 1.11 (t, J=7.6 Hz, 3H); MS(SEI) 336.17 (M+H)⁺.

EXAMPLE 25

N-3-(2-(2-Phenyleth-1-yl)benzofuran-3-yl)prop-1-yl Butyramide

The title compound was prepared using the general procedure described in Example 19 utilizing intermediate 45a.

¹H NMR (CDCl₃) δ 7.33–7.23 (m, 6H), 7.13 (t, J=8.0 Hz, 1H), 6.99 (d, J=7.2 Hz, 1H), 6.39 (s, 1H), 5.38 (bs, 1H), 3.30 (q, J=6.3 Hz, 2H), 3.11 (s, 4H), 2.84 (t, J=7.6 Hz, 2H), 2.08 (t, J=7.7, 2H), 1.90 (quint, J=7.3, 2H), 1.61 (sex, J=7.5 Hz, 2H), 0.95 (t, J=7.6 Hz, 3H); MS(SEI) 350.20 (M+H)⁺.

EXAMPLE 26

N-3-(2-(2-Phenyleth-1-yl)benzofuran-3-yl)prop-1-yl-cyclopropanecarboxamide

The title compound was prepared using the general procedure described in Example 19 utilizing intermediate 45a.

¹H NMR (CDCl₃) δ 7.33–7.23 (m, 6H), 7.16 (t, J=8.0 Hz, 1H), 7.00 (d, J=7.2 Hz, 1H), 6.40 (s, 1H), 5.51 (bs, 1H), 3.31 (q, J=6.3 Hz, 2H), 3.09 (s, 4H), 2.84 (t, J=7.6, 2H), 1.94 (quint, J=7.3, 2H), 1.27–1.20 (m, 1H), 0.97–0.92 (m, 2H), 0.74–0.67 (m, 2H); MS(SEI) 348.32 (M+H)⁺.

EXAMPLE 27

N-{3-[3-Chloro-2-(4-phenylbutyl)benzo[b]furan-4-yl]-propyl}ethoxycarboxamide The benzofuran illustrated as intermediate 27 (0.1 mmol) in Reaction Scheme 5 was chlorinated with N-chlorosuccinimide (0.11 mmol) in acetonitrile (5 mL) and heated to reflux for 16 hours. The reaction was cooled and the solvent removed in vacuo. The crude product was purified by preparative HPLC to give the title compound in 47% yield.

¹H NMR (300 MHz, CDCl₃) δ 1.14 (t, J=7.6, 3H), 1.73 (m, 4H), 1.92 (m, 2H), 2.20 (q, J=7.6, 2H), 2.67 (t, J=7.6, 2H), 2.84 (t, J=7.0, 2H), 3.10 (t, J=7.5, 2H), 3.36 (q, J=7.0, 2H), 5.52 (m, 1H), 7.00 (d, J=7.5, 1H), 7.21 (m, 7H); MS(SEI) 398.17 (M+H)⁺; analytical HPLC retention time= 4.86 minutes, purity=100%; conditions for preparative HPLC: Column=YMC C18 S5 20 mm×100 mm; solvent A=10% MeOH, 90% H₂O, 0.1% TFA; solvent B=90% MeOH, 10% H₂O, 0.1% TFA; gradient from 30% to 100% B over 10 minutes with a 5 minute hold time at 100% B; flow=20 ml per minute; wavelength=220 nM.

EXAMPLES 28, (+)29 & (−)30

N-({(1R,2R)-2-[2-(4-Phenylbutyl)benzo[b]furan-4-yl]-cyclopropyl}methyl)acetamide A solution of acetyl chloride (188 mg, 2.4 mmol) in CH₂Cl₂ was added to a solution of intermediate 12B (383 mg, 1.2 mmol) and Et₃N (485 mg, 4.8 mmol) in CH₂Cl₂ (20 mL). After stirring for 16 h at ambient temperature, the reaction was quenched with water and diluted with CH₂Cl₂. The organic layer was washed with brine, dried over MgSO₄, filtered, and concentrated in vacuo to give a crude product which was purified by flash chromatography over silica gel (elution with 25% ethyl acetate/hexanes) to give 346 mg (80%) of the racemic product of Example 28 as an oil.

¹H NMR (300 MHz, CDCl₃) δ 7.31–7.06 (m, 7H), 6.72 (d, J=7.5 Hz, 1H), 6.46 (d, J=0.8 Hz, 1H), 5.69 (br, 1H), 3.41–3.25 (m, 2H), 2.82 (t, J=6.7 Hz, 2H), 2.69 (t, J=7.5 Hz, 2H), 2.18–1.97 (m, 1H), 1.97 (s, 3H), 1.83–69 (m, 4H), 1.42–1.35 (m, 1H), 1.11–1.05 (m, 1H), 0.98–0.92 (m, 1H); ¹³C NMR (75 MHz, CDCl₃) δ 170.1, 159.2, 154.4, 142.3, 134.4, 128.5, 128.4, 125.8, 123.2, 117.9, 108.4, 100.3, 43.9, 35.7, 31.0, 28.4, 27.4, 23.4, 21.8, 19.9, 13.5; IR (film, cm⁻¹) 3287(br); MS(SEI) 362 (M+H)⁺; Anal. Calc'd. for C₂₄H₂₇NO₂: C, 79.74; H, 7.53; Found: C, 79.14; H, 7.59.

The racemate of Example 28 (20 mg) was subjected to preparative HPLC conditions (Chiralcel OD, 10% i-PrOH in hexane, wave length 220 nm, and flow rate 70 mL/min) to give Example (+)29 (8 mg) and Example (−)30 (8 mg). Optical rotations are as follows: (+)29: [α]$_D^{25}$+8.9 (MeOH); (−)30: [α]$_D^{25}$−8.6 (MeOH).

EXAMPLE 31

N-({(1R,2R)-2-[2-(4-Phenylbutyl)benzo[b]furan-4-yl]-cyclopropyl}methyl)propanamide The title compound was prepared by the general procedure described in Example 28 using intermediate 12B (383 mg, 1.2 mmol), Et$_3$N (485 mg, 4.8 mmol) and propionyl chloride (222 mg, 2.4 mmol). Purification by flash chromatography over silica gel (elution with 66% ethyl acetate/hexanes) gave 369 mg (82%) of the title compound as an oil.

$^1$H NMR (300 MHz, CDCl$_3$) δ 7.31–7.06 (m, 7H), 6.72 (d, J=7.5 Hz, 1H), 6.46 (d, J=0.8 Hz, 1H), 5.62 (br, 1H), 3.39–3.30 (m, 2H), 2.79 (t, J=6.7 Hz, 2H), 2.69 (t, J=7.5 Hz, 2H), 2.23 (q, J=7.4 Hz, 2H), 2.03–2.00 (m, 1H), 1.98–1.69 (m, 4H), 1.42–1.35 (m, 1H), 1.11–1.05 (m, 4H), 0.98–0.92 (m, 1H); $^{13}$C NMR (75 MHz, CDCl$_3$) δ 173.8, 159.2, 154.4, 142.3, 134.4, 128.5, 128.4, 125.8, 123.2, 117.9, 108.4, 100.4, 43.9, 35.8, 31.1, 29.9, 28.5, 27.5, 21.8, 20.0, 13.4, 10.0; IR (film, cm$^{-1}$) 3289(br); MS(SEI) 376 (M+H)$^+$; Anal. Calc'd. for C$_{25}$H$_{29}$NO$_2$ C, 79.96; H, 7.78; Found: C, 79.30; H, 7.89.

EXAMPLE 32

N-({(1R,2R)-2-[2-(4-Phenylbutyl)benzo[b]furan-4-yl]-cyclopropyl}methyl)butanamide The title compound was prepared by the general procedure described in Example 28 using intermediate 12B (383 mg, 1.2 mmol), Et$_3$N (485 mg, 4.8 mmol) and butyryl chloride (256 mg, 2.4 mmol). Purification by flash chromatography over silica gel (elution with 50% ethyl acetate/hexanes) gave 135 mg (50%) of the desired product as an oil.

$^1$H NMR (300 MHz, CDCl$_3$) δ 7.31–7.06 (m, 7H), 6.72 (d, J=7.5 Hz, 1H), 6.46 (d, J=0.8 Hz, 1H), 5.62 (br, 1H), 3.42–3.30 (m, 2H), 2.81 (t, J=6.6 Hz, 2H), 2.69 (t, J=7.5 Hz, 2H), 2.17 (t, J=7.4 Hz, 2H), 2.03–2.00 (m, 1H), 1.98–1.69 (m, 6H), 1.42–1.35 (m, 1H), 1.11–1.05 (m, 1H), 0.98–0.92 (m, 4H); $^{13}$C NMR (75 MHz, CDCl$_3$) δ 173.1, 159.2, 154.4, 142.3, 134.4, 128.5, 128.4, 125.8, 123.2, 117.9, 108.4, 100.4, 43.7, 38.8, 35.8, 31.1, 28.4, 27.5, 21.8, 1:9.9, 19.3, 13.9, 13.4; IR (film, cm$^{-1}$) 3297 (br); MS(SEI) 390 (M+H)$^+$; Anal. Calc'd. for C$_{26}$H$_{31}$NO$_2$.H$_2$O: C, 79.07; H, 8.06; Found: C, 79.01; H, 8.07.

EXAMPLE 33

N-({(1R,2R)-2-[2-(4-Phenylbutyl)benzo[b]furan-4-yl]-cyclopropyl}methyl)-2-methylpropanamide The title compound was prepared by the general procedure described in Example 28 using intermediate 12B (383 mg, 1.2 mmol), Et$_3$N (485 mg, 4.8 mmol) and iso-butyryl chloride (256 mg, 2.4 mmol). Purification by flash chromatography over silica gel (elution with 50% ethyl acetate/hexanes) gave 396 mg (85%) of the title compound as an oil.

$^1$H NMR (300 MHz, CDCl$_3$) δ 7.31–7.06 (m, 7H), 6.72 (d, J=7.5 Hz, 1H), 6.46 (d, J=0.8 Hz, 1H), 5.63 (br, 1H), 3.41–3.29 (m, 2H), 2.81 (t, J=6.6 Hz, 2H), 2.68 (t, J=7.5 Hz, 2H), 2.38–2.28 (m, 1H), 2.05–1.99 (m, 1H), 1.82–1.69 (m, 4H), 1.38–1.34 (m, 1H), 1.20–1.05 (m, 7H), 0.98–0.92 (m, 1H); $^{13}$C NMR (75 MHz, CDCl$_3$) δ 177.0, 159.1, 154.4, 142.3, 134.4, 128.5, 128.4, 125.8, 123.2, 117.9, 108.4, 100.4, 43.7, 35.8, 35.7, 31.0, 28.4, 27.5, 21.9, 19.8, 19.7, 13.3; IR (film, cm$^{-1}$) 3291 (br); MS(SEI) 390 (M+H)$^+$; Anal. Calc'd. for C$_{26}$H$_{31}$NO$_2$: C, 80.17; H, 8.02; Found: C, 79.83; H, 8.29.

EXAMPLE 34

N-({(1R,2R)-2-[2-(4-Phenylbutyl)benzo[b]furan-4-yl]-cyclopropyl}methyl)cyclopropylcarboxamide The title compound was prepared by the general procedure described in Example 28 using intermediate 12B (383 mg, 1.2 mmol), Et$_3$N (485 mg, 4.8 mmol) and cyclopropane carbonyl chloride (251 mg, 2.4 mmol). Purification by flash chromatography over silica gel (elution with 30% ethyl acetate/hexanes) gave 340 mg (75%) of the title compound as an oil.

$^1$H NMR (300 MHz, CDCl$_3$) δ 7.31–7.06 (m, 7H), 6.72 (d, J=7.5 Hz, 1H), 6.46 (d, J=0.8 Hz, 1H), 5.81 (br, 1H), 3.43–3.28 (m, 2H), 2.81 (t, J=6.6 Hz, 2H), 2.69 (t, J=7.5 Hz, 2H), 2.03–2.00 (m, 1H), 1.81–1.71 (m, 4H), 1.42–0.68 (m, 8H); $^{13}$C NMR (75 MHz, CDCl$_3$) δ 173.1, 159.1, 154.4, 142.3, 134.4, 128.5, 128.4, 1 25.8, 123.2, 117.9, 108.4, 100.4, 44.0, 35.7, 31.0, 28.4, 27.5, 22.0, 19.9, 14.9, 13.4, 7.27; IR (film, cm$^{-1}$) 3297 (br); MS(SEI) 388 (M+H)$^+$; Anal. Calc'd. for C$_{26}$H$_{29}$NO$_2$: C, 80.59; H, 7.54; Found: C, 79.12; H, 7.72.

EXAMPLE 35

N-({(1R,2R)-2-[2-(4-Phenylbutyl)benzo[b]furan-4-yl]- cyclopropyl}methyl)(ethylamino)carboxamide A solution of intermediate 12B (383 mg, 1.2 mmol), and ethyl isocyanate (170 mg, 2.4 mmol) in benzene (10 mL) was stirred for 16 h. The benzene was removed in vacuo and the residue was purified by flash chromatography over silica gel (elution with 80% ethyl acetate/hexanes) to give 360 mg (77%) of the title compound as an oil.

$^1$H NMR (300 MHz, CDCl$_3$) δ 7.31–7.06 (m, 7H), 6.71 (d, J=7.5 Hz, 1H), 10 6.45 (d, J=0.8 Hz, 1H), 4.81 (t, J=5.3 Hz, 1H), 4.61 (t, J=5.3 Hz, 1H), 3.28–3.12 (m, 4H), 2.79 (t, J=6.7 Hz, 2H), 2.69 (t, J=7.5 Hz, 2H), 1.99–1.68 (m, 5H), 1.39–1.34 (m, 1H), 1.10–0.87 (m, 5H); $^{13}$C NMR (75 MHz, CDCl$_3$) δ 159.0, 158.4, 154.4, 142.3, 134.4, 128.5, 128.4, 125.8, 123.2, 117.9, 108.4, 100.4, 44.6, 35.7, 35.3, 31.1, 28.4, 27.5, 15 22.3, 19.7, 15.6, 13.5; IR (film, cm$^{-1}$) 3335 (br); MS(SEI) 391 (M+H)$^+$; Anal. Calc'd. for C$_{25}$H$_{30}$N$_2$O$_2$: C, 76.89; H, 7.74; Found: C, 76.67; H, 7.84.

EXAMPLE 36

N-[((1R,2R)-2-{2-[4-(4-Fluorophenyl)butyl]benzo[b]furan-4-yl}-cyclopropyl)methyl]acetamide The title compound was prepared by the general procedure described in Example 28 using intermediate 12A (67 mg, 0.2 mmol), Et$_3$N (81 mg, 0.8 mmol) and acetyl chloride (31 mg, 0.4 mmol). Purification by flash chromatography over silica gel (elution with 66% ethyl acetate/hexanes) gave 61 mg (80%) of the title compound as an oil.

$^1$H NMR (300 MHz, CDCl$_3$) δ 7.29–6.93 (m, 6H), 6.74 (d, J=7.5 Hz, 1H), 6.48 (d, J=0.8 Hz, 1H), 5.72 (br, 1H), 3.37 (dd, J=7.0, 5.7 Hz, 2H), 2.82 (t, J=6.7 Hz, 2H), 2.67 (t, J=7.5 Hz, 2H), 2.20–2.02 (m, 1H), 2.01 (s, 3H), 1.82–1.72 (m, 4H), 1.42–1.37 (m, 1H), 1.12–1.05 (m, 1H), 0.98–0.92 (m, 1H); $^{13}$C NMR (75 MHz, CDCl$_3$) δ 170.2, 161.4 (d, J=242.2 Hz), 159.2, 154.5, 138.0 (d, J=3.3 Hz), 134.4, 129.9 (d, J=31.2 Hz), 128.4, 125.8, 123.4, 118.0, 115.3 (d, J=242.2 Hz), 108.5, 100.5, 44.0, 35.0, 31.2, 28.5, 27.4, 23.4, 21.9, 20.0, 13.5; IR (film, cm$^{-1}$) 3287 (br); MS(SEI) 380 (M+H)$^+$; Anal. Calc'd. for C$_{24}$H$_{26}$FNO$_2$ C, 75.25; H, 6.95; Found: C, 74.80; H, 7.00.

EXAMPLE 37

N-[((1R,2R)-2-{2-[4-(4-Fluorophenyl)butyl]benzo[b]furan-4-yl}-cyclopropyl)methyl]propanamide The title compound was prepared by the general procedure described in Example 28 using intermediate 12A (67 mg, 0.2 mmol), Et$_3$N (81 mg, 0.8 mmol) and propionyl chloride (32 mg, 0.4 mmol). Purification by flash chromatography over silica gel (elution with 66% ethyl acetate/hexanes) gave 60 mg (77%) of the desired product as an oil.

$^1$H NMR (300 MHz, CDCl$_3$) δ 7.31–7.06 (m, 6H), 6.72 (d, J=7.5 Hz, 1H), 6.48 (d, J=0.8 Hz, 1H), 5.65 (br, 1H), 3.37 (dd, J=7.0, 5.7 Hz, 2H), 2.79 (t, J=6.7 Hz, 2H), 2.69 (t, J=7.5 Hz, 2H), 2.25 (q, J=7.4 Hz, 2H), 2.06–2.00 (m, 1H), 1.82–1.67 (m, 4H), 1.42–1.35 (m, 1H), 1.11–1.04 (m, 4H), 0.98–0.93 (m, 1H); $^{13}$C NMR (75 MHz, CDCl$_3$) δ 173.9, 161.4 (d, J=241.6 Hz), 159.1, 154.5, 138.0 (d, J=3.3 Hz), 134.6, 129.9 (d, J=242.2 Hz), 128.6, 123.3, 118.0, 115.3 (d, J=20.9 Hz), 108.5, 100.5, 43.8, 35.0, 31.1, 29.9, 28.5, 27.4, 22.0, 20.0, 14.5, 13.4, 10.0; IR (film, cm$^{-1}$) 3295(br); MS(SEI) 394 (M+H)$^+$; Anal. Calc'd. for C$_{25}$H$_{28}$FNO$_2$, C, 75.62; H, 7.21; Found: C, 75.52; H, 7.65.

EXAMPLE 38

N-[((1R,2R)-2-{2-[4-(4-Fluorophenyl)butyl]benzo[b]furan-4-yl}-cyclopropyl)methyl]butanamide The title compound was prepared by the general procedure described in Example 28 using intermediate 12A (67 mg, 0.2 mmol), Et$_3$N (81 mg, 0.8 mmol) and butyryl chloride (43 mg, 0.4 mmol). Purification by flash chromatography over silica gel (elution with 50% ethyl acetate/hexanes) gave 67 mg (82%) of the title compound as an oil.

$^1$H NMR (300 MHz, CDCl$_3$) δ 7.31–6.92 (m, 6H), 6.74 (d, J=7.5 Hz, 1H), 6.48 (d, J=0.8 Hz, 1H), 5.66 (br, 1H), 3.39 (dd, J=7.0, 5.6 Hz, 2H), 2.83 (t, J=6.6 Hz, 2H), 2.71 (t, J=7.5 Hz, 2H), 2.19 (t, J=7.2 Hz, 2H), 2.05–2.02 (m, 1H), 1.82–1.69 (m, 6H), 1.39–1.378 (m, 1H), 1.11–1.05 (m, 1H), 0.98–0.92 (m, 4H); $^{13}$C NMR (75 MHz, CDCl$_3$) δ 173.1, 161.4 (d, J=241.6 Hz), 159.2, 154.4, 15 138.0 (d, J=3.7 Hz), 134.4, 129.9 (d, J=241.6 Hz), 128.4, 123.2, 117.9, 115.3 (d, J=241.6 Hz), 108.4, 100.4, 43.8, 38.8, 35.0, 31.2, 28.5, 27.5, 22.0, 20.0, 19.3, 14.0, 13.4; IR (film, cm$^{-1}$) 3298 (br); MS(SEI) 408 (M+H)$^+$; Anal. Calc'd. for C$_{26}$H$_{30}$FNO$_2$.0.4H$_2$O: C, 75.30; H, 7.49; Found: C, 75.05; H, 7.80.

EXAMPLE 39

N-[((1R,2R)-2-{2-[4-(4-Fluorophenyl)butyl]benzo[b]furan-4-yl}-cyclopropyl)methyl]-2-methylpropanamide The title compound was prepared by the general procedure described in Example 28 using 12A (67 mg, 0.2 mmol), Et$_3$N (81 mg, 0.8 mmol) and iso-butyryl chloride (43 mg, 0.4 mmol). Purification by flash chromatography over silica gel (elution with 50% ethyl acetate/hexanes) gave 69 mg (85%) of the desired product as an oil.

$^1$H NMR (300 MHz, CDCl$_3$) δ 7.31–6.92 (m, 6H), 6.70 (d, J=7.5 Hz, 1H), 30 6.45 (d, J=0.8 Hz, 1H), 5.65 (br, 1H), 3.41 (dd, J=7.0, 5.6 Hz, 2H), 2.82 (t, J=6.7 Hz, 2H), 2.69 (t, J=7.4 Hz, 2H), 2.39–2.29 (m, 1H), 2.07–1.99 (m, 1H), 1.80–1.69 (m, 4H), 1.38–1.34 (m, 1H), 1.21–1.07 (m, 7H), 0.98–0.193 (m, 1H); $^{13}$C NMR (75 MHz, CDCl$_3$) δ 177.1, 161.4 (d, J=241.4 Hz), 159.1, 154.4, 138.0 (d, J=3.3 Hz), 134.4, 129.9 (d, J=7.7 Hz), 128.5, 128.4, 123.3, 118.0, 115.3 (d, J=241.6 Hz), 108.5, 100.6, 43.7, 35.9, 35.0, 31.2, 28.5, 27.5, 21.9, 19.8, 19.7, 13.3; IR (film, cm$^{-1}$) 3300 (br); MS(SEI) 408 (M+H)$^+$; Anal. Calc'd. for C$_{26}$H$_{30}$FNO$_2$.0.4H$_2$O: C, 75.30; H, 7.49; Found: C, 75.05; H, 7.80.

EXAMPLE 40

N-[((1R,2R)-2-{2-[4-(4-Fluorophenyl)butyl]benzo[b]furan-4-yl}-cyclopropyl)methyl]cyclopropylcarboxamide The title compound was prepared by the general procedure described in Example 28 using intermediate 12A (67 mg, 0.2 mmol), Et$_3$N (81 mg, 0.8 mmol) and cyclopropane carbonyl chloride (42 mg, 0.4 mmol). Purification by flash chromatography over silica gel (elution with 30% ethyl acetate/hexanes) gave 67 mg (77%) of the title compound as an oil.

$^1$H NMR (300 MHz, CDCl$_3$) δ 7.37–6.92 (m, 6H), 6.75 (d, J=7.5 Hz, 1H), 6.49 (d, J=0.8 Hz, 1H), 5.86 (br, 1H), 4.12 (dd, J=7.0, 5.5 Hz, 2H), 2.82 20 (t, J=6.6 Hz, 2H), 2.65 (t, J=7.5 Hz, 2H), 2.07–2.02 (m, 1H), 1.83–1.72 (m, 4H), 1.42–0.96 (m, 6H), 0.76–0.70 (m, 2H); $^{13}$C NMR (75 MHz, CDCl$_3$) δ 173.6, 161.4 (d, J=241.8 Hz), 159.1, 154.4, 138.0 (d, J=3.1 Hz), 134.6, 129.9 (d, J=7.8 Hz), 128.5, 123.9, 115.3 (d, J=20.9 Hz), 108.4, 100.6, 44.1, 35.0, 31.2, 28.4, 27.5, 22.0, 19.9, 14.9, 13.4, 7.27; IR (film, cm$^{-1}$) 3299 (br); MS(SEI) 406 (M+H)$^+$; Anal. Calc'd. for C$_{26}$H$_{28}$FNO$_2$.0.2H$_2$O: C, 76.33; H, 7.00; Found: C, 76.05; H, 7.15.

EXAMPLE 41

N-[((1R,2R)-2-{2-[4-(4-Fluorophenyl)butyl]benzo[b]furan-4-yl-}-cyclopropyl)methyl](ethylamino)carboxamide The title compound was prepared by the general procedure described in Example 40 using intermediate 12A (67 mg, 0.2 mmol) and ethyl isocyanate (29 mg, 2.4 mmol). Purification by flash chromatography over silica gel (elution with 30% ethyl acetate/hexanes) gave 49 mg (60%) of the desired product as an oil.

$^1$H NMR (300 MHz, CDCl$_3$) δ 7.31–6.93 (m, 6H), 6.78 (d, J=7.5 Hz, 1H), 6.49 (d, J=0.8 Hz, 1H), 4.61 (t, J=5.2 Hz, 1H), 4.42 (t, J=5.2 Hz, 1H), 3.35–3.15 (m, 4H), 2.84 (t, J=6.7 Hz, 2H), 2.69 (t, J=7.5 Hz, 2H), 2.02–1.68 (m, 5H), 1.45–1.35 (m, 1H), 1.15–0.90 (m, 5H); $^{13}$C NM,R (75 MHz, CDCl$_3$) δ 161.4 (d, J=241.5 Hz), 159.0, 158.4, 154.4, 138.0 (d, J=3 Hz), 134.8, 129.9 (d, J=7.8 Hz), 128.5, 123.3, 118.0, 115.0 (d, J=20.8 Hz), 108.4, 100.6, 44.8, 35.5, 35.0, 31.2, 28.4, 27.4, 22.4, 19.7, 15.6, 13.5; IR (film, cm$^1$) 3339 (br); MS(SEI) 391 (M+H)$^+$; Anal. Calc'd. for C$_{25}$H$_{29}$FN$_2$O$_2$: C, 73.50; H, 7.16; Found: C, 73.24; H, 7.24.

EXAMPLE 42

N-({2-[(2R)-2-(4-Phenylbutyl)(2,3-dihydrobenzo[b]furan-4-yl)]-(1R,2R)cyclopropyl}methyl)acetamide A solution of acetyl chloride (110 mg, 1.4 mmol) in CH$_2$Cl$_2$ was added to a solution of intermediate 17A' (225 mg, 0.7 mmol) and Et$_3$N (283 mg, 2.8 mmol) in CH$_2$Cl$_2$ (20 mL). After stirring for 16 h, the reaction was quenched with water and diluted with CH$_2$Cl$_2$. The organic layer was washed with brine, dried over MgSO$_4$, and concentrated in vacuo to give a crude product which was purified by flash chromatography over silica gel (elution with 25% ethyl acetate/hexanes) to give 101 mg (40%) of the title compound as a solid.

$^1$H NMR (300 MHz, CDCl$_3$) δ 7.30–7.14 (m, 5H), 7.01 (d, J=7.8 Hz, 1H), 6.58 (d, J=7.8 Hz, 1H), 6.31 (d, J=7.7 Hz, 1H), 5.62 (br s, 1H), 4.83–4.72 (m, 1H), 3.35–3.20 (m, 3H), 2.83 (dd, J=15.4, 7.8 Hz, 1H), 2.63 (t, J=7.8 Hz, 2H), 2.04 (s, 3H), 1.98–1.26 (m, 8H), 0.97–0.85 (m, 2H); $^{13}$C NMR (75 MHz, CDCl$_3$) δ 170.0, 159.2, 142.5, 138.9, 128.5, 128.3, 128.2, 126.1, 125.8, 115.4, 106.7, 83.3, 43.8, 36.2, 35.9, 34.4, 31.5, 25.2, 23.4, 21.7, 19.7, 13.6; IR (film, cm$^{-1}$) 3333, 1649; MS(SEI) 364 (M+H)$^+$; [α]$^{25}_D$+54° (MeOH); Anal. Calc'd. for C$_{24}$H$_{29}$NO$_2$ C, 79.30; H, 8.04; N, 3.85. Found: C, 79.20; H, 8.15; N, 3.83; m.p. 65–66° C.

EXAMPLE 43

N-({2-[(2R)-2-(4-Phenylbutyl)(2,3-dihydrobenzo[b]furan-4-yl)]-(1R,2R)cyclopropyl}methyl)propanamide The title compound was prepared by the general procedure described in Example 42 using intermediate 17A' (225 mg, 0.7 mmol), Et$_3$N (283 mg, 2.8 mmol) and propionyl chloride (130 mg, 1.4 mmol). Purification by flash chromatography over silica gel (elution with 66% ethyl acetate/hexanes) gave 111 mg (45%) of the title compound as an oil.

$^1$H NMR (300 MHz, CDCl$_3$) δ 7.30–7.14 (m, 5H), 7.01 (d, J=7.8 Hz, 1H), 6.58 (d, J=7.8 Hz, 1H), 6.31 (d, J=7.7 Hz, 1H), 5.60 (br s, 1H), 4.81–4.72 (m, 1H), 3.35–3.23 (m, 3H), 2.83 (dd, J=15.4, 7.7 Hz, 1H), 2.63 (t, J=7.4 Hz, 2H), 2.19 (q, J=8.4 Hz, 2H), 1.86–0.86 (m, 13H); $^{13}$C NMR (75 MHz, CDCl$_3$) δ 173.8, 159.2, 142.5, 138.9, 128.5, 128.3, 128.2, 126.1, 125.8, 115.4, 106.7, 83.3, 43.7, 36.2, 35.9, 34.4, 31.5, 29.8, 25.2, 21.8, 13.5, 10.0; IR (film, cm$^{-1}$) 3300, 1645; MS(SEI) 378 (M+H)$^+$; [α]$^{25}_D$+58° (MeOH); Anal. Calc'd. for C$_{25}$H$_{31}$NO$_2$.0.3 H$_2$O C, 78.41; H, 8.32; N, 3.66. Found: C, 78.36; H, 8.76; N, 3.56.

EXAMPLE 44

N-({2-[(2R)-2-(4-Phenylbutyl)(2,3-dihydrobenzo[b]furan-4-yl)]-(1R,2R)cyclopropyl}methyl)butanamide The title compound was prepared by the general procedure described in Example 42 using intermediate 17A' (225 mg, 0.7 mmol), Et$_3$N (283 mg, 2.8 mmol) and n-butyryl chloride (149 mg, 1.4 mmol). Purification by flash chromatography over silica gel (elution with 50% ethyl acetate/hexanes) gave 135 mg (50%) of the title compound as an oil.

$^1$H NMR (300 MHz, CDCl$_3$) δ 7.30–7.14 (m, 5H), 7.01 (d, J=7.8 Hz, 1H), 6.58 (d, J=7.7 Hz, 1H), 6.31 (d, J=7.7 Hz, 1H), 5.58 (br s, 1H), 4.81–4.71 (m, 1H), 3.35–3.23 (m, 3H), 2.83 (dd, J=15.4, 7.7 Hz, 1H), 2.64 (t, J=7.3 Hz, 2H), 2.15 (t, J=7.7 Hz, 2H), 1.86–0.86 (m, 15H); $^{13}$C NMR (75 MHz, CDCl$_3$) δ 173.0, 159.2, 142.5, 138.9, 128.5, 128.3, 128.2, 126.1, 125.7, 115.4, 106.7, 83.3, 43.6, 38.5, 36.2, 35.9, 34.4, 31.5, 25.2, 19.7, 19.2, 13.8, 13.5; IR (film, cm$^{-1}$) 3299, 1649; MS(SEI) 392 (M+H)$^+$; [α]$^{25}_D$+47° (MeOH); Anal. Calc'd. for C$_{26}$H$_{33}$NO$_2$.0.5 H$_2$O C, 77.96; H, 8.56; N, 3.50. Found: C, 77.83; H, 8.70; N, 3.51.

EXAMPLE 45

N-({2-[(2R)-2-(4-Phenylbutyl)(2,3-dihydrobenzo[b]furan-4-yl)]-(1R,2R)cyclopropyl}methyl)-2-methylpropanamide The title compound was prepared by the general procedure described in Example 42 using intermediate 17A' (225 mg, 0.7 mmol), Et$_3$N (283 mg, 2.8 mmol) and i-butyryl chloride (149 mg, 1.4 mmol). Purification by flash chromatography over silica gel (elution with 50% ethyl acetate/hexanes) gave 137 mg (50%) of the title compound as an oil.

$^1$H NMR (300 MHz, CDCl$_3$) δ 7.29–7.14 (m, 5H), 7.01 (d, J=7.8 Hz, 1H), 6.58 (d, J=7.7 Hz, 1H), 6.31 (d, J=7.7 Hz, 1H), 5.56 (br s, 1H), 4.81–4.71 (m, 1H), 3.35–3.20 (m, 3H), 2.83 (dd, J=15.3, 7.8 Hz, 1H), 2.61 (t, J=7.3 Hz, 2H), 2.37–2.28 (m, 1H), 1.86–0.84 (m, 16H); IR (film, cm$^{-1}$) 3299, 1644; MS(SEI) 392 (M+H)$^+$; [α]$^{25}_D$+43° (MeOH); Anal. Calc'd. for C$_{26}$H$_{33}$NO$_2$.0.9 H$_2$O C, 76.58; H, 8.60; N, 3.43. Found: C, 76.67; H, 8.55; N, 3.36.

EXAMPLE 46

N-({2-[(2R)-2-(4-Phenylbutyl)(2,3-dihydrobenzo[b]furan-4-yl)]-(1R,2R)cyclopropyl}methyl)cyclopropylcarboxamide The title compound was prepared by the general procedure described in Example 42 using intermediate 17A' (225 mg, 0.7 mmol), Et$_3$N (283 mg, 2.8 mmol) and cyclopropane carbonyl chloride (146 mg, 1.4 mmol). Purification by flash chromatography over silica gel (elution with 30% ethyl acetate/hexanes) gave 130 mg (48%) of the desired product as a solid.

$^1$H NMR (300 MHz, CDCl$_3$) δ 7.36–7.14 (m, 5H), 7.01 (d, J=7.8 Hz, 1H), 6.58 (d, J=7.7 Hz, 1H), 6.31 (d, J=7.7 Hz, 1H), 5.76 (br s, 1H), 4.82–4.72 (m, 1H), 3.37–3.24 (m, 3H), 2.83 (dd, J=15.4, 7.7 Hz, 1H), 2.64 (t, J=7.3 Hz, 2H), 1.86–0.77 (m, 15H); $^{13}$C NMR (75 MHz, CDCl$_3$) δ 173.5, 159.2, 142.5, 138.9, 128.5, 128.3, 128.2, 126.1, 125.7, 115.4, 106.7, 83.3, 43.9, 38.5, 36.2, 35.9, 34.4, 31.5, 25.2, 22.0, 19.7, 14.8, 13.5, 7.27; IR (film, cm$^{-1}$) 3314, 1635; MS(SEI) 390 (M+H)$^+$; [α]$^{25}_D$+52° (MeOH); Anal. Calc'd. for C$_{26}$H$_{31}$NO$_2$ C, 80.17; H, 8.02; N, 3.60; Found: C, 80.20; H, 8.00; N, 3.50; m.p. 81–80° C.

EXAMPLE 47

N-({2-[(2R)-2-(4-Phenylbutyl)(2,3-dihydrobenzo[b]furan-4-yl)]-(1R,2R)cyclopropyl}methyl)(ethylamino)carboxamide A solution of intermediate 17A' (225 mg, 0.7 mmol) and ethyl isocyanate (99 mg, 1.4 mmol) in benzene (10 mL) was stirred for 16 h. The benzene was removed in vacuo, purified by flash chromatography over silica gel (elution with 50% ethyl acetate/hexanes) to give 164 mg (60%) of the title compound.

$^1$H NMR (300 MHz, CDCl$_3$) δ 7.32–7.18 (m, 5H), 7.02 (d, J=7.7 Hz, 1H), 6.59 (d, J=7.8 Hz, 1H), 6.32 (d, J=7.7 Hz, 1H), 4.86–4.64 (m, 3H), 3.34–3.14 (m, 5H), 2.84 (dd, J=15.4, 7.7 Hz, 1H), 2.66 (t, J=7.3 Hz, 2H), 1.94–1.26 (m, 8H), 1.11 (t, J=7.2 Hz, 3H), 0.95–0.83 (m, 2H); $^{13}$C NMR (75 MHz, CDCl$_3$) δ 159.3, 158.5, 142.6, 139.2, 128.6, 128.5, 128.3, 128.2, 126.2, 125.9, 115.6, 106.7, 83.4, 44.7, 36.3, 36.0, 35.4, 34.5, 31.6, 25.4, 22.5, 19.7, 15.7, 13.6; IR (film, cm$^{-1}$) 3335, 1626; MS(SEI) 393 (M+H)$^+$; [α]$^{25}_D$+64° (MeOH); Anal. Calc'd. for C$_{25}$H$_{31}$N$_2$O$_2$ C, 76.50; H, 8.22; N, 7.14. Found: C, 76.35; H, 8.24; N, 7.10; m.p. 69–70° C.

EXAMPLE 48

N-({2-[2R]-5-Chloro-2-(4-phenylbutyl)(2,3-dihydrobenzo[b]furan-4-yl)]-(1R,2R)cyclopropyl}methyl)(ethylamino)carboxamide N-chlorosuccinimide (0.11 mmol) and the compound of Example 49 (0.1 mmol) were dissolved in acetonitrile (5 mL) and heated to reflux for 16 hours. The reaction mixture was cooled and the solvent removed in vacuo. The crude product was purified by preparative HPLC. The reaction yielded a mixture of mono- and di-chlorinated products in 40% to 50% yield, respectively.

$^1$H NMR (300 MHz, CDCl$_3$) δ 0.90 (t, J=6.9, 2H), 1.17 (t, J=7.2, 3H), 1.2–1.8 (broad m, 7H), 2.65 (t, J=7.4, 2H), 2.82 (m, 1H), 3.23 (m, 5H), 4.74 (m, 2H), 6.56 (d, J=8.5, 1H), 7.08 (d, J=8.5, 1H), 7.21 (m, 5H); m.p.=126–128° C.; MS(SEI) 427.23 (M+H)$^+$.

Conditions for the preparative HPLC are as follows: Column=YMC C18 S5 20 mm×100 mm; solvent A=10% MeOH, 90% H$_2$O, 0.1% TFA; solvent B=90% MeOH, 10% H$_2$O, 0.1% TFA; gradient from 30% to 100% B over 10 minutes with a 5 minute hold time at 100% B; flow=20 ml per minute; wavelength=220 nM; Analytical HPLC: retention time=4.73 minutes; purity=100%.

EXAMPLES 49 & 50

N-chlorosuccinimide (0.11 mmol) and the compound of Example 44 (0.1 mmol) were dissolved in acetonitrile (5 mL) and heated to reflux for 16 hours. The reaction mixture was cooled and the solvent removed in vacuo. The crude product was purified by preparative HPLC. The reaction yielded a mixture of mono- and di-chlorinated products in 40% to 50% yield, respectively.

EXAMPLE 49

N-({2-[(2R)-5,7-Dichloro-2-(4-phenylbutyl)(2,3-dihydrobenzo[b]furan-4-yl)](1R,2R)cyclopropyl}methyl)butanamide $^1$H NMR (300 MHz, CDCl$_3$) δ 0.91 (m, 2H), 0.98 (t, J=7.3, 3H), 1.26 (m, 2H), 1.53 (m, 2H), 1.66 (m, 5H), 1.85 (m, 1H), 2.22 (t, J=7.3, 2H), 2.66 (t, J=7.4, 2H), 2.89 (m, 1H), 3.67 (m, 3H), 4.84 (m, 1H), 5.89 (m, 1H), 7.15 (s, 1H), 7.24 (m, 5H); MS(SEI) 427.23 (M+H)$^+$.

Conditions for the preparative HPLC are as follows: Column=YMC C18 S5 20 mm×100 mm; solvent A=10% MeOH, 90% H$_2$O, 0.1% TFA; solvent B=90% MeOH, 10% H$_2$O, 0.1% TFA; gradient from 30% to 100% B over 10 minutes with a 5 minute hold time at 100% B; flow=20 mL per minute; wavelength=220 nM. Analytical HPLC: retention time=5.04 minutes; purity=97%.

EXAMPLE 50

N-({2-[(2R)-7-Chloro-2-(4-phenylbutyl)(2,3-dihydrobenzo[b]furan-4-yl)]-(1R,2R)cyclopropyl}methyl)butanamide $^1$H NMR (300 MHz, CDCl$_3$) δ 0.92 (m, 2H), 0.98 (t, J=7.4, 3H), 1.28 (m, 1H), 1.52 (m, 2H), 1.70 (m, 6H), 1.75 (m, 1H), 2.22 (t, J=7.3, 2H), 2.66 (t, J=7.5, 2H), 2.85 (m, 1H), 3.27 (m, 2H), 3.45 (m, 1H), 4.74 (m, 1H), 5.97 (m, 1H), 6.57 (d, J=8.5, 1H), 7.08 (d, J=8.5, 1H), 7.27 (m, 5H); MS(SEI) 426.20 (M+H)$^+$; m.p.=100–101° C.

Conditions for the preparative HPLC is as follows: Column=YMC C18 S5 mm×100 mm; solvent A=10% MeOH, 90% H$_2$O, 0.1% TFA; solvent B=90% MeOH, 10% H$_2$O, 0.1% TFA; gradient from 30% to 100% B over 10 minutes with a 5 minute hold time at 100% B; flow=20 ml per minute; wavelength=220 nM. Analytical HPLC: retention time=4.85 minutes; purity=100%.

What is claimed is:

1. A compound of Formula I:

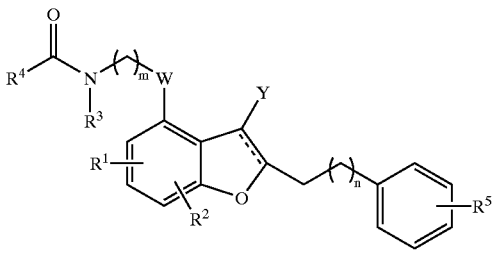

I wherein
the dashed line represents a single or double bond;
R$^1$ and R$^2$ are each independently hydrogen or halogen;
R$^3$ is hydrogen or C$_{1-4}$ alkyl;
R$^4$ is C$_{1-4}$ alkyl, C$_{3-6}$ cycloalkyl, C$_{1-3}$ haloalkyl, C$_{2-6}$ alkenyl, C$_{1-4}$ alkoxy, C$_{1-2}$ trifluoromethylalkyl, or C$_{1-4}$ alkylamino;
R$^5$ is hydrogen, halogen, C$_{1-4}$ alkyl, or C$_{1-4}$ alkoxy;
Y is hydrogen or halogen;
W is ethylene or a 1,2 disubstituted cyclopropyl group;
m is 1 or 2; and
n is 1 to 9.

2. The compound of claim 1 wherein the dashed line represents a single bond; R$^1$ and R$^2$ are hydrogen; R$^3$ is hydrogen; R$^4$ is C$_{1-4}$ alkyl or C$_{3-6}$ cycloalkyl; R$^5$ is hydrogen or halogen; Y is hydrogen; W is ethylene; m is 1; and n is 1 to 4.

3. The compound of claim 2 selected from the group consisting of: N-[3-[2-(4-phenylbutyl)-2,3-dihydrobenzofuran-4-yl]propyl]acetamide; N-[3-[2-(4-phenylbutyl)-2,3-dihydrobenzofuran-4-yl]propyl]propionamide; N-[3-[2-(4-phenylbutyl)-2,3-dihydrobenzofuran-4-yl]-propyl]butyramide; N-[3-[2-(4-phenylbutyl)-2,3-dihydrobenzofuran-4-yl]propyl]-2-methylpropionamide; and N-[3-[2-(4-phenylbutyl)-2,3-dihydrobenzofuran-4-yl]propyl]cyclopropane carboxamide.

4. The compound of claim 1 wherein the dashed line represents a double bond; R$^1$ and R$^2$ are hydrogen; R$^3$ is hydrogen; R$^4$ is C$_{1-4}$ alkyl; R$^5$ is hydrogen; Y is hydrogen; W is ethylene; m is 1; and n is 1 to 4.

5. The compound of claim 4 selected from the group consisting of: N-[3-[2-(4-phenylbutyl)benzofuran-4-yl]propyl]propionamide; and N-[3-[2-(4-phenylbutyl)benzofuran-4-yl]propyl]-2-methyl propionamide.

6. The compound of claim 1 wherein the dashed line represents a double bond; R$^1$ and R$^2$ are hydrogen; R$^3$ is hydrogen; R$^4$ is C$_{1-4}$ alkyl or C$_{3-6}$ cycloalkyl; R$^5$ is hydrogen or halogen; Y is hydrogen; W is a 1,2 disubstituted cyclopropyl group; m is 1; and n is 1 to 4.

7. The compound of claim 6 selected from the group consisting of:
N-({(1R,2R)-2-[2-(4-phenylbutyl)benzo[b]furan-4-yl]-cyclopropyl}methyl)acetamide;
(−)N-({(1R,2R)-2-[2-(4-phenylbutyl)benzo[b]furan-4-yl]-cyclopropyl}methyl)acetamide; and
N-({(1R,2R)-2-[2-(4-phenylbutyl)benzo[b]furan-4-yl]-cyclopropyl}methyl)propanamide.

8. The compound of claim 1 wherein the dashed line represents a single bond; R$^1$ and R$^2$ are hydrogen; R$^3$ is hydrogen; R$^4$ is C$_{1-4}$ alkyl or C$_{3-6}$ cycloalkyl; R$^5$ is hydrogen or halogen; Y is hydrogen; W is a 1,2 disubstituted cyclopropyl group; m is 1; and n is 1 to 4.

9. The compound of claim 8 selected from the group consisting of:
N-({2-[(2R)-2-(4-phenylbutyl)(2,3-dihydrobenzo[b]furan-4-yl)]-(1R,2R)cyclopropyl}methyl)acetamide;
N-({2-[(2R)-2-(4-phenylbutyl)(2,3-dihydrobenzo[b]furan-4-yl)]-(1R,2R)cyclopropyl}methyl)propanamide;
N-({2-[(2R)-2-(4-phenylbutyl)(2,3-dihydrobenzo[b]furan-4-yl)]-(1R,2R)cyclopropyl}methyl)butanamide; and
N-({2-[(2R)-2-(4-phenylbutyl)(2,3-dihydrobenzo[b]furan-4-yl)](1R,2R)cyclopropyl}methyl)cyclopropylcarboxamide.

10. A method of treating a circadian rhythm-related disorder in a mammal in need of such treatment comprising administering to the mammal a therapeutically effective amount of a compound as defined in claim 1.

11. A pharmaceutical composition for treating circadian rhythm-related disorders comprising a therapeutically effective amount of a compound as defined in claim 1 and a pharmaceutically acceptable carrier, adjuvant or diluent.

* * * * *